United States Patent
Pentelute et al.

(10) Patent No.: US 9,018,172 B2
(45) Date of Patent: Apr. 28, 2015

(54) MODIFICATION OF PEPTIDES VIA $S_NAR$ REACTIONS OF THIOLS WITH FLUORINATED AROMATICS

(71) Applicants: Bradley L. Pentelute, Cambridge, MA (US); Alexander M. Spokoyny, Framingham, MA (US); Yekui Zou, Worcester, MA (US); Chi Zhang, Cambridge, MA (US)

(72) Inventors: Bradley L. Pentelute, Cambridge, MA (US); Alexander M. Spokoyny, Framingham, MA (US); Yekui Zou, Worcester, MA (US); Chi Zhang, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/038,262

(22) Filed: Sep. 26, 2013

(65) Prior Publication Data

US 2014/0113871 A1    Apr. 24, 2014

Related U.S. Application Data

(60) Provisional application No. 61/821,790, filed on May 10, 2013, provisional application No. 61/705,747, filed on Sep. 26, 2012.

(51) Int. Cl.
| | |
|---|---|
| *A61K 38/12* | (2006.01) |
| *C07K 7/06* | (2006.01) |
| *C07K 7/08* | (2006.01) |
| *C07K 7/56* | (2006.01) |

(52) U.S. Cl.
CPC . *C07K 7/06* (2013.01); *A61K 38/12* (2013.01); *C07K 7/08* (2013.01); *C07K 7/56* (2013.01)

(58) Field of Classification Search
CPC ............ A61K 38/12; C07K 7/06; C07K 7/08; C07K 7/56
See application file for complete search history.

(56) References Cited

U.S. PATENT DOCUMENTS

| | | | |
|---|---|---|---|
| 2007/0082378 A1* | 4/2007 | Kent et al. ............ | 435/68.1 |
| 2011/0166392 A1 | 7/2011 | Umemoto | |
| 2012/0004417 A1 | 1/2012 | Dimagno | |

FOREIGN PATENT DOCUMENTS

WO    WO 2010011313 A3 * 12/2010

OTHER PUBLICATIONS

Chalker et al., "Methods for converting cysteine to dehydroalanine on peptides and proteins," Chem. Sci., 2(9):1666-1676 (2011).
Spokoyny et al., "A Perfluoroaryl-Cysteine $S_NAr$ Chemistry Approach to Unprotected Peptide Stapling," J. Am. Chem. Soc., 135(16):5946-5949 (2013).
Zhang et al., "Enzymatic "Click" Ligation: Selective Cysteine Modification in Polypeptides Enabled by Promiscuous Glutathione S-Transferase," Angew. Chem. Int. Ed., 52(52):14001-14005 (2013).
International Search Report and Written Opinion from parent PCT application PCT/US2013/062009 dated Mar. 18, 2014.

* cited by examiner

*Primary Examiner* — Marcela M Cordero Garcia
*Assistant Examiner* — Kaipeen Yang
(74) *Attorney, Agent, or Firm* — Foley Hoag LLP

(57) ABSTRACT

Disclosed are compounds and methods relating to a chemical transformation for the conjugation of unprotected peptide biomolecules via a $S_NAr$ process between highly fluorinated aryl moieties and thiols ("fluoroaryl-thiol-click").

32 Claims, 58 Drawing Sheets

| Solvent | Base (2 equiv) | Yield ($^{19}$F NMR) |
|---------|----------------|----------------------|
| DMF     | NEt$_3$        | >95%                 |
| MeCN    | NEt$_3$        | >95%                 |
| MeOH    | NEt$_3$        | NR                   |

| Solvent | Base (2 equiv) | Yield ($^{19}$F NMR) |
|---------|----------------|----------------------|
| DMF     | Na$_3$PO$_4$   | >95%                 |
| MeCN    | Na$_3$PO$_4$   | >95%                 |
| DMSO    | Na$_3$PO$_4$   | >95%                 |

Longer dithiol linkers = more defluorinated product.

Figure 18
VENKFNKEMRNAYWEIALLPNLNNQQKRAFI
1                                                                23
  RSLYDDPSGQANLLAEAKKLNDAQAPK
            41                                                58
Figure 19

Figure 22
(a)
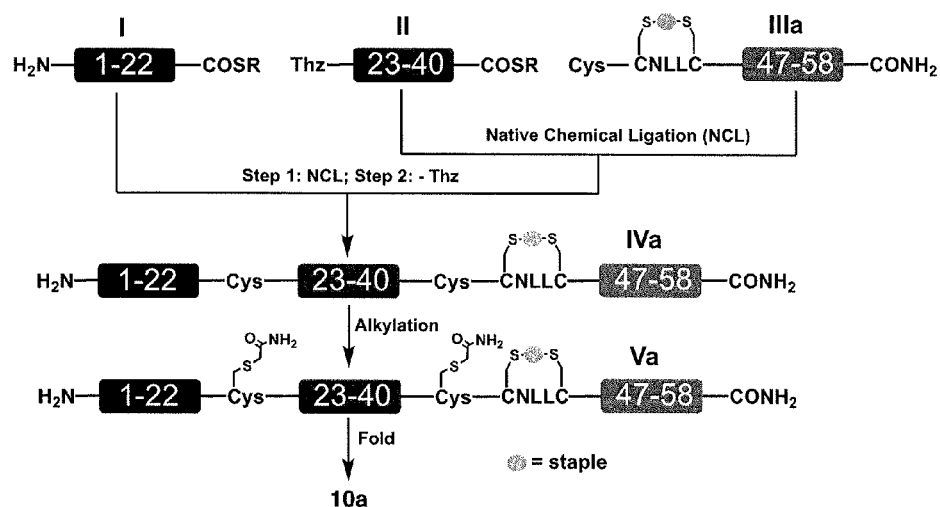
(b)
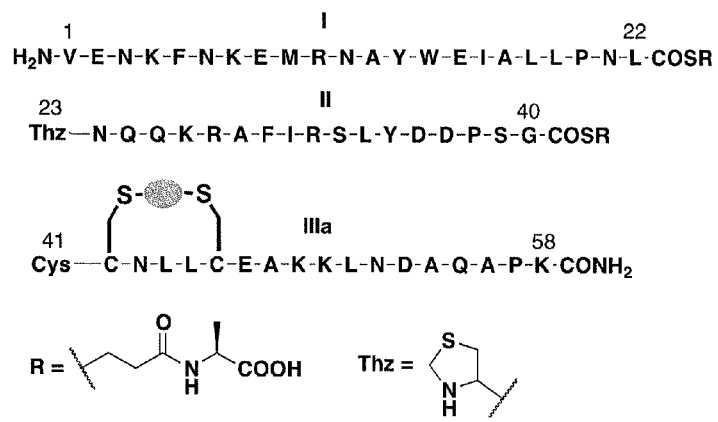

Figure 31

| | |
|---|---|
| i+1 | IKFTNGLCCLYESKR |
| i+2 | IKFTNGCLCLYESKR |
| i+3 | IKFTNGCLLCYESKR |
| i+4 | IKFTNCGLLCYESKR |
| i+5 | IKFTCNGLLCYESKR |
| i+6 | IKFTCNGLLYCESKR |
| i+7 | IKFTCNGLLYECSKR |
| i+8 | IKFTCNGLLYESCKR |
| i+9 | IKFCTNGLLYESCKR |
| i+10 | IKCFTNGLLYESCKR |
| i+11 | IKCFTNGLLYESKCR |
| i+12 | ICKFTNGLLYESKCR |
| i+13 | CIKFTNGLLYESKCR |
| i+14 | CIKFTNGLLYESKRC |

Figure 33

| Entry | Peptide | n | | Conversion (%) | | |
|---|---|---|---|---|---|---|
| 1 | H₂N-IKFTNGLCCLYESKR-CONH₂ | 1 | 79 | 32 | 93 | 86 |
| 2 | H₂N-IKFTNGCLCLYESKR-CONH₂ | 2 | 76 | 40 | 90 | 87 |
| 3 | H₂N-IKFTNGCLLCYESKR-CONH₂ | 3 | 72 | 44 | 80 | 90 |
| 4 | H₂N-IKFTNCGLLCYESKR-CONH₂ | 4 | 77 | 87 | 91 | 91 |
| 5 | H₂N-IKFTCNGLLCYESKR-CONH₂ | 5 | 75 | 67 | 91 | 80 |
| 6 | H₂N-IKFTCNGLLYCESKR-CONH₂ | 6 | 78 | 84 | 81 | 75 |
| 7 | H₂N-IKFTCNGLLYECSKR-CONH₂ | 7 | 83 | 93 | 90 | 88 |
| 8 | H₂N-IKFTCNGLLYESCKR-CONH₂ | 8 | 80 | 81 | 92 | 88 |
| 9 | H₂N-IKFCTNGLLYESCKR-CONH₂ | 9 | 60 | 93 | 91 | 85 |
| 10 | H₂N-IKCFTNGLLYESCKR-CONH₂ | 10 | 63 | 95 | 94 | 82 |
| 11 | H₂N-IKCFTNGLLYESKCR-CONH₂ | 11 | 60 | 94 | 93 | 90 |
| 12 | H₂N-ICKFTNGLLYESKCR-CONH₂ | 12 | 68 | 92 | 91 | 87 |
| 13 | H₂N-CIKFTNGLLYESKCR-CONH₂ | 13 | 30 | 70 | 78 | 60 |
| 14 | H₂N-CIKFTNGLLYESKRC-CONH₂ | 14 | 40 | 91 | 90 | 75 |

(a)

(b)

| Entry | H₃N⁺—peptide—COO⁻ (SH) | Reaction time (min) | Yield(%) |
|---|---|---|---|
| 1 | Glutathione | 10 | >99 |
| 2 | H₃N⁺-YECGGLL-COO⁻ | 30 | >99 |
| 3 | H₃N⁺-YECGLLL-COO⁻ | 30 | 86 (>99) |
| 4 | H₃N⁺-YECGHLL-COO⁻ | 30 | 98 (>99) |
| 5 | H₃N⁺-YECGKLL-COO⁻ | 30 | 68 (>99) |
| 6 | H₃N⁺-YECGPLL-COO⁻ | 30 | 67 (>99) |
| 7 | H₃N⁺-YECGGGLL-COO⁻ | 30 | >99 |
| 8 | H₃N⁺-ECGGLL-COO⁻ | 240 | <5 (13) |
| 9 | H₃N⁺-ECGGLL-COO⁻ | 240 | <5 (35) |
| 10 | H₃N⁺-DCGGLL-COO⁻ | 240 | <5 (23) |
| 11 | H₃N⁺-NCGGLL-COO⁻ | 240 | <5 |
| 12 | H₃N⁺-QCGGLL-COO⁻ | 240 | <5 |
| 13 | H₃N⁺-GYECGGLL-COO⁻ | | |

Figure 39
(a)
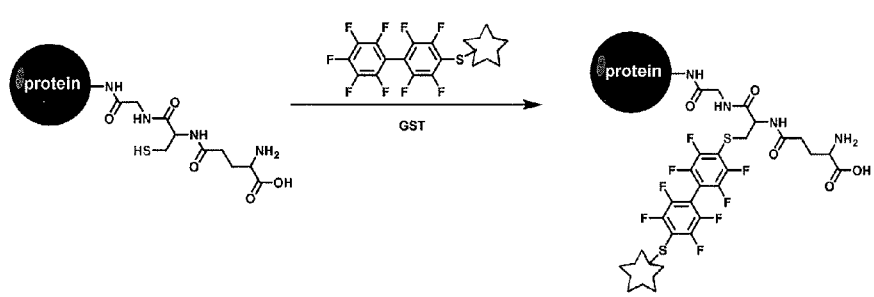
(b)
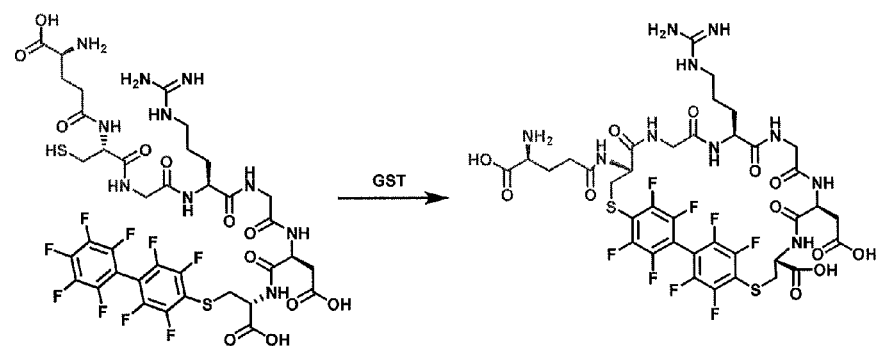

Figure 43
| Compound | Charge on C (e) | Charge on F (e) | Total charge of C-F (e) |
|---|---|---|---|
|  | 0.199 | -0.183 | 0.016 |
|  | 0.199 | -0.183 | 0.016 |
|  | 0.197 | -0.182 | 0.015 |
|  | 0.198 | -0.185 | 0.013 |
|  | 0.196 | -0.183 | 0.013 |
|  | 0.196 | -0.183 | 0.013 |
|  | 0.195 | -0.184 | 0.011 |
|  | 0.195 | -0.187 | 0.008 |
|  | 0.185 | -0.177 | 0.008 |
|  | 0.193 | -0.187 | 0.006 |
|  | 0.192 | -0.188 | 0.004 |
|  | 0.192 | -0.191 | 0.001 |

Figure 43 (continued)
| Compound | Charge on C (e) | Charge on F (e) | Total charge of C-F (e) |
|---|---|---|---|
|  | 0.188 | -0.188 | 0.000 |
| 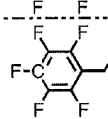 | 0.190 | -0.192 | -0.002 |
|  | 0.187 | -0.189 | -0.002 |
| 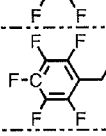 | 0.189 | -0.193 | -0.004 |

Figure 47

| Peptide | Sequence | Obs. mass | Calc. mass |
|---|---|---|---|
| 1 | H$_2$N-ITPCNLLF*YYGKKK-CONH$_2$ | 1775.9 ± 0.1 | 1775.89 |
| 3 | H$_2$N-VTLPSTCGAS-CONH$_2$ | 933.5 ± 0.1 | 933.46 |
| 5a | H$_2$N-γ-ECGGLL-CONH$_2$ | 589.3 ± 0.1 | 589.29 |
| 5b | H$_2$N-γ-ECGLLL-CONH$_2$ | 645.4 ± 0.1 | 645.35 |
| 5c | H$_2$N-γ-ECGHLL-CONH$_2$ | 669.3 ± 0.1 | 669.33 |
| 5d | H$_2$N-γ-ECGKLL-CONH$_2$ | 660.4 ± 0.1 | 660.36 |
| 5e | H$_2$N-γ-ECGPLL-CONH$_2$ | 629.3 ± 0.1 | 629.32 |
| 5f | H$_2$N-γ-ECGGGLL-CONH$_2$ | 646.3 ± 0.1 | 646.31 |
| 5g | H$_2$N-ECGGLL-CONH$_2$ | 589.3 ± 0.1 | 589.29 |
| 5h | H$_2$N-DCGGLL-CONH$_2$ | 575.3 ± 0.1 | 575.27 |
| 5i | H$_2$N-γ-ECG-CONHNH$_2$ | 321.1 ± 0.1 | 321.11 |
| 5j | H$_2$N-γ-ECGGALF-CONHNH$_2$ | 709.3 ± 0.1 | 709.32 |
| 11a | Biotin-RRC-CONH$_2$ | 658.3 ± 0.1 | 658.31 |
| 12a | H$_2$N- γ-EC(S-*t*Bu)GRGDC-CONH$_2$ | 825.3 ± 0.1 | 825.29 |
| 14 | H$_2$N- γ -ECGGPTAAKESCLL-CONH$_2$ | 1376.6 ± 0.1 | 1376.64 |
| 14a | H$_2$N- γ -ECGGPTAAKESC(S-*t*Bu)LL-CONH$_2$ | 1464.7 ± 0.1 | 1464.68 |

SEQUENCE LISTING

```
<160> NUMBER OF SEQ ID NOS: 140

<210> SEQ ID NO 1
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide labeled with FITC tag

<400> SEQUENCE: 1

Ile Thr Pro Cys Asn Leu Leu Cys Tyr Tyr Gly Lys Lys Lys
1               5                   10

<210> SEQ ID NO 2
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term COSR

<400> SEQUENCE: 2

Val Glu Asn Lys Phe Asn Lys Glu Met Arg Asn Ala Tyr Trp Glu Ile
1               5                   10                  15

Ala Leu Leu Pro Asn Leu
            20
```

-continued

```
<210> SEQ ID NO 3
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Thz
<220> FEATURE:
<223> OTHER INFORMATION: C-term COSR

<400> SEQUENCE: 3

Xaa Asn Gln Gln Lys Arg Ala Phe Ile Arg Ser Leu Tyr Asp Asp Pro
1               5                   10                  15

Ser Gly

<210> SEQ ID NO 4
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Thz
<220> FEATURE:
<223> OTHER INFORMATION: C-term CONH2

<400> SEQUENCE: 4

Xaa Cys Asn Leu Leu Cys Glu Ala Lys Lys Leu Asn Asp Ala Gln Ala
1               5                   10                  15

Pro Lys

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Modified Cys for cross-linking
<220> FEATURE:
<223> OTHER INFORMATION: C-term CONH2
<220> FEATURE:
<223> OTHER INFORMATION: see specification as filed for detailed
      description of substitutions and preferred embodiments

<400> SEQUENCE: 5

Val Thr Leu Pro Ser Thr Cys Gly Ala Ser
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
```

```
<223> OTHER INFORMATION: Gamma-Glu
<220> FEATURE:
<223> OTHER INFORMATION: C-term CONH2

<400> SEQUENCE: 6

Glu Cys Gly Pro Thr Ala Ala Lys Glu Ser Cys Leu Leu
1               5                   10

<210> SEQ ID NO 7
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Thz
<220> FEATURE:
<221> NAME/KEY: misc_feature
<222> LOCATION: (2)..(6)
<223> OTHER INFORMATION: Modified linkage between residues
<220> FEATURE:
<223> OTHER INFORMATION: C-term CONH2
<220> FEATURE:
<223> OTHER INFORMATION: see specification as filed for detailed
      description of substitutions and preferred embodiments

<400> SEQUENCE: 7

Xaa Cys Asn Leu Leu Cys Glu Ala Lys Lys Leu Asn Asp Ala Gln Ala
1               5                   10                  15

Pro Lys

<210> SEQ ID NO 8
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(6)
<223> OTHER INFORMATION: Modified linkage between residues
<220> FEATURE:
<223> OTHER INFORMATION: C-term CONH2
<220> FEATURE:
<223> OTHER INFORMATION: see specification as filed for detailed
      description of substitutions and preferred embodiments

<400> SEQUENCE: 8

Cys Cys Asn Leu Leu Cys Glu Ala Lys Lys Leu Asn Asp Ala Gln Ala
1               5                   10                  15

Pro Lys

<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: misc_feature
<222> LOCATION: (4)..(8)
<223> OTHER INFORMATION: Modified linkage between residues
<220> FEATURE:
<223> OTHER INFORMATION: C-term NH2
```

-continued

```
<220> FEATURE:
<223> OTHER INFORMATION: see specification as filed for detailed
      description of substitutions and preferred embodiments

<400> SEQUENCE: 9

Ile Thr Pro Cys Asn Leu Leu Cys Tyr Tyr Gly Lys Lys Lys
1               5                   10

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(6)
<223> OTHER INFORMATION: Modified linkage between residues
<220> FEATURE:
<223> OTHER INFORMATION: C-term CONH2
<220> FEATURE:
<223> OTHER INFORMATION: see specification as filed for detailed
      description of substitutions and preferred embodiments

<400> SEQUENCE: 10

Tyr Cys Glu Arg Ser Cys Asn Met Lys
1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: misc_feature
<222> LOCATION: (2)..(6)
<223> OTHER INFORMATION: Modified linkage between residues
<220> FEATURE:
<223> OTHER INFORMATION: C-term NH2
<220> FEATURE:
<223> OTHER INFORMATION: see specification as filed for detailed
      description of substitutions and preferred embodiments

<400> SEQUENCE: 11

Tyr Cys Gly Gly Gly Cys Ala Leu
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: misc_feature
<222> LOCATION: (2)..(6)
<223> OTHER INFORMATION: Modified linkage between residues
<220> FEATURE:
<223> OTHER INFORMATION: C-term NH2
<220> FEATURE:
<223> OTHER INFORMATION: see specification as filed for detailed
      description of substitutions and preferred embodiments

<400> SEQUENCE: 12
```

```
Tyr Cys Glu Arg Ser Cys Asn Met Lys
1               5
```

<210> SEQ ID NO 13
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Thz
<220> FEATURE:
<221> NAME/KEY: misc_feature
<222> LOCATION: (2)..(6)
<223> OTHER INFORMATION: Modified linkage between residues
<220> FEATURE:
<223> OTHER INFORMATION: C-term CONH2
<220> FEATURE:
<223> OTHER INFORMATION: see specification as filed for detailed
      description of substitutions and preferred embodiments

<400> SEQUENCE: 13

```
Xaa Cys Asn Leu Leu Cys Glu Ala Lys Lys Leu Asn Asp Ala Gln Ala
1               5                   10                  15

Pro Lys
```

<210> SEQ ID NO 14
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(6)
<223> OTHER INFORMATION: Modified linkage between residues
<220> FEATURE:
<223> OTHER INFORMATION: C-term CONH2
<220> FEATURE:
<223> OTHER INFORMATION: see specification as filed for detailed
      description of substitutions and preferred embodiments

<400> SEQUENCE: 14

```
Cys Cys Asn Leu Leu Cys Glu Ala Lys Lys Leu Asn Asp Ala Gln Ala
1               5                   10                  15

Pro Lys
```

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(6)
<223> OTHER INFORMATION: Modified linkage between residues
<220> FEATURE:
<223> OTHER INFORMATION: C-term CONH2
<220> FEATURE:
<223> OTHER INFORMATION: see specification as filed for detailed
      description of substitutions and preferred embodiments

<400> SEQUENCE: 15

```
Tyr Cys Glu Arg Ser Cys Asn Met Lys
1               5
```

```
<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: misc_feature
<222> LOCATION: (4)..(8)
<223> OTHER INFORMATION: Modified linkage between residues
<220> FEATURE:
<223> OTHER INFORMATION: C-term NH2
<220> FEATURE:
<223> OTHER INFORMATION: see specification as filed for detailed
      description of substitutions and preferred embodiments

<400> SEQUENCE: 16

Ile Thr Pro Cys Asn Leu Leu Cys Tyr Tyr Gly Lys Lys Lys
1               5                   10

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: misc_feature
<222> LOCATION: (2)..(6)
<223> OTHER INFORMATION: Modified linkage between residues
<220> FEATURE:
<223> OTHER INFORMATION: C-term NH2
<220> FEATURE:
<223> OTHER INFORMATION: see specification as filed for detailed
      description of substitutions and preferred embodiments

<400> SEQUENCE: 17

Tyr Cys Gly Gly Gly Cys Ala Leu
1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: misc_feature
<222> LOCATION: (2)..(6)
<223> OTHER INFORMATION: Modified linkage between residues
<220> FEATURE:
<223> OTHER INFORMATION: C-term NH2
<220> FEATURE:
<223> OTHER INFORMATION: see specification as filed for detailed
      description of substitutions and preferred embodiments

<400> SEQUENCE: 18

Tyr Cys Glu Arg Ser Cys Asn Met Lys
1               5

<210> SEQ ID NO 19
<211> LENGTH: 12
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (5)..(9)
<223> OTHER INFORMATION: Modified linkage between residues
<220> FEATURE:
<221> NAME/KEY: MOD_RES
<222> LOCATION: (7)..(7)
<223> OTHER INFORMATION: Phe-CF3
<220> FEATURE:
<223> OTHER INFORMATION: C-term CONH2
<220> FEATURE:
<223> OTHER INFORMATION: see specification as filed for detailed
      description of substitutions and preferred embodiments

<400> SEQUENCE: 19

Thr Ala Trp Tyr Cys Asn Phe Glu Cys Leu Leu Arg
1               5                   10

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala-FITC or absent
<220> FEATURE:
<221> NAME/KEY: misc_feature
<222> LOCATION: (5)..(9)
<223> OTHER INFORMATION: Modified linkage between residues
<220> FEATURE:
<223> OTHER INFORMATION: C-term CONH2
<220> FEATURE:
<223> OTHER INFORMATION: see specification as filed for detailed
      description of substitutions and preferred embodiments

<400> SEQUENCE: 20

Ala Ile Thr Phe Cys Asp Leu Leu Cys Tyr Tyr Gly Lys Lys Lys
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala-FITC or absent
<220> FEATURE:
<221> NAME/KEY: misc_feature
<222> LOCATION: (5)..(9)
<223> OTHER INFORMATION: Modified linkage between residues
<220> FEATURE:
<223> OTHER INFORMATION: C-term CONH2
<220> FEATURE:
<223> OTHER INFORMATION: see specification as filed for detailed
      description of substitutions and preferred embodiments

<400> SEQUENCE: 21

Ala Ile Thr Phe Cys Asp Leu Leu Cys Tyr Tyr Gly Lys Lys Lys
1               5                   10                  15
```

```
<210> SEQ ID NO 22
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (4)..(4)
<223> OTHER INFORMATION: Modified Phe for cross-linking
<220> FEATURE:
<221> NAME/KEY: misc_feature
<222> LOCATION: (4)..(8)
<223> OTHER INFORMATION: Modified linkage between residues
<220> FEATURE:
<221> NAME/KEY: MOD_RES
<222> LOCATION: (8)..(8)
<223> OTHER INFORMATION: Modified Phe for cross-linking
<220> FEATURE:
<223> OTHER INFORMATION: C-term NH2
<220> FEATURE:
<223> OTHER INFORMATION: see specification as filed for detailed
      description of substitutions and preferred embodiments

<400> SEQUENCE: 22

Ile Thr Pro Phe Asn Leu Leu Phe Tyr Tyr Gly Lys Lys Lys
1               5                   10

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Modified Phe for cross-linking
<220> FEATURE:
<221> NAME/KEY: misc_feature
<222> LOCATION: (2)..(6)
<223> OTHER INFORMATION: Modified linkage between residues
<220> FEATURE:
<221> NAME/KEY: MOD_RES
<222> LOCATION: (6)..(6)
<223> OTHER INFORMATION: Modified Phe for cross-linking
<220> FEATURE:
<223> OTHER INFORMATION: C-term CONH2
<220> FEATURE:
<223> OTHER INFORMATION: see specification as filed for detailed
      description of substitutions and preferred embodiments

<400> SEQUENCE: 23

Ser Phe Gly Gly Gly Phe Ala Ile
1               5

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Modified Phe for cross-linking
<220> FEATURE:
<223> OTHER INFORMATION: C-term NH2
<220> FEATURE:
<223> OTHER INFORMATION: see specification as filed for detailed
```

```
                        description of substitutions and preferred embodiments

<400> SEQUENCE: 24

Phe Gly Thr Leu Lys Ala
1               5

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Modified Lys for cross-linking
<220> FEATURE:
<223> OTHER INFORMATION: see specification as filed for detailed
      description of substitutions and preferred embodiments

<400> SEQUENCE: 25

Lys Ser Leu Gly Tyr His
1               5

<210> SEQ ID NO 26
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (4)..(4)
<223> OTHER INFORMATION: Perfluorophenyl-modified phenylalanine
<220> FEATURE:
<221> NAME/KEY: MOD_RES
<222> LOCATION: (8)..(8)
<223> OTHER INFORMATION: Perfluorophenyl-modified phenylalanine
<220> FEATURE:
<223> OTHER INFORMATION: C-term NH2
<220> FEATURE:
<223> OTHER INFORMATION: see specification as filed for detailed
      description of substitutions and preferred embodiments

<400> SEQUENCE: 26

Ile Thr Pro Phe Asn Leu Leu Phe Tyr Tyr Gly Lys Lys Lys
1               5                   10

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Perfluorophenyl-modified phenylalanine
<220> FEATURE:
<221> NAME/KEY: MOD_RES
<222> LOCATION: (6)..(6)
<223> OTHER INFORMATION: Perfluorophenyl-modified phenylalanine
<220> FEATURE:
<223> OTHER INFORMATION: C-term CONH2
<220> FEATURE:
<223> OTHER INFORMATION: see specification as filed for detailed
      description of substitutions and preferred embodiments
```

```
<400> SEQUENCE: 27

Ser Phe Gly Gly Gly Phe Ala Ile
1               5

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Perfluorophenyl-modified phenylalanine
<220> FEATURE:
<223> OTHER INFORMATION: C-term NH2
<220> FEATURE:
<223> OTHER INFORMATION: see specification as filed for detailed
      description of substitutions and preferred embodiments

<400> SEQUENCE: 28

Phe Gly Thr Leu Lys Ala
1               5

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Modified Lys for cross-linking
<220> FEATURE:
<223> OTHER INFORMATION: see specification as filed for detailed
      description of substitutions and preferred embodiments

<400> SEQUENCE: 29

Lys Ser Leu Gly Tyr His
1               5

<210> SEQ ID NO 30
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (4)..(11)
<223> OTHER INFORMATION: Modified linkage between residues
<220> FEATURE:
<223> OTHER INFORMATION: see specification as filed for detailed
      description of substitutions and preferred embodiments

<400> SEQUENCE: 30

Ile Thr Pro Cys Asn Leu Leu Asn Tyr Tyr Cys Pro Lys Lys Lys
1               5                   10                  15

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 31

Leu Pro Ser Thr Gly Gly His His His His His
1               5                   10

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 32

His His His His His His
1               5

<210> SEQ ID NO 33
<211> LENGTH: 373
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Met Ser Asp Ser Glu Val Asn Gln Glu Ala Lys Pro Glu Val Lys Pro
1               5                   10                  15

Glu Val Lys Pro Glu Thr His Ile Asn Leu Lys Val Ser Asp Gly Ser
                20                  25                  30

Ser Glu Ile Phe Phe Lys Ile Lys Lys Thr Thr Pro Leu Arg Arg Leu
            35                  40                  45

Met Glu Ala Phe Ala Lys Arg Gln Gly Lys Glu Met Asp Ser Leu Arg
        50                  55                  60

Phe Leu Tyr Asp Gly Ile Arg Ile Gln Ala Asp Gln Thr Pro Glu Asp
65                  70                  75                  80

Leu Asp Met Glu Asp Asn Asp Ile Ile Glu Ala His Arg Glu Gln Ile
                85                  90                  95

Gly Gly Cys Gly Gly His Gly Asp Val Gly Met His Val Lys Glu Lys
            100                 105                 110

Glu Lys Asn Lys Asp Glu Asn Lys Arg Lys Asp Glu Glu Arg Asn Lys
        115                 120                 125

Thr Gln Glu Glu His Leu Lys Glu Ile Met Lys His Ile Val Lys Ile
130                 135                 140

Glu Val Lys Gly Glu Glu Ala Val Lys Lys Glu Ala Ala Glu Lys Leu
145                 150                 155                 160

Leu Glu Lys Val Pro Ser Asp Val Leu Glu Met Tyr Lys Ala Ile Gly
                165                 170                 175

Gly Lys Ile Tyr Ile Val Asp Gly Asp Ile Thr Lys His Ile Ser Leu
            180                 185                 190

Glu Ala Leu Ser Glu Asp Lys Lys Ile Lys Asp Ile Tyr Gly Lys
        195                 200                 205

Asp Ala Leu Leu His Glu His Tyr Val Tyr Ala Lys Glu Gly Tyr Glu
    210                 215                 220

Pro Val Leu Val Ile Gln Ser Ser Glu Asp Tyr Val Glu Asn Thr Glu
225                 230                 235                 240

Lys Ala Leu Asn Val Tyr Tyr Glu Ile Gly Lys Ile Leu Ser Arg Asp
                245                 250                 255

Ile Leu Ser Lys Ile Asn Gln Pro Tyr Gln Lys Phe Leu Asp Val Leu
```

```
                260             265              270
Asn Thr Ile Lys Asn Ala Ser Asp Ser Asp Gly Gln Asp Leu Leu Phe
        275                 280             285

Thr Asn Gln Leu Lys Glu His Pro Thr Asp Phe Ser Val Glu Phe Leu
    290                 295             300

Glu Gln Asn Ser Asn Glu Val Gln Glu Val Phe Ala Lys Ala Phe Ala
305                 310             315                 320

Tyr Tyr Ile Glu Pro Gln His Arg Asp Val Leu Gln Leu Tyr Ala Pro
                325             330             335

Glu Ala Phe Asn Tyr Met Asp Lys Phe Asn Glu Gln Glu Ile Asn Leu
            340             345             350

Ser Leu Glu Glu Leu Lys Asp Gln Arg Leu Pro Ser Thr Gly Gly His
        355             360             365

His His His His His
    370

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term CONH2

<400> SEQUENCE: 34

Tyr Cys Glu Arg Ser Cys Asn Met Lys
1               5

<210> SEQ ID NO 35
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term CONH2

<400> SEQUENCE: 35

Ile Thr Pro Cys Asn Leu Leu Cys Tyr Tyr Gly Lys Lys Lys
1               5                   10

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term NH2

<400> SEQUENCE: 36

Tyr Cys Gly Gly Gly Cys Ala Leu
1               5

<210> SEQ ID NO 37
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term NH2

<400> SEQUENCE: 37

Tyr Cys Glu Arg Ser Cys Asn Met Lys
1               5

<210> SEQ ID NO 38
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term NH2

<400> SEQUENCE: 38

Ile Thr Pro Cys Asn Leu Leu Cys Tyr Tyr Gly Lys Lys Lys
1               5                   10

<210> SEQ ID NO 39
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (4)..(4)
<223> OTHER INFORMATION: Modified Phe for cross-linking
<220> FEATURE:
<221> NAME/KEY: MOD_RES
<222> LOCATION: (8)..(8)
<223> OTHER INFORMATION: Modified Phe for cross-linking
<220> FEATURE:
<223> OTHER INFORMATION: C-term NH2
<220> FEATURE:
<223> OTHER INFORMATION: see specification as filed for detailed
      description of substitutions and preferred embodiments

<400> SEQUENCE: 39

Ile Thr Pro Phe Asn Leu Leu Phe Tyr Tyr Gly Lys Lys Lys
1               5                   10

<210> SEQ ID NO 40
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Val Glu Asn Lys Phe Asn Lys Glu Met Arg Asn Ala Tyr Trp Glu Ile
1               5                   10                  15

Ala Leu Leu Pro Asn Leu Asn Asn Gln Gln Lys Arg Ala Phe Ile Arg
                20                  25                  30

Ser Leu Tyr Asp Asp Pro Ser Gly Gln Ala Asn Leu Leu Ala Glu Ala
            35                  40                  45
```

```
Lys Lys Leu Asn Asp Ala Gln Ala Pro Lys
    50                  55

<210> SEQ ID NO 41
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(6)
<223> OTHER INFORMATION: Modified linkage between residues
<220> FEATURE:
<223> OTHER INFORMATION: see specification as filed for detailed
      description of substitutions and preferred embodiments

<400> SEQUENCE: 41

Cys Cys Asn Leu Leu Cys
1               5

<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys CONH2
<220> FEATURE:
<221> NAME/KEY: misc_feature
<222> LOCATION: (2)..(6)
<223> OTHER INFORMATION: Modified linkage between residues
<220> FEATURE:
<223> OTHER INFORMATION: see specification as filed for detailed
      description of substitutions and preferred embodiments

<400> SEQUENCE: 42

Cys Cys Asn Leu Leu Cys
1               5

<210> SEQ ID NO 43
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(6)
<223> OTHER INFORMATION: Modified linkage between residues
<220> FEATURE:
<223> OTHER INFORMATION: C-term CONH2
<220> FEATURE:
<223> OTHER INFORMATION: see specification as filed for detailed
      description of substitutions and preferred embodiments

<400> SEQUENCE: 43

Cys Cys Asn Leu Leu Cys Glu Ala Lys Lys Leu Asn Asp Ala Gln Ala
1               5                   10                  15

Pro Lys

<210> SEQ ID NO 44
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala-FITC or not present
<220> FEATURE:
<221> NAME/KEY: MOD_RES
<222> LOCATION: (5)..(5)
<223> OTHER INFORMATION: Modified Cys for cross-linking
<220> FEATURE:
<221> NAME/KEY: misc_feature
<222> LOCATION: (5)..(9)
<223> OTHER INFORMATION: Possible modified linkage between residues
<220> FEATURE:
<221> NAME/KEY: MOD_RES
<222> LOCATION: (9)..(9)
<223> OTHER INFORMATION: Modified Cys for cross-linking
<220> FEATURE:
<223> OTHER INFORMATION: C-term CONH2
<220> FEATURE:
<223> OTHER INFORMATION: see specification as filed for detailed
      description of substitutions and preferred embodiments

<400> SEQUENCE: 44

Ala Ile Thr Phe Cys Asp Leu Leu Cys Tyr Tyr Gly Lys Lys Lys
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala-FITC or not present
<220> FEATURE:
<221> NAME/KEY: MOD_RES
<222> LOCATION: (5)..(5)
<223> OTHER INFORMATION: Modified Cys for cross-linking
<220> FEATURE:
<223> OTHER INFORMATION: C-term CONH2
<220> FEATURE:
<223> OTHER INFORMATION: see specification as filed for detailed
      description of substitutions and preferred embodiments

<400> SEQUENCE: 45

Ala Ile Thr Phe Cys Asp Leu Leu Ser Tyr Tyr Gly Lys Lys Lys
1               5                   10                  15

<210> SEQ ID NO 46
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala-FITC or not present
<220> FEATURE:
<221> NAME/KEY: MOD_RES
<222> LOCATION: (5)..(5)
<223> OTHER INFORMATION: Modified Ala for cross-linking
<220> FEATURE:
<221> NAME/KEY: misc_feature
<222> LOCATION: (5)..(9)
<223> OTHER INFORMATION: Modified linkage between residues
<220> FEATURE:
<221> NAME/KEY: MOD_RES
```

```
<222> LOCATION: (9)..(9)
<223> OTHER INFORMATION: Modified Ala for cross-linking
<220> FEATURE:
<223> OTHER INFORMATION: C-term CONH2
<220> FEATURE:
<223> OTHER INFORMATION: see specification as filed for detailed
      description of substitutions and preferred embodiments

<400> SEQUENCE: 46

Ala Ile Thr Phe Ala Asp Leu Leu Ala Tyr Tyr Gly Pro
1               5                   10

<210> SEQ ID NO 47
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (4)..(11)
<223> OTHER INFORMATION: Modified linkage between residues
<220> FEATURE:
<223> OTHER INFORMATION: see specification as filed for detailed
      description of substitutions and preferred embodiments

<400> SEQUENCE: 47

Ile Thr Pro Cys Asn Leu Leu Asn Tyr Tyr Cys Pro Lys Lys Lys
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (8)..(9)
<223> OTHER INFORMATION: Modified linkage between residues
<220> FEATURE:
<223> OTHER INFORMATION: see specification as filed for detailed
      description of substitutions and preferred embodiments

<400> SEQUENCE: 48

Ile Lys Phe Thr Asn Gly Leu Cys Cys Leu Tyr Glu Ser Lys Arg
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (7)..(9)
<223> OTHER INFORMATION: Modified linkage between residues
<220> FEATURE:
<223> OTHER INFORMATION: see specification as filed for detailed
      description of substitutions and preferred embodiments

<400> SEQUENCE: 49

Ile Lys Phe Thr Asn Gly Cys Leu Cys Leu Tyr Glu Ser Lys Arg
1               5                   10                  15

<210> SEQ ID NO 50
<211> LENGTH: 15
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (7)..(10)
<223> OTHER INFORMATION: Modified linkage between residues
<220> FEATURE:
<223> OTHER INFORMATION: see specification as filed for detailed
      description of substitutions and preferred embodiments

<400> SEQUENCE: 50

Ile Lys Phe Thr Asn Gly Cys Leu Leu Cys Tyr Glu Ser Lys Arg
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (6)..(10)
<223> OTHER INFORMATION: Modified linkage between residues
<220> FEATURE:
<223> OTHER INFORMATION: see specification as filed for detailed
      description of substitutions and preferred embodiments

<400> SEQUENCE: 51

Ile Lys Phe Thr Asn Cys Gly Leu Leu Cys Tyr Glu Ser Lys Arg
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (5)..(10)
<223> OTHER INFORMATION: Modified linkage between residues
<220> FEATURE:
<223> OTHER INFORMATION: see specification as filed for detailed
      description of substitutions and preferred embodiments

<400> SEQUENCE: 52

Ile Lys Phe Thr Cys Asn Gly Leu Leu Cys Tyr Glu Ser Lys Arg
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (5)..(11)
<223> OTHER INFORMATION: Modified linkage between residues
<220> FEATURE:
<223> OTHER INFORMATION: see specification as filed for detailed
      description of substitutions and preferred embodiments

<400> SEQUENCE: 53

Ile Lys Phe Thr Cys Asn Gly Leu Leu Tyr Cys Glu Ser Lys Arg
```

<210> SEQ ID NO 54
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (5)..(12)
<223> OTHER INFORMATION: Modified linkage between residues
<220> FEATURE:
<223> OTHER INFORMATION: see specification as filed for detailed
      description of substitutions and preferred embodiments

<400> SEQUENCE: 54

Ile Lys Phe Thr Cys Asn Gly Leu Leu Tyr Glu Cys Ser Lys Arg
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (5)..(13)
<223> OTHER INFORMATION: Modified linkage between residues
<220> FEATURE:
<223> OTHER INFORMATION: see specification as filed for detailed
      description of substitutions and preferred embodiments

<400> SEQUENCE: 55

Ile Lys Phe Thr Cys Asn Gly Leu Leu Tyr Glu Ser Cys Lys Arg
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (4)..(13)
<223> OTHER INFORMATION: Modified linkage between residues
<220> FEATURE:
<223> OTHER INFORMATION: see specification as filed for detailed
      description of substitutions and preferred embodiments

<400> SEQUENCE: 56

Ile Lys Phe Cys Thr Asn Gly Leu Leu Tyr Glu Ser Cys Lys Arg
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (3)..(13)
<223> OTHER INFORMATION: Modified linkage between residues
<220> FEATURE:
<223> OTHER INFORMATION: see specification as filed for detailed -continued description of substitutions and preferred embodiments

<400> SEQUENCE: 57

Ile Lys Cys Phe Thr Asn Gly Leu Leu Tyr Glu Ser Cys Lys Arg
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (3)..(14)
<223> OTHER INFORMATION: Modified linkage between residues
<220> FEATURE:
<223> OTHER INFORMATION: see specification as filed for detailed
      description of substitutions and preferred embodiments

<400> SEQUENCE: 58

Ile Lys Cys Phe Thr Asn Gly Leu Leu Tyr Glu Ser Lys Cys Arg
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(14)
<223> OTHER INFORMATION: Modified linkage between residues
<220> FEATURE:
<223> OTHER INFORMATION: see specification as filed for detailed
      description of substitutions and preferred embodiments

<400> SEQUENCE: 59

Ile Cys Lys Phe Thr Asn Gly Leu Leu Tyr Glu Ser Lys Cys Arg
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(14)
<223> OTHER INFORMATION: Modified linkage between residues
<220> FEATURE:
<223> OTHER INFORMATION: see specification as filed for detailed
      description of substitutions and preferred embodiments

<400> SEQUENCE: 60

Cys Ile Lys Phe Thr Asn Gly Leu Leu Tyr Glu Ser Lys Cys Arg
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:

```
<221> NAME/KEY: misc_feature
<222> LOCATION: (1)..(15)
<223> OTHER INFORMATION: Modified linkage between residues
<220> FEATURE:
<223> OTHER INFORMATION: see specification as filed for detailed
      description of substitutions and preferred embodiments

<400> SEQUENCE: 61

Cys Ile Lys Phe Thr Asn Gly Leu Leu Tyr Glu Ser Lys Arg Cys
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (8)..(9)
<223> OTHER INFORMATION: Modified linkage between residues
<220> FEATURE:
<223> OTHER INFORMATION: C-term CONH2
<220> FEATURE:
<223> OTHER INFORMATION: see specification as filed for detailed
      description of substitutions and preferred embodiments

<400> SEQUENCE: 62

Ile Lys Phe Thr Asn Gly Leu Cys Cys Leu Tyr Glu Ser Lys Arg
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (7)..(9)
<223> OTHER INFORMATION: Modified linkage between residues
<220> FEATURE:
<223> OTHER INFORMATION: C-term CONH2
<220> FEATURE:
<223> OTHER INFORMATION: see specification as filed for detailed
      description of substitutions and preferred embodiments

<400> SEQUENCE: 63

Ile Lys Phe Thr Asn Gly Cys Leu Cys Leu Tyr Glu Ser Lys Arg
1               5                   10                  15

<210> SEQ ID NO 64
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (7)..(10)
<223> OTHER INFORMATION: Modified linkage between residues
<220> FEATURE:
<223> OTHER INFORMATION: C-term CONH2
<220> FEATURE:
<223> OTHER INFORMATION: see specification as filed for detailed
      description of substitutions and preferred embodiments

<400> SEQUENCE: 64

Ile Lys Phe Thr Asn Gly Cys Leu Leu Cys Tyr Glu Ser Lys Arg
```

<210> SEQ ID NO 65
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (6)..(10)
<223> OTHER INFORMATION: Modified linkage between residues
<220> FEATURE:
<223> OTHER INFORMATION: C-term CONH2
<220> FEATURE:
<223> OTHER INFORMATION: see specification as filed for detailed
      description of substitutions and preferred embodiments

<400> SEQUENCE: 65

Ile Lys Phe Thr Asn Cys Gly Leu Leu Cys Tyr Glu Ser Lys Arg
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (5)..(10)
<223> OTHER INFORMATION: Modified linkage between residues
<220> FEATURE:
<223> OTHER INFORMATION: C-term CONH2
<220> FEATURE:
<223> OTHER INFORMATION: see specification as filed for detailed
      description of substitutions and preferred embodiments

<400> SEQUENCE: 66

Ile Lys Phe Thr Cys Asn Gly Leu Leu Cys Tyr Glu Ser Lys Arg
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (5)..(11)
<223> OTHER INFORMATION: Modified linkage between residues
<220> FEATURE:
<223> OTHER INFORMATION: C-term CONH2
<220> FEATURE:
<223> OTHER INFORMATION: see specification as filed for detailed
      description of substitutions and preferred embodiments

<400> SEQUENCE: 67

Ile Lys Phe Thr Cys Asn Gly Leu Leu Tyr Cys Glu Ser Lys Arg
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<221> NAME/KEY: misc_feature
<222> LOCATION: (5)..(12)
<223> OTHER INFORMATION: Modified linkage between residues
<220> FEATURE:
<223> OTHER INFORMATION: C-term CONH2
<220> FEATURE:
<223> OTHER INFORMATION: see specification as filed for detailed
      description of substitutions and preferred embodiments

<400> SEQUENCE: 68

Ile Lys Phe Thr Cys Asn Gly Leu Leu Tyr Glu Cys Ser Lys Arg
1               5                   10                  15

<210> SEQ ID NO 69
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (5)..(13)
<223> OTHER INFORMATION: Modified linkage between residues
<220> FEATURE:
<223> OTHER INFORMATION: C-term CONH2
<220> FEATURE:
<223> OTHER INFORMATION: see specification as filed for detailed
      description of substitutions and preferred embodiments

<400> SEQUENCE: 69

Ile Lys Phe Thr Cys Asn Gly Leu Leu Tyr Glu Ser Cys Lys Arg
1               5                   10                  15

<210> SEQ ID NO 70
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (4)..(13)
<223> OTHER INFORMATION: Modified linkage between residues
<220> FEATURE:
<223> OTHER INFORMATION: C-term CONH2
<220> FEATURE:
<223> OTHER INFORMATION: see specification as filed for detailed
      description of substitutions and preferred embodiments

<400> SEQUENCE: 70

Ile Lys Phe Cys Thr Asn Gly Leu Leu Tyr Glu Ser Cys Lys Arg
1               5                   10                  15

<210> SEQ ID NO 71
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (3)..(13)
<223> OTHER INFORMATION: Modified linkage between residues
<220> FEATURE:
<223> OTHER INFORMATION: C-term CONH2
<220> FEATURE:
<223> OTHER INFORMATION: see specification as filed for detailed
      description of substitutions and preferred embodiments
```

```
<400> SEQUENCE: 71

Ile Lys Cys Phe Thr Asn Gly Leu Leu Tyr Glu Ser Cys Lys Arg
1               5                   10                  15

<210> SEQ ID NO 72
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (3)..(14)
<223> OTHER INFORMATION: Modified linkage between residues
<220> FEATURE:
<223> OTHER INFORMATION: C-term CONH2
<220> FEATURE:
<223> OTHER INFORMATION: see specification as filed for detailed
      description of substitutions and preferred embodiments

<400> SEQUENCE: 72

Ile Lys Cys Phe Thr Asn Gly Leu Leu Tyr Glu Ser Lys Cys Arg
1               5                   10                  15

<210> SEQ ID NO 73
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(14)
<223> OTHER INFORMATION: Modified linkage between residues
<220> FEATURE:
<223> OTHER INFORMATION: C-term CONH2
<220> FEATURE:
<223> OTHER INFORMATION: see specification as filed for detailed
      description of substitutions and preferred embodiments

<400> SEQUENCE: 73

Ile Cys Lys Phe Thr Asn Gly Leu Leu Tyr Glu Ser Lys Cys Arg
1               5                   10                  15

<210> SEQ ID NO 74
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(14)
<223> OTHER INFORMATION: Modified linkage between residues
<220> FEATURE:
<223> OTHER INFORMATION: C-term CONH2
<220> FEATURE:
<223> OTHER INFORMATION: see specification as filed for detailed
      description of substitutions and preferred embodiments

<400> SEQUENCE: 74

Cys Ile Lys Phe Thr Asn Gly Leu Leu Tyr Glu Ser Lys Cys Arg
1               5                   10                  15

<210> SEQ ID NO 75
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: misc_feature
<222> LOCATION: (1)..(15)
<223> OTHER INFORMATION: Modified linkage between residues
<220> FEATURE:
<223> OTHER INFORMATION: C-term CONH2
<220> FEATURE:
<223> OTHER INFORMATION: see specification as filed for detailed
      description of substitutions and preferred embodiments

<400> SEQUENCE: 75

Cys Ile Lys Phe Thr Asn Gly Leu Leu Tyr Glu Ser Lys Arg Cys
1               5                   10                  15

<210> SEQ ID NO 76
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gamma-Glu
<220> FEATURE:
<221> NAME/KEY: MOD_RES
<222> LOCATION: (4)..(4)
<223> OTHER INFORMATION: Gly, Leu, His, Lys or Pro
<220> FEATURE:
<223> OTHER INFORMATION: C-term CONH2

<400> SEQUENCE: 76

Glu Cys Gly Xaa Leu Leu
1               5

<210> SEQ ID NO 77
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gamma-Glu
<220> FEATURE:
<221> NAME/KEY: MOD_RES
<222> LOCATION: (2)..(2)
<223> OTHER INFORMATION: Modified Cys for cross-linking
<220> FEATURE:
<221> NAME/KEY: MOD_RES
<222> LOCATION: (4)..(4)
<223> OTHER INFORMATION: Gly, Leu, His, Lys or Pro
<220> FEATURE:
<223> OTHER INFORMATION: C-term CONH2
<220> FEATURE:
<223> OTHER INFORMATION: see specification as filed for detailed
      description of substitutions and preferred embodiments

<400> SEQUENCE: 77

Glu Cys Gly Xaa Leu Leu
1               5

<210> SEQ ID NO 78
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gamma-Glu
<220> FEATURE:
<221> NAME/KEY: MOD_RES
<222> LOCATION: (7)..(7)
<223> OTHER INFORMATION: Modified Cys for cross-linking
<220> FEATURE:
<223> OTHER INFORMATION: C-term CONH2
<220> FEATURE:
<223> OTHER INFORMATION: see specification as filed for detailed
      description of substitutions and preferred embodiments

<400> SEQUENCE: 78

Glu Cys Gly Arg Gly Asp Cys
1               5

<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gamma-Glu
<220> FEATURE:
<221> NAME/KEY: misc_feature
<222> LOCATION: (2)..(7)
<223> OTHER INFORMATION: Modified linkage between residues
<220> FEATURE:
<223> OTHER INFORMATION: C-term CONH2
<220> FEATURE:
<223> OTHER INFORMATION: see specification as filed for detailed
      description of substitutions and preferred embodiments

<400> SEQUENCE: 79

Glu Cys Gly Arg Gly Asp Cys
1               5

<210> SEQ ID NO 80
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Modified Cys for cross-linking
<220> FEATURE:
<223> OTHER INFORMATION: C-term CONH2
<220> FEATURE:
<223> OTHER INFORMATION: see specification as filed for detailed
      description of substitutions and preferred embodiments

<400> SEQUENCE: 80

Val Thr Leu Pro Ser Thr Cys Gly Ala Ser
1               5                   10

<210> SEQ ID NO 81
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (7)..(7)
<223> OTHER INFORMATION: Modified Cys for cross-linking
<220> FEATURE:
<223> OTHER INFORMATION: C-term CONH2
<220> FEATURE:
<223> OTHER INFORMATION: see specification as filed for detailed
      description of substitutions and preferred embodiments

<400> SEQUENCE: 81

Val Thr Leu Pro Ser Thr Cys Gly Ala Ser
1               5                   10

<210> SEQ ID NO 82
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gamma-Glu

<400> SEQUENCE: 82

Glu Cys Gly Gly Leu Leu
1               5

<210> SEQ ID NO 83
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gamma-Glu

<400> SEQUENCE: 83

Glu Cys Gly Leu Leu Leu
1               5

<210> SEQ ID NO 84
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gamma-Glu

<400> SEQUENCE: 84

Glu Cys Gly His Leu Leu
1               5

<210> SEQ ID NO 85
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(1)
<223> OTHER INFORMATION: Gamma-Glu

<400> SEQUENCE: 85

Glu Cys Gly Lys Leu Leu
1               5

<210> SEQ ID NO 86
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gamma-Glu

<400> SEQUENCE: 86

Glu Cys Gly Pro Leu Leu
1               5

<210> SEQ ID NO 87
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gamma-Glu

<400> SEQUENCE: 87

Glu Cys Gly Gly Gly Leu Leu
1               5

<210> SEQ ID NO 88
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Glu Cys Gly Gly Leu Leu
1               5

<210> SEQ ID NO 89
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Glu Cys Gly Gly Leu Leu
1               5

<210> SEQ ID NO 90
<211> LENGTH: 6
<212> TYPE: PRT
<213> ORGANISM: Artificial Sequence
<220> FEATURE:
<223> OTHER INFORMATION: Description of Artificial Sequence: Synthetic
```

-continued

```
      peptide

<400> SEQUENCE: 90

Asp Cys Gly Gly Leu Leu
1               5

<210> SEQ ID NO 91
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Asn Cys Gly Gly Leu Leu
1               5

<210> SEQ ID NO 92
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gln Cys Gly Gly Leu Leu
1               5

<210> SEQ ID NO 93
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gamma-Glu

<400> SEQUENCE: 93

Gly Glu Cys Gly Gly Gly Leu Leu
1               5

<210> SEQ ID NO 94
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gamma-Glu

<400> SEQUENCE: 94

Glu Cys Gly Cys
1

<210> SEQ ID NO 95
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(1)
<223> OTHER INFORMATION: Gamma-Glu
<220> FEATURE:
<221> NAME/KEY: MOD_RES
<222> LOCATION: (2)..(2)
<223> OTHER INFORMATION: Modified Cys for cross-linking
<220> FEATURE:
<223> OTHER INFORMATION: see specification as filed for detailed
      description of substitutions and preferred embodiments

<400> SEQUENCE: 95

Glu Cys Gly Cys
1

<210> SEQ ID NO 96
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gamma-Glu
<220> FEATURE:
<221> NAME/KEY: MOD_RES
<222> LOCATION: (2)..(2)
<223> OTHER INFORMATION: Modified Cys for cross-linking
<220> FEATURE:
<221> NAME/KEY: MOD_RES
<222> LOCATION: (4)..(4)
<223> OTHER INFORMATION: Modified Cys for cross-linking
<220> FEATURE:
<223> OTHER INFORMATION: see specification as filed for detailed
      description of substitutions and preferred embodiments

<400> SEQUENCE: 96

Glu Cys Gly Cys
1

<210> SEQ ID NO 97
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (8)..(9)
<223> OTHER INFORMATION: Modified linkage between residues
<220> FEATURE:
<223> OTHER INFORMATION: see specification as filed for detailed
      description of substitutions and preferred embodiments

<400> SEQUENCE: 97

Ile Lys Phe Thr Asn Gly Leu Cys Cys Leu Tyr Glu Ser Lys Arg
1               5                   10                  15

<210> SEQ ID NO 98
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (7)..(9)
<223> OTHER INFORMATION: Modified linkage between residues
```

```
<220> FEATURE:
<223> OTHER INFORMATION: see specification as filed for detailed
      description of substitutions and preferred embodiments

<400> SEQUENCE: 98

Ile Lys Phe Thr Asn Gly Cys Leu Cys Leu Tyr Glu Ser Lys Arg
1               5                   10                  15

<210> SEQ ID NO 99
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (7)..(10)
<223> OTHER INFORMATION: Modified linkage between residues
<220> FEATURE:
<223> OTHER INFORMATION: see specification as filed for detailed
      description of substitutions and preferred embodiments

<400> SEQUENCE: 99

Ile Lys Phe Thr Asn Gly Cys Leu Leu Cys Tyr Glu Ser Lys Arg
1               5                   10                  15

<210> SEQ ID NO 100
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (6)..(10)
<223> OTHER INFORMATION: Modified linkage between residues
<220> FEATURE:
<223> OTHER INFORMATION: see specification as filed for detailed
      description of substitutions and preferred embodiments

<400> SEQUENCE: 100

Ile Lys Phe Thr Asn Cys Gly Leu Leu Cys Tyr Glu Ser Lys Arg
1               5                   10                  15

<210> SEQ ID NO 101
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (5)..(10)
<223> OTHER INFORMATION: Modified linkage between residues
<220> FEATURE:
<223> OTHER INFORMATION: see specification as filed for detailed
      description of substitutions and preferred embodiments

<400> SEQUENCE: 101

Ile Lys Phe Thr Cys Asn Gly Leu Leu Cys Tyr Glu Ser Lys Arg
1               5                   10                  15

<210> SEQ ID NO 102
<211> LENGTH: 15
<212> TYPE: PRT
<213> ORGANISM: Artificial Sequence
<220> FEATURE:
<223> OTHER INFORMATION: Description of Artificial Sequence: Synthetic
```

```
                      peptide
<220> FEATURE:
<221> NAME/KEY: misc_feature
<222> LOCATION: (5)..(11)
<223> OTHER INFORMATION: Modified linkage between residues
<220> FEATURE:
<223> OTHER INFORMATION: see specification as filed for detailed
      description of substitutions and preferred embodiments

<400> SEQUENCE: 102

Ile Lys Phe Thr Cys Asn Gly Leu Leu Tyr Cys Glu Ser Lys Arg
1               5                   10                  15

<210> SEQ ID NO 103
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (5)..(12)
<223> OTHER INFORMATION: Modified linkage between residues
<220> FEATURE:
<223> OTHER INFORMATION: see specification as filed for detailed
      description of substitutions and preferred embodiments

<400> SEQUENCE: 103

Ile Lys Phe Thr Cys Asn Gly Leu Leu Tyr Glu Cys Ser Lys Arg
1               5                   10                  15

<210> SEQ ID NO 104
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (5)..(13)
<223> OTHER INFORMATION: Modified linkage between residues
<220> FEATURE:
<223> OTHER INFORMATION: see specification as filed for detailed
      description of substitutions and preferred embodiments

<400> SEQUENCE: 104

Ile Lys Phe Thr Cys Asn Gly Leu Leu Tyr Glu Ser Cys Lys Arg
1               5                   10                  15

<210> SEQ ID NO 105
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (4)..(13)
<223> OTHER INFORMATION: Modified linkage between residues
<220> FEATURE:
<223> OTHER INFORMATION: see specification as filed for detailed
      description of substitutions and preferred embodiments

<400> SEQUENCE: 105

Ile Lys Phe Cys Thr Asn Gly Leu Leu Tyr Glu Ser Cys Lys Arg
1               5                   10                  15

<210> SEQ ID NO 106
```

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (3)..(13)
<223> OTHER INFORMATION: Modified linkage between residues
<220> FEATURE:
<223> OTHER INFORMATION: see specification as filed for detailed
      description of substitutions and preferred embodiments

<400> SEQUENCE: 106

Ile Lys Cys Phe Thr Asn Gly Leu Leu Tyr Glu Ser Cys Lys Arg
1               5                   10                  15

<210> SEQ ID NO 107
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (3)..(14)
<223> OTHER INFORMATION: Modified linkage between residues
<220> FEATURE:
<223> OTHER INFORMATION: see specification as filed for detailed
      description of substitutions and preferred embodiments

<400> SEQUENCE: 107

Ile Lys Cys Phe Thr Asn Gly Leu Leu Tyr Glu Ser Lys Cys Arg
1               5                   10                  15

<210> SEQ ID NO 108
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(14)
<223> OTHER INFORMATION: Modified linkage between residues
<220> FEATURE:
<223> OTHER INFORMATION: see specification as filed for detailed
      description of substitutions and preferred embodiments

<400> SEQUENCE: 108

Ile Cys Lys Phe Thr Asn Gly Leu Leu Tyr Glu Ser Lys Cys Arg
1               5                   10                  15

<210> SEQ ID NO 109
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(14)
<223> OTHER INFORMATION: Modified linkage between residues
<220> FEATURE:
<223> OTHER INFORMATION: see specification as filed for detailed
      description of substitutions and preferred embodiments

<400> SEQUENCE: 109
```

Cys Ile Lys Phe Thr Asn Gly Leu Leu Tyr Glu Ser Lys Cys Arg
1               5                   10                  15

<210> SEQ ID NO 110
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(15)
<223> OTHER INFORMATION: Modified linkage between residues
<220> FEATURE:
<223> OTHER INFORMATION: see specification as filed for detailed
      description of substitutions and preferred embodiments

<400> SEQUENCE: 110

Cys Ile Lys Phe Thr Asn Gly Leu Leu Tyr Glu Ser Lys Arg Cys
1               5                   10                  15

<210> SEQ ID NO 111
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Phe-CF3
<220> FEATURE:
<221> NAME/KEY: misc_feature
<222> LOCATION: (5)..(9)
<223> OTHER INFORMATION: Possible modified linkage between residues
<220> FEATURE:
<223> OTHER INFORMATION: see specification as filed for detailed
      description of substitutions and preferred embodiments

<400> SEQUENCE: 111

Thr Ala Trp Tyr Cys Asn Phe Glu Cys Leu Leu Arg
1               5                   10

<210> SEQ ID NO 112
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Perfluorophenyl-modified phenylalanine
<220> FEATURE:
<223> OTHER INFORMATION: C-term CONH2

<400> SEQUENCE: 112

Ile Thr Pro Cys Asn Leu Leu Phe Tyr Tyr Gly Lys Lys Lys
1               5                   10

<210> SEQ ID NO 113
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term CONH2

```
<400> SEQUENCE: 113

Val Thr Leu Pro Ser Thr Cys Gly Ala Ser
1               5                   10

<210> SEQ ID NO 114
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gamma-Glu
<220> FEATURE:
<223> OTHER INFORMATION: C-term CONH2

<400> SEQUENCE: 114

Glu Cys Gly Gly Leu Leu
1               5

<210> SEQ ID NO 115
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gamma-Glu
<220> FEATURE:
<223> OTHER INFORMATION: C-term CONH2

<400> SEQUENCE: 115

Glu Cys Gly Leu Leu Leu
1               5

<210> SEQ ID NO 116
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gamma-Glu
<220> FEATURE:
<223> OTHER INFORMATION: C-term CONH2

<400> SEQUENCE: 116

Glu Cys Gly His Leu Leu
1               5

<210> SEQ ID NO 117
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gamma-Glu
<220> FEATURE:
```

<223> OTHER INFORMATION: C-term CONH2

<400> SEQUENCE: 117

Glu Cys Gly Lys Leu Leu
1               5

<210> SEQ ID NO 118
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gamma-Glu
<220> FEATURE:
<223> OTHER INFORMATION: C-term CONH2

<400> SEQUENCE: 118

Glu Cys Gly Pro Leu Leu
1               5

<210> SEQ ID NO 119
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gamma-Glu
<220> FEATURE:
<223> OTHER INFORMATION: C-term CONH2

<400> SEQUENCE: 119

Glu Cys Gly Gly Gly Leu Leu
1               5

<210> SEQ ID NO 120
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term CONH2

<400> SEQUENCE: 120

Glu Cys Gly Gly Leu Leu
1               5

<210> SEQ ID NO 121
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term CONH2

<400> SEQUENCE: 121

Asp Cys Gly Gly Leu Leu
1               5

```
<210> SEQ ID NO 122
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gamma-Glu
<220> FEATURE:
<223> OTHER INFORMATION: C-term CONHNH2

<400> SEQUENCE: 122

Glu Cys Gly Gly Ala Leu Phe
1               5

<210> SEQ ID NO 123
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gamma-Glu
<220> FEATURE:
<221> NAME/KEY: MOD_RES
<222> LOCATION: (2)..(2)
<223> OTHER INFORMATION: Cys(S-tBu)
<220> FEATURE:
<223> OTHER INFORMATION: C-term CONH2

<400> SEQUENCE: 123

Glu Cys Gly Arg Gly Asp Cys
1               5

<210> SEQ ID NO 124
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gamma-Glu
<220> FEATURE:
<223> OTHER INFORMATION: C-term CONH2

<400> SEQUENCE: 124

Glu Cys Gly Gly Pro Thr Ala Ala Lys Glu Ser Cys Leu Leu
1               5                   10

<210> SEQ ID NO 125
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gamma-Glu
<220> FEATURE:
<221> NAME/KEY: MOD_RES
<222> LOCATION: (12)..(12)
```

```
<223> OTHER INFORMATION: Cys(S-tBu)
<220> FEATURE:
<223> OTHER INFORMATION: C-term CONH2

<400> SEQUENCE: 125

Glu Cys Gly Gly Pro Thr Ala Ala Lys Glu Ser Cys Leu Leu
1               5                   10

<210> SEQ ID NO 126
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gamma-Glu
<220> FEATURE:
<221> NAME/KEY: MOD_RES
<222> LOCATION: (2)..(2)
<223> OTHER INFORMATION: Modified Cys for cross-linking
<220> FEATURE:
<223> OTHER INFORMATION: C-term CONH2
<220> FEATURE:
<223> OTHER INFORMATION: see specification as filed for detailed
      description of substitutions and preferred embodiments

<400> SEQUENCE: 126

Glu Cys Gly Arg Gly Asp Cys
1               5

<210> SEQ ID NO 127
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gamma-Glu
<220> FEATURE:
<221> NAME/KEY: MOD_RES
<222> LOCATION: (2)..(2)
<223> OTHER INFORMATION: Modified Cys for cross-linking
<220> FEATURE:
<221> NAME/KEY: MOD_RES
<222> LOCATION: (7)..(7)
<223> OTHER INFORMATION: Modified Cys for cross-linking
<220> FEATURE:
<223> OTHER INFORMATION: C-term CONH2
<220> FEATURE:
<223> OTHER INFORMATION: see specification as filed for detailed
      description of substitutions and preferred embodiments

<400> SEQUENCE: 127

Glu Cys Gly Arg Gly Asp Cys
1               5

<210> SEQ ID NO 128
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gamma-Glu
```

```
<220> FEATURE:
<221> NAME/KEY: MOD_RES
<222> LOCATION: (2)..(2)
<223> OTHER INFORMATION: Modified Cys for cross-linking
<220> FEATURE:
<223> OTHER INFORMATION: C-term CONH2
<220> FEATURE:
<223> OTHER INFORMATION: see specification as filed for detailed
      description of substitutions and preferred embodiments

<400> SEQUENCE: 128

Glu Cys Gly Gly Leu Leu
1               5

<210> SEQ ID NO 129
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gamma-Glu
<220> FEATURE:
<221> NAME/KEY: MOD_RES
<222> LOCATION: (2)..(2)
<223> OTHER INFORMATION: Modified Cys for cross-linking
<220> FEATURE:
<223> OTHER INFORMATION: C-term CONH2
<220> FEATURE:
<223> OTHER INFORMATION: see specification as filed for detailed
      description of substitutions and preferred embodiments

<400> SEQUENCE: 129

Glu Cys Gly Gly Leu Leu
1               5

<210> SEQ ID NO 130
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gamma-Glu
<220> FEATURE:
<221> NAME/KEY: MOD_RES
<222> LOCATION: (2)..(2)
<223> OTHER INFORMATION: Modified Cys for cross-linking
<220> FEATURE:
<223> OTHER INFORMATION: C-term CONHNH2
<220> FEATURE:
<223> OTHER INFORMATION: see specification as filed for detailed
      description of substitutions and preferred embodiments

<400> SEQUENCE: 130

Glu Cys Gly Gly Ala Leu Phe
1               5

<210> SEQ ID NO 131
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(1)
<223> OTHER INFORMATION: Gamma-Glu
<220> FEATURE:
<221> NAME/KEY: MOD_RES
<222> LOCATION: (2)..(2)
<223> OTHER INFORMATION: Modified Cys for cross-linking
<220> FEATURE:
<221> NAME/KEY: MOD_RES
<222> LOCATION: (7)..(7)
<223> OTHER INFORMATION: Modified Phe for cross-linking
<220> FEATURE:
<223> OTHER INFORMATION: see specification as filed for detailed
      description of substitutions and preferred embodiments

<400> SEQUENCE: 131

Glu Cys Gly Gly Ala Leu Phe
1               5

<210> SEQ ID NO 132
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gamma-Glu
<220> FEATURE:
<221> NAME/KEY: MOD_RES
<222> LOCATION: (7)..(7)
<223> OTHER INFORMATION: Modified Cys for cross-linking
<220> FEATURE:
<223> OTHER INFORMATION: C-term CONH2
<220> FEATURE:
<223> OTHER INFORMATION: see specification as filed for detailed
      description of substitutions and preferred embodiments

<400> SEQUENCE: 132

Glu Cys Gly Arg Gly Asp Cys
1               5

<210> SEQ ID NO 133
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glu or Asp
<220> FEATURE:
<223> OTHER INFORMATION: C-term CONH2

<400> SEQUENCE: 133

Xaa Cys Gly Gly Leu Leu
1               5

<210> SEQ ID NO 134
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glu or Asp
<220> FEATURE:
```

```
<221> NAME/KEY: MOD_RES
<222> LOCATION: (2)..(2)
<223> OTHER INFORMATION: Modified Cys for cross-linking
<220> FEATURE:
<223> OTHER INFORMATION: C-term CONH2
<220> FEATURE:
<223> OTHER INFORMATION: see specification as filed for detailed
      description of substitutions and preferred embodiments

<400> SEQUENCE: 134

Xaa Cys Gly Gly Leu Leu
1               5

<210> SEQ ID NO 135
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gamma-Glu
<220> FEATURE:
<221> NAME/KEY: MOD_RES
<222> LOCATION: (2)..(2)
<223> OTHER INFORMATION: Modified Cys for cross-linking
<220> FEATURE:
<221> NAME/KEY: MOD_RES
<222> LOCATION: (9)..(9)
<223> OTHER INFORMATION: Modified Cys for cross-linking
<220> FEATURE:
<223> OTHER INFORMATION: see specification as filed for detailed
      description of substitutions and preferred embodiments

<400> SEQUENCE: 135

Glu Cys Gly Gly Leu Lys Ala Gly Cys
1               5

<210> SEQ ID NO 136
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gamma-Glu
<220> FEATURE:
<221> NAME/KEY: misc_feature
<222> LOCATION: (2)..(9)
<223> OTHER INFORMATION: Modified linkage between residues
<220> FEATURE:
<223> OTHER INFORMATION: see specification as filed for detailed
      description of substitutions and preferred embodiments

<400> SEQUENCE: 136

Glu Cys Gly Gly Leu Lys Ala Gly Cys
1               5

<210> SEQ ID NO 137
```

```
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gamma-Glu
<220> FEATURE:
<221> NAME/KEY: MOD_RES
<222> LOCATION: (2)..(2)
<223> OTHER INFORMATION: Modified Cys for cross-linking
<220> FEATURE:
<221> NAME/KEY: MOD_RES
<222> LOCATION: (14)..(14)
<223> OTHER INFORMATION: Modified Cys for cross-linking
<220> FEATURE:
<223> OTHER INFORMATION: see specification as filed for detailed
      description of substitutions and preferred embodiments

<400> SEQUENCE: 137

Glu Cys Gly Gly Leu Lys Ala Gly Gly Leu Lys Ala Gly Cys
1               5                   10

<210> SEQ ID NO 138
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gamma-Glu
<220> FEATURE:
<221> NAME/KEY: misc_feature
<222> LOCATION: (2)..(14)
<223> OTHER INFORMATION: Modified linkage between residues
<220> FEATURE:
<223> OTHER INFORMATION: see specification as filed for detailed
      description of substitutions and preferred embodiments

<400> SEQUENCE: 138

Glu Cys Gly Gly Leu Lys Ala Gly Gly Leu Lys Ala Gly Cys
1               5                   10

<210> SEQ ID NO 139
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gamma-Glu
<220> FEATURE:
<221> NAME/KEY: MOD_RES
<222> LOCATION: (2)..(2)
<223> OTHER INFORMATION: Modified Cys for cross-linking
<220> FEATURE:
<221> NAME/KEY: MOD_RES
<222> LOCATION: (19)..(19)
<223> OTHER INFORMATION: Modified Cys for cross-linking
```

```
<220> FEATURE:
<223> OTHER INFORMATION: see specification as filed for detailed
      description of substitutions and preferred embodiments

<400> SEQUENCE: 139

Glu Cys Gly Gly Leu Lys Ala Gly Gly Leu Lys Ala Gly Gly Leu Lys
1               5                   10                  15

Ala Gly Cys

<210> SEQ ID NO 140
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gamma-Glu
<220> FEATURE:
<221> NAME/KEY: misc_feature
<222> LOCATION: (2)..(19)
<223> OTHER INFORMATION: Modified linkage between residues
<220> FEATURE:
<223> OTHER INFORMATION: see specification as filed for detailed
      description of substitutions and preferred embodiments

<400> SEQUENCE: 140

Glu Cys Gly Gly Leu Lys Ala Gly Gly Leu Lys Ala Gly Gly Leu Lys
1               5                   10                  15

Ala Gly Cys
```

MODIFICATION OF PEPTIDES VIA $S_NAR$ REACTIONS OF THIOLS WITH FLUORINATED AROMATICS

RELATED APPLICATIONS

This application claims the benefit of priority to U.S. Provisional Patent Application Ser. Nos. 61/821,790, filed May 10, 2013, and 61/705,747, filed Sep. 26, 2012, the contents of both of which are hereby incorporated by reference.

GOVERNMENT SUPPORT

This invention was made with Government support under Grant Nos. GM046059 and GM101762 awarded by the National Institutes of Health. The government has certain rights in this invention.

SEQUENCE LISTING

The instant application contains a Sequence Listing which has been submitted electronically in ASCII format and is hereby incorporated by reference in its entirety. Said ASCII copy, created on Nov. 6, 2013, is named MTV-133.25_SL.txt and is 65,650 bytes in size.

BACKGROUND

For many years, researchers in the field of bioconjugate chemistry have needed well-defined ligation strategies that can be used for the at-will modification of biomolecules. Efficient bioconjugation strategies generally involve high levels of functional group tolerance, compatibility with water and other solvents, and efficient conversions (e.g., fast reaction times and high yields). Reactions that adhere to the principles of "click chemistry" (introduced by Sharpless and co-workers in 2001) are ideal candidates for bioconjugation applications. "Click" reactions are thermodynamically driven because the products have a highly favorable enthalpy of bonds. Several reactions can be classified as "click", including copper-catalyzed Huisgen's dipolar cycloaddition of azides and terminal alkynes, addition of thiols to alkenes, addition of isothiocyanates to amines, and Diels-Alder cycloadditions. Importantly, because the starting materials for these reactions are relatively stable, in principle, they could be introduced to a wide range of macromolecules and hybrid materials. Furthermore, these reactions do not generate any by-products and operate on reasonable timescales (<12 hours), making them attractive for use in bioconjugation.

Biomedical research has benefited tremendously from peptide-based technologies because they have facilitated the elucidation of disease mechanisms and serve as novel and effective therapeutics. Specifically, an emerging theme in biotechnology is to use peptide variants to disrupt protein-protein interactions because compared to small molecules they have a larger surface area for binding, can recognize targets with higher specificity/affinity, and can be generated in weeks by phage display. Despite these successes and advantages, many peptides and most other large and charged biomolecules do not directly cross the cell plasma membrane to reach the cytosol without the aid of supporting transfection agents. Moreover, peptides are rapidly degraded in the biological milieu by proteases rendering them inactive. Identification of a potent p53/MDM2 inhibitor has been one of the central investigations in cancer research, where significant efforts have been undertaken to design small-molecule and peptide species capable of inhibiting this interaction in vivo. Several cell permeable small molecule compounds have been discovered, but they have suffered from serious off target effects and low intracellular activity. The peptide-based inhibitors failed, even the ones designed to penetrate cells, because they cannot enter cells effectively, despite high binding affinity and specificity. Thus a facile and reliable delivery of active and stable peptide-like molecules to the cytosol of cells is desirable.

SUMMARY

In certain embodiments, the invention relates to a compound comprising substructure I:

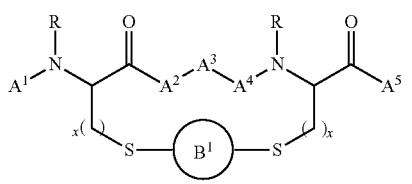

wherein, independently for each occurrence,
$A^1$ is H, an amine protecting group, a natural or unnatural amino acid, a peptide, an oligopeptide, a polypeptide, or a protein;
$A^2$, $A^3$, and $A^4$ are selected from the group consisting of a natural amino acid, an unnatural amino acid, and a plurality of natural amino acids or unnatural amino acids;
$A^5$ is OH, a carboxylate protecting group, a natural or unnatural amino acid, a peptide, an oligopeptide, a polypeptide, or a protein;
x is 0, 1, 2, 3, 4, 5, or 6;

is a perfluorinated aryl para-substituted diradical; and
R is H or alkyl.
In certain embodiments, the invention relates to a compound comprising substructure II:

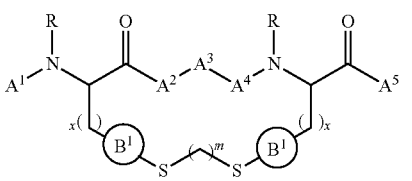

wherein, independently for each occurrence,
$A^1$ is H, an amine protecting group, a natural or unnatural amino acid, a peptide, an oligopeptide, a polypeptide, or a protein;
$A^2$, $A^3$, and $A^4$ are selected from the group consisting of a natural amino acid, an unnatural amino acid, and a plurality of natural amino acids or unnatural amino acids;
$A^5$ is OH, a carboxylate protecting group, a natural or unnatural amino acid, a peptide, an oligopeptide, a polypeptide, or a protein;

is a perfluorinated aryl para-substituted diradical;
m is 1, 2, 3, 4, 5, or 6;
x is 0, 1, 2, 3, 4, 5, or 6; and
R is H or alkyl.

In certain embodiments, the invention relates to a compound comprising substructure VI:

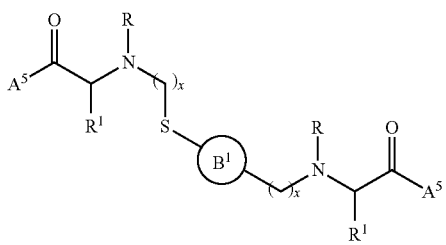

VI wherein, independently for each occurrence,
$A^5$ is OH, a carboxylate protecting group, a natural or unnatural amino acid, a peptide, an oligopeptide, a polypeptide, or a protein;

is a perfluorinated aryl para-substituted diradical;
x is 0, 1, 2, 3, 4, 5, or 6;
R is H or alkyl; and
$R^1$ is H, alkyl, alkylthioalkyl, aralkyl, heteroaralkyl, hydroxyaralkyl, $HO_2C$-alkyl, $H_2N$—C(O)-alkyl, heterocycloalkyl, guanidinylalkyl, aminoalkyl, or hydroxyalkyl.

In certain embodiments, the invention relates to any one of the aforementioned compounds, wherein the compound comprising substructure VI is (SEQ ID NOS 24-25, respectively, in order of appearance)

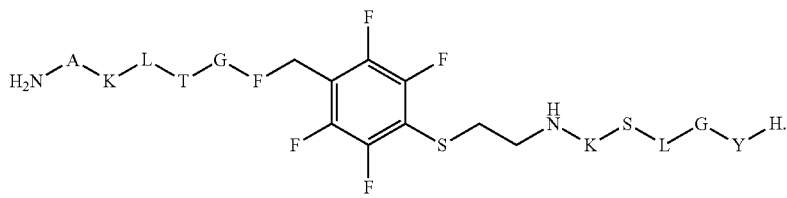

In certain embodiments, the invention relates to a compound comprising substructure VIII:

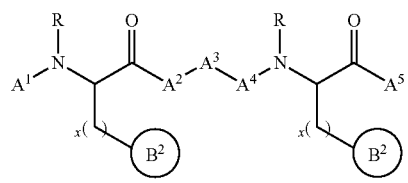

VIII wherein, independently for each occurrence, $A^1$ is H, an amine protecting group, a natural or unnatural amino acid, a peptide, an oligopeptide, a polypeptide, or a protein;
$A^2$, $A^3$, and $A^4$ are selected from the group consisting of a natural amino acid, an unnatural amino acid, and a plurality of natural amino acids or unnatural amino acids;
$A^5$ is OH, a carboxylate protecting group, a natural or unnatural amino acid, a peptide, an oligopeptide, a polypeptide, or a protein;
x is 0, 1, 2, 3, 4, 5, or 6;

is a perfluorinated aryl radical; and
R is H or alkyl.

In certain embodiments, the invention relates to a compound comprising substructure IX:

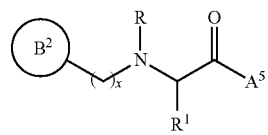

IX wherein, independently for each occurrence,
$A^5$ is OH, a carboxylate protecting group, a natural or unnatural amino acid, a peptide, an oligopeptide, a polypeptide, or a protein;

is a perfluorinated aryl radical;
x is 0, 1, 2, 3, 4, 5, or 6;
R is H or alkyl; and
$R^1$ is H, alkyl, alkylthioalkyl, aralkyl, heteroaralkyl, hydroxyaralkyl, $HO_2C$-alkyl, $H_2N$—C(O)-alkyl, heterocycloalkyl, guanidinylalkyl, aminoalkyl, or hydroxyalkyl.

In certain embodiments, the invention relates to a compound comprising substructure X:

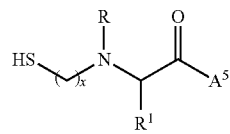

X wherein, independently for each occurrence, $A^5$ is OH, a carboxylate protecting group, a natural or unnatural amino acid, a peptide, an oligopeptide, a polypeptide, or a protein;

x is 0, 1, 2, 3, 4, 5, or 6;

R is H or alkyl; and $R^1$ is H, alkyl, alkylthioalkyl, aralkyl, heteroaralkyl, hydroxyaralkyl, $HO_2C$-alkyl, $H_2N$—C(O)-alkyl, heterocycloalkyl, guanidinylalkyl, aminoalkyl, or hydroxyalkyl.

In certain embodiments, the invention relates to a compound comprising substructure XI or substructure XII:

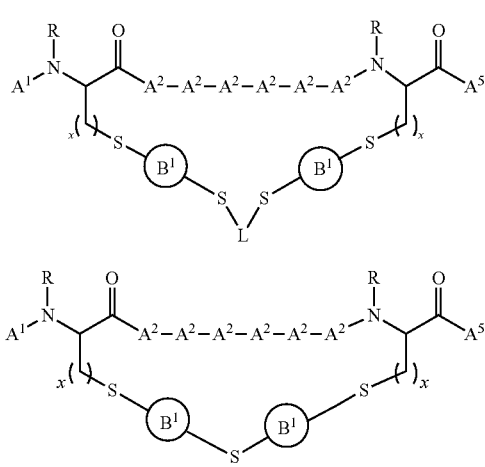

wherein, independently for each occurrence, $A^1$ is H, an amine protecting group, a natural or unnatural amino acid, a peptide, an oligopeptide, a polypeptide, or a protein;

$A^2$ is selected from the group consisting of a natural amino acid, an unnatural amino acid, and a plurality of natural amino acids or unnatural amino acids;

$A^5$ is OH, a carboxylate protecting group, a natural or unnatural amino acid, a peptide, an oligopeptide, a polypeptide, or a protein;

is a perfluorinated aryl para-substituted diradical;

x is 0, 1, 2, 3, 4, 5, or 6;

R is H or alkyl; and

L is a substituted or unsubstituted alkyl diradical, a substituted or unsubstituted aryl diradical, or a substituted or unsubstituted aralkyl diradical.

In certain embodiments, the invention relates to any one of the aforementioned compounds, wherein $A^2$, $A^3$, and $A^4$ are natural or unnatural amino acids.

In certain embodiments, the invention relates to a peptide, an oligopeptide, a polypeptide, or a protein, wherein the peptide, oligopeptides, polypeptide, or protein comprises substructure I, substructure II, substructure III, substructure IV, substructure V, substructure VI, substructure VII, substructure VIII, substructure IX, substructure X, substructure XI, or substructure XII.

In certain embodiments, the invention relates to a peptide, an oligopeptide, a polypeptide, or a protein, wherein the peptide, oligopeptides, polypeptide, or protein comprises a plurality of substructures selected from the group consisting of substructure I, substructure II, substructure III, substructure IV, substructure V, substructure VI, substructure VII, substructure VIII, substructure IX, substructure X, substructure XI, and substructure XII.

In certain embodiments, the invention relates to an affibody comprising substructure I, substructure II, substructure III, substructure IV, substructure V, substructure VI, substructure VII, substructure VIII, substructure IX, substructure X, substructure XI, or substructure XII.

In certain embodiments, the invention relates to an affibody comprising a plurality of substructures selected from the group consisting of substructure I, substructure II, substructure III, substructure IV, substructure V, substructure VI, substructure VII, substructure VIII, substructure IX, substructure X, substructure XI, and substructure XII.

In certain embodiments, the invention relates to a method of making a compound comprising substructure I, according to Scheme 1:

Scheme 1

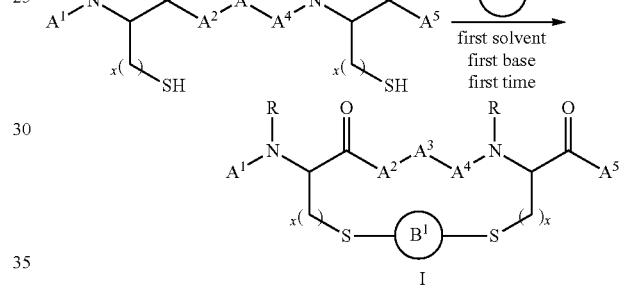

wherein, independently for each occurrence, $A^1$ is H, an amine protecting group, a natural or unnatural amino acid, a peptide, an oligopeptide, a polypeptide, or a protein;

$A^2$, $A^3$, and $A^4$ are selected from the group consisting of a natural amino acid, an unnatural amino acid, and a plurality of natural amino acids or unnatural amino acids;

$A^5$ is OH, a carboxylate protecting group, a natural or unnatural amino acid, a peptide, an oligopeptide, a polypeptide, or a protein;

x is 0, 1, 2, 3, 4, 5, or 6;

R is H or alkyl;

is a perfluorinated aryl compound; and

is a perfluorinated aryl para-substituted diradical.

In certain embodiments, the invention relates to a method of making a compound comprising substructure II, according to Scheme 2:

Scheme 2

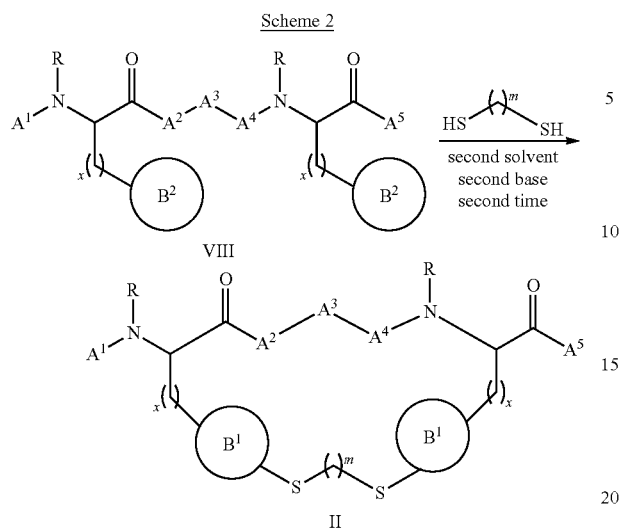

wherein, independently for each occurrence, $A^1$ is H, an amine protecting group, a natural or unnatural amino acid, a peptide, an oligopeptide, a polypeptide, or a protein;

$A^2$, $A^3$, and $A^4$ are selected from the group consisting of a natural amino acid, an unnatural amino acid, and a plurality of natural amino acids or unnatural amino acids;

$A^5$ is OH, a carboxylate protecting group, a natural or unnatural amino acid, a peptide, an oligopeptide, a polypeptide, or a protein;

R is H or alkyl;

x is 0, 1, 2, 3, 4, 5, or 6;

is a perfluorinated aryl radical;

m is 1, 2, 3, 4, 5, or 6; and

is a perfluorinated aryl para-substituted diradical.

In certain embodiments, the invention relates to a method of making a compound comprising substructure VI, according to Scheme 6:

Scheme 6

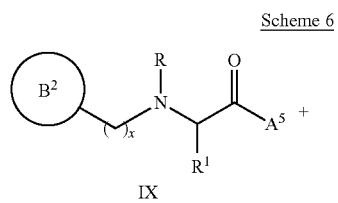

IX

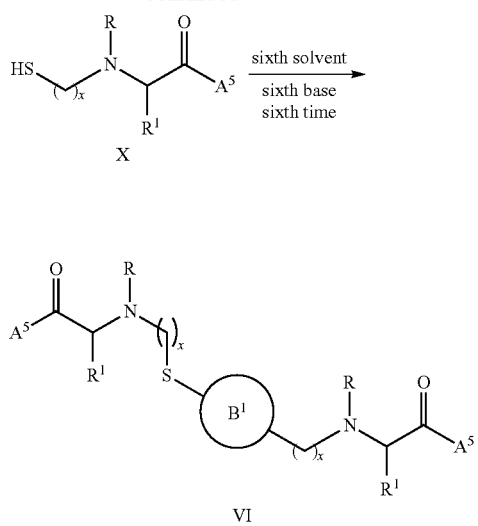

wherein, independently for each occurrence, $A^5$ is OH, a carboxylate protecting group, a natural or unnatural amino acid, a peptide, an oligopeptide, a polypeptide, or a protein;

R is H or alkyl;

x is 0, 1, 2, 3, 4, 5, or 6;

$R^1$ is H, alkyl, alkylthioalkyl, aralkyl, heteroaralkyl, hydroxyaralkyl, $HO_2C$-alkyl, $H_2N$—C(O)-alkyl, heterocycloalkyl, guanidinylalkyl, aminoalkyl, or hydroxyalkyl;

is a perfluorinated aryl radical; and

is a perfluorinated aryl para-substituted diradical.

In certain embodiments, the invention relates to a method of making a compound according to Scheme 7:

Scheme 7

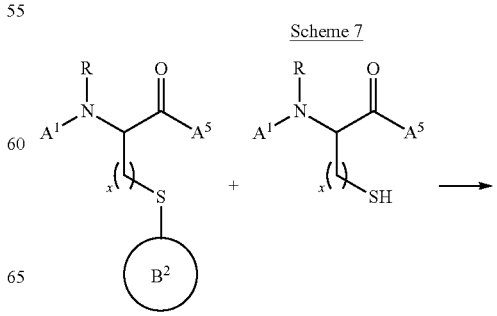

-continued

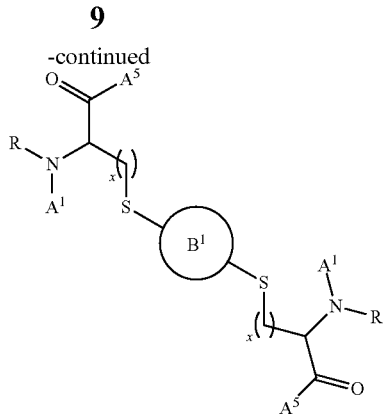

wherein, independently for each occurrence, $A^1$ is H, an amine protecting group, a natural or unnatural amino acid, a peptide, an oligopeptide, a polypeptide, or a protein;

$A^5$ is OH, a carboxylate protecting group, a natural or unnatural amino acid, a peptide, an oligopeptide, a polypeptide, or a protein;

R is H or alkyl;

x is 0, 1, 2, 3, 4, 5, or 6;

is a perfluorinated aryl radical; and

is a perfluorinated aryl para-substituted diradical.

In certain embodiments, the invention relates to a method of disrupting or inhibiting the p53/MDM2 interaction in a cell comprising the step of:

contacting the cell with an effective amount of any one of the aforementioned compounds, thereby disrupting or inhibiting the p53/MDM2 interaction.

In certain embodiments, the invention relates to a method of enhancing the activity of p53 in a cell comprising the step of:

contacting the cell with an effective amount of any one of the aforementioned compounds, thereby enhancing the activity of p53.

In certain embodiments, the invention relates to a method of a disease in a subject in need thereof comprising the step of:

administering to the subject an effective amount of any one of the aforementioned compounds, thereby treating the disease.

BRIEF DESCRIPTION OF THE FIGURES

FIG. 18 depicts the sequence of a target HER2 affibody (SEQ ID NO: 40). N-terminal thioester: VENKFNKEMR-NAYWEIALLPNL-COSR (SEQ ID NO: 2); middle segment mutant: Thz-NQQKRAFIRSLYDDPSG-COSR (SEQ ID NO: 3); and C-terminal segment mutant: Thz-CN-LLCEAKKLNDAQAPK-CONH$_2$ (SEQ ID NO: 4).

FIG. 19 depicts two stapled C-terminal segment mutants of the HER2 affibody. Figure discloses SEQ ID NOS 7 and 13, respectively, in order of appearance.

FIG. 22 depicts (a) the synthetic strategy towards the stapled affibody 10a (figure discloses SEQ ID NOS 41 and 41-42, respectively, in order of appearance), and (b) three peptide segments used in the synthesis of stapled affibodies (figure discloses SEQ ID NOS 2-3 and 43, respectively, in order of appearance).

FIG. 31 depicts various peptide sequences that can be stapled to form compounds of the invention (SEQ ID NOS 48-61, respectively, in order of appearance).

FIG. 33 depicts a full map profiling of staple sites on unprotected peptides (SEQ ID NOS 62-75, respectively, in order of appearance).

FIG. 39 depicts two applications of the GST-catalyzed methods of the invention.

FIG. 43 tabulates the calculated Mulliken atomic charges of different perfluoroaryl-containing molecules.

FIG. 47 tabulates peptides synthesized by Fmoc-SPPS (SEQ ID NOS 112-125, respectively, in order of appearance).

DETAILED DESCRIPTION

Overview

Figure 1:
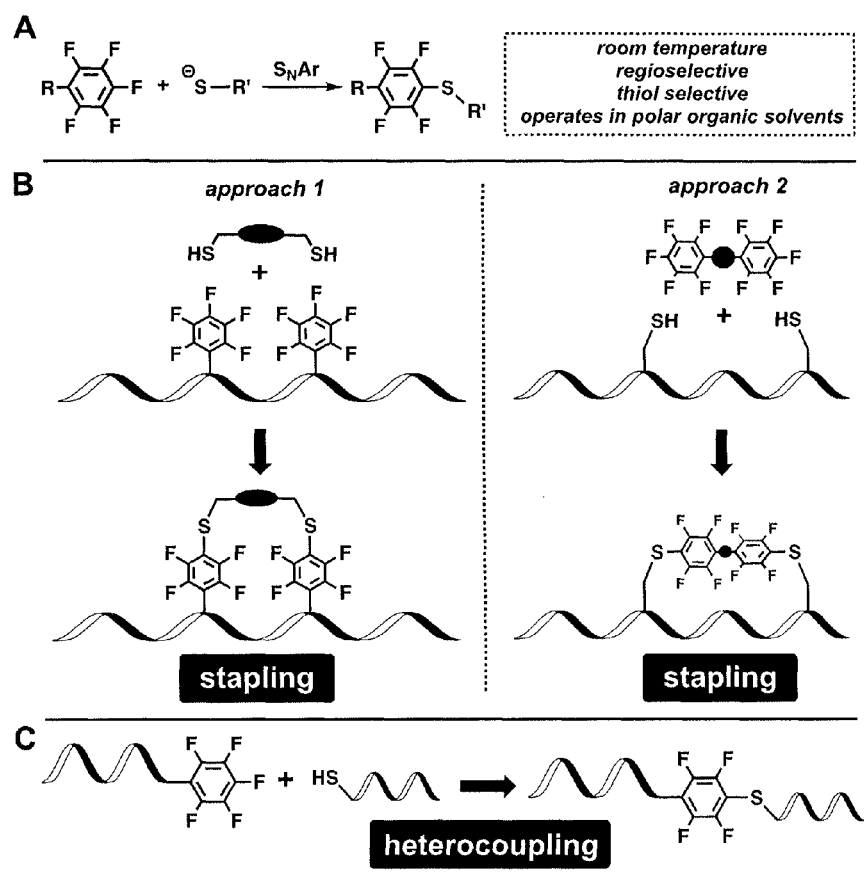
FIG. 1 depicts (A) a general scheme of the $S_NAr$ reaction between thiolate moieties and activated fluoroaromatic species ("fluoroaryl-thiol-click"), (B) two developed peptide stapling strategies, and (C) peptide heterocoupling method based on "fluoroaryl-thiol-click".

In certain embodiments, the invention relates to the discovery and subsequent development of a new chemical transformation for the conjugation of unprotected peptide biomolecules via a $S_NAr$ process between highly fluorinated (activated) aryl moieties and thiols (subsequently referred to as "fluoroaryl-thiol-click" in this text, FIG. 1A). This process features several significant advantages over existing methods of peptide modifications such as specificity towards thiols over other nucleophiles (e.g., amines, hydroxyls), excellent functional group tolerance, mild reaction conditions, and commercial availability of the perfluorinated linkers and amino acids. Specifically, developed conjugation chemistry works in nearly quantitative yields at room temperature in polar solvent media normally used for reactions with cysteine-based peptides (MeCN, DMSO and DMF). The developed method requires only the presence of a relatively benign base, such as phosphate or TRIS, to deprotonate the thiol moiety. While the reaction times normally vary depending on the concentration and chemical identity of the peptide, the reaction conditions usually can be optimized where full conversion is accomplished within 2-6 hours at 1-20 mM concentrations of a starting peptide. In certain embodiments, this method is employed for synthesis of a variety of model "stapled" peptides (FIG. 1B), as well as heterocoupled peptide systems (FIG. 1C). In certain embodiments, this methodology is useful for producing hybrid biomaterials featuring other biomolecules such as DNA, RNA, PNA, proteins, oligosaccharides, and a combination of thereof. In certain embodiments, the hybrid biomaterials are useful for cell penetration and intracellular targeting. In certain embodiments, the invention relates to organic polymer-peptide conjugates, peptides decorated with functional small-molecules (such as fluorescent dye labels), small-molecule drugs, inorganic MRI, radio-contrast agents, and also various functionalized metal-based nanoparticle scaffolds.

Stapling of Unprotected Peptides

Figure 26:
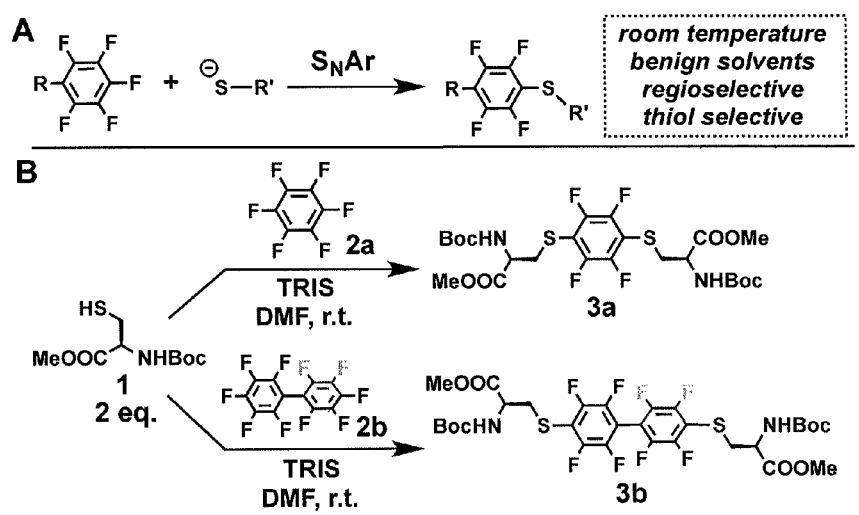
FIG. 26 depicts A) S$_N$Ar reaction between thiolate and a perfluroaromatic species. (B) Model reactions carried out between protected cysteine derivative 1 and two commercially available perfluoroaromatic reagents 2a and 2b. In both cases the reaction yields are >95% as determined by in situ $^{19}$F NMR spectroscopy.

In certain embodiments, the invention relates to optimal conditions for coupling cysteine thiols and perfluorinated substrates using a model system featuring protected amino acid precursors. Reacting protected cysteine 1 with hexafluorobenzene 2a in the presence of base in polar organic solvents for 4.5 hours led to substantial formation of the disubstituted product 3a (FIG. 26), which was isolated via purification on silica gel and characterized via heteronuclear NMR spectroscopy.

Disubstitution (1,4) was observed exclusively in this process, even when hexafluorobenzene was used in excess (10-fold) with 1. Progress of this reaction was monitored by the in situ $^{19}F$ NMR spectroscopy, where the starting material and product exhibited two distinct resonances (δ −138 and −167 ppm, respectively; see FIG. 26). Importantly, no substitution other than 1,4 was observed under these conditions, highlighting the unique regioselectivity of this process. The observed reactivity pattern was previously rationalized by the steric hindrance of the 2,5-(ortho) C—F sites and simultaneous activation of the 4-(para) C—F moiety of the aromatic ring by the thioether moiety formed in the monosubstituted species. The ability of the sulfur to stabilize the negative charge in the intermediate species after the first substitution, ultimately leads to increased rate of a second thiolate substitution thus favoring disubstituted species. Similar reactivity was observed when decafluorobiphenyl species 2b was used instead of 2a (see FIG. 26). We evaluated chemoselectivity of this $S_NAr$ process by screening several amino acids, which could potentially compete with the thiolate as a nucleophile. We observed no reactivity when competing reactions between carboxylate and amine unprotected cysteine analogs of 1, as well as lysine and histidine were used under similar reaction conditions in DMF at room temperature. The unique regio- and chemoselectivity observed in the reactions between perfluoroaromatic molecules 2a and 2b and cysteine 1 thus prompted us to evaluate this chemistry for stapling of unprotected peptides.

Previous studies established chemical transformations for side-chain crosslinking in a polypeptide for residues positioned in an i, i+4 fashion. The resulting peptide structure is commonly referred to as "stapled" motif. Researchers previously showed that "stapled" peptides exhibit different chemical and biological properties than their parent-unstapled surrogates. While a number of well-established approaches for peptide stapling currently exist, we envisioned that cysteine perfluoroarylation may lead to a new class of these species with new properties owing to the rigidity and lipophilicity of the perfluoroaromatic linkers. To test the developed protocol (vide supra) with unprotected peptides, we designed and synthesized two short peptide sequences 4 and 5 that contained cysteine residues separated by 3 amino acids (i, i+4).

Figure 13:
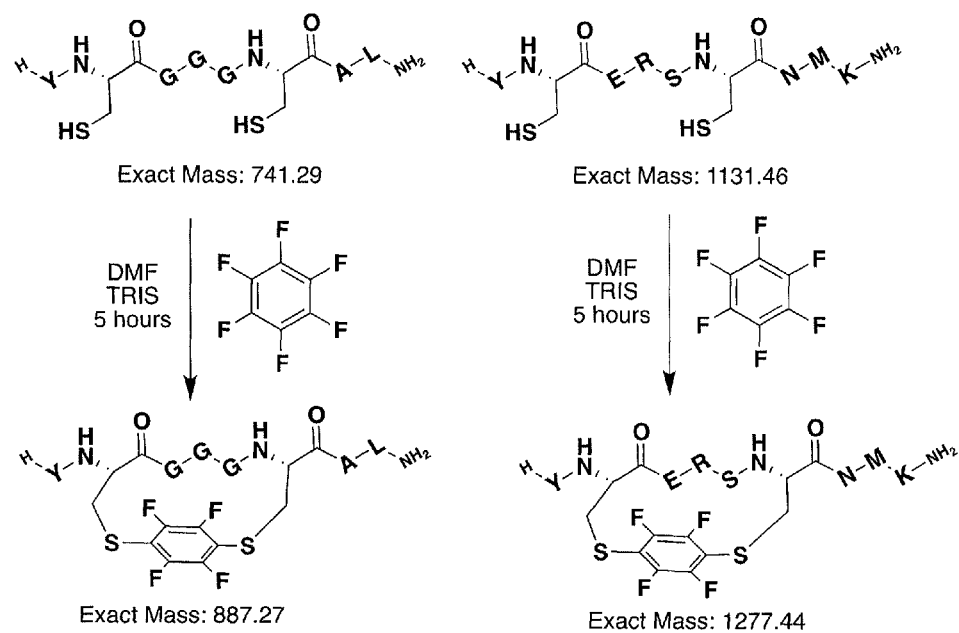
FIG. 13 depicts two peptide "stapling" reaction schemes. In certain embodiments, the concentration of TRIS is about 50 mM, the concentration of hexafluorobenzene is from about 20 mM to about 100 mM, the peptide substrate is present in a concentration of from about 2 mM to about 10 mM, and the reaction takes from about 3 h to about 5 h. In certain embodiments tris(2-carboxyethyl)phosphine (TCEP) is optionally added. Figure discloses SEQ ID NOS 36-37 and 11-12, respectively, in order of appearance.
Figure 14:
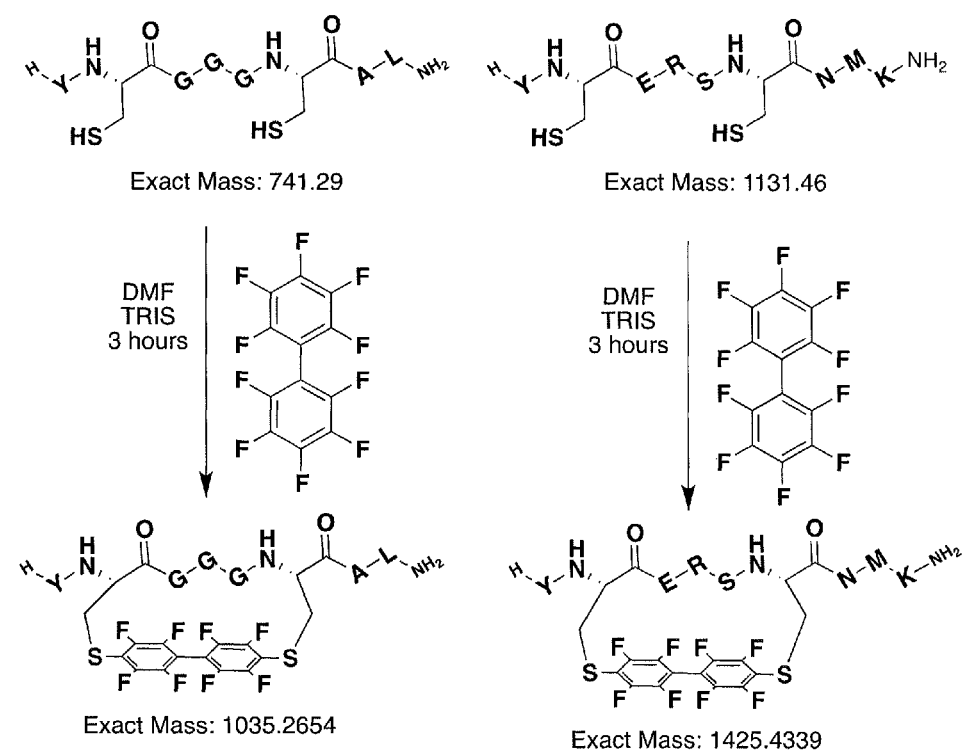
FIG. 14 depicts two peptide "stapling" reaction schemes. In certain embodiments, the concentration of TRIS is about 50 mM, the concentration of decafluorobiphenyl is from about 20 mM to about 100 mM, the peptide substrate is present in a concentration of from about 2 mM to about 10 mM, and the reaction takes from about 3 h to about 5 h. In certain embodiments tris(2-carboxyethyl)phosphine (TCEP) is optionally added. Figure discloses SEQ ID NOS 36-37 and 17-18, respectively, in order of appearance.
Figure 15:
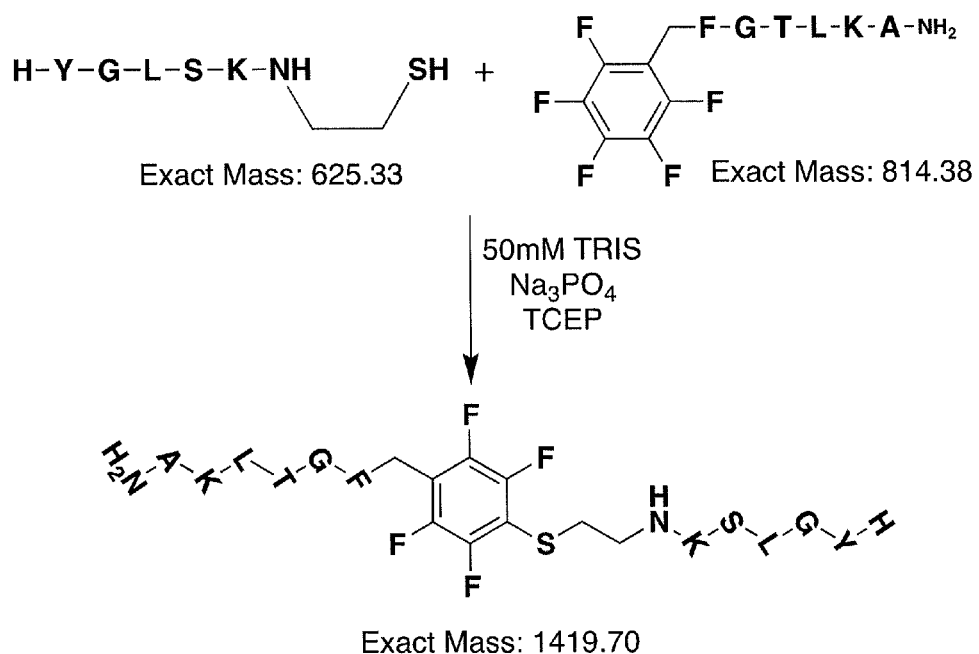
FIG. 15 depicts an example peptide heterocoupling reaction that proceeded to ~60% conversion in 12 h. The reaction conditions were as follows: 0.004 mmol of each peptide, 500 µL of 50 mM TRIS solution, ~5 eq. of TCEP, and ~10 eq. of $Na_3PO_4$. Figure discloses SEQ ID NOS 29, 28 and 24-25, respectively, in order of appearance.
Figure 16:
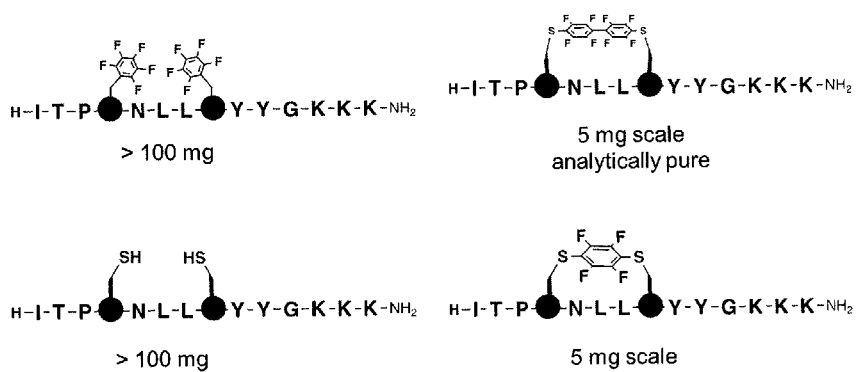
FIG. 16 depicts two peptide precursors and two stapled peptides. Figure discloses SEQ ID NOS 26, 16, 38 and 9, respectively, in order of appearance.
Figure 17:
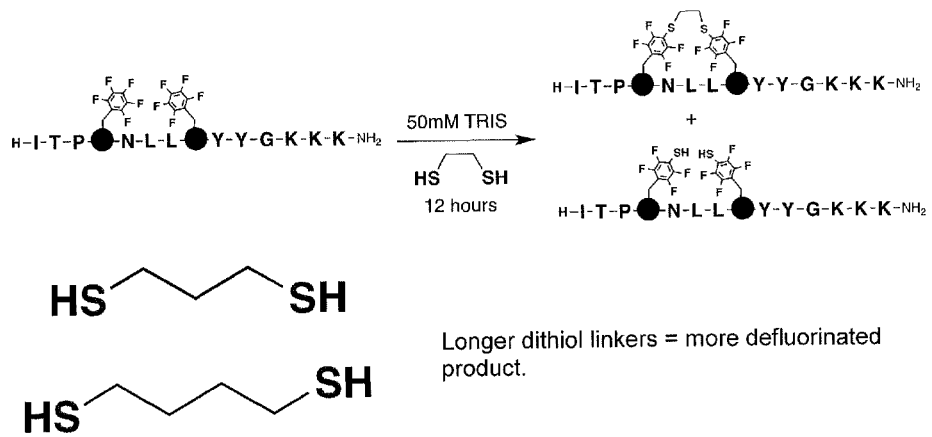
FIG. 17 depicts the stapling of a peptide using dithiol linkers of different lengths. Note: reactions using linkers with >6 carbons give a significant amount of cross-linked peptide. Figure discloses SEQ ID NOS 26, 22 and 39, respectively, in order of appearance.
Figure 20:
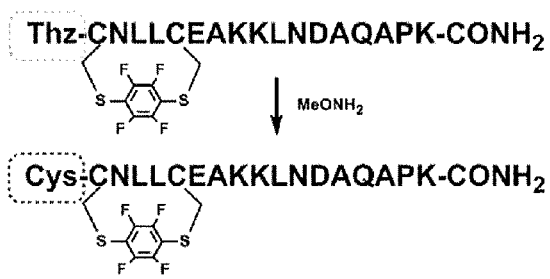
FIG. 20 depicts the modification of a stapled C-terminal segment mutant. Figure discloses SEQ ID NOS 7-8, respectively, in order of appearance.
Figure 21:
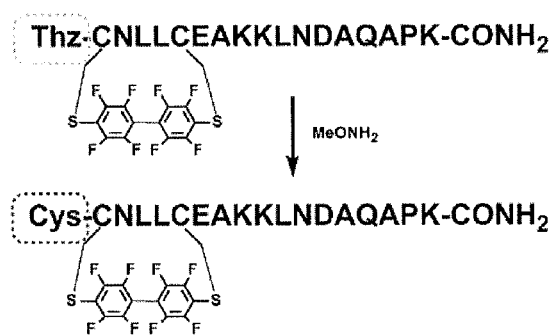
FIG. 21 depicts the modification of a stapled C-terminal segment mutant. Figure discloses SEQ ID NOS 13-14, respectively, in order of appearance.
Figure 23:
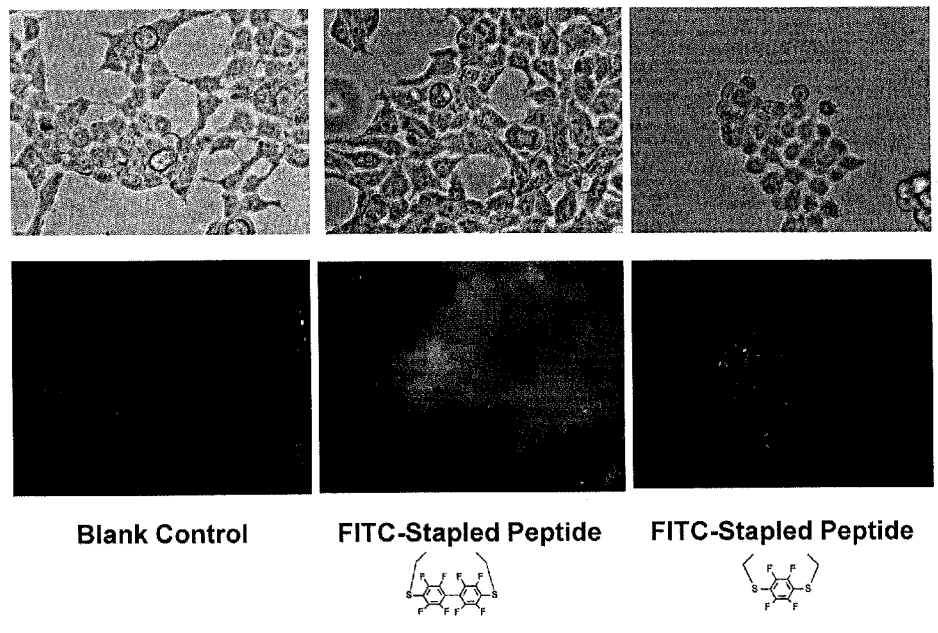
FIG. 23 depicts images of cells with cell-penetrating peptide at 20 µM (left=control, middle=stapled, right=stapled). The peptides were conjugated with a dye.
Figure 24:
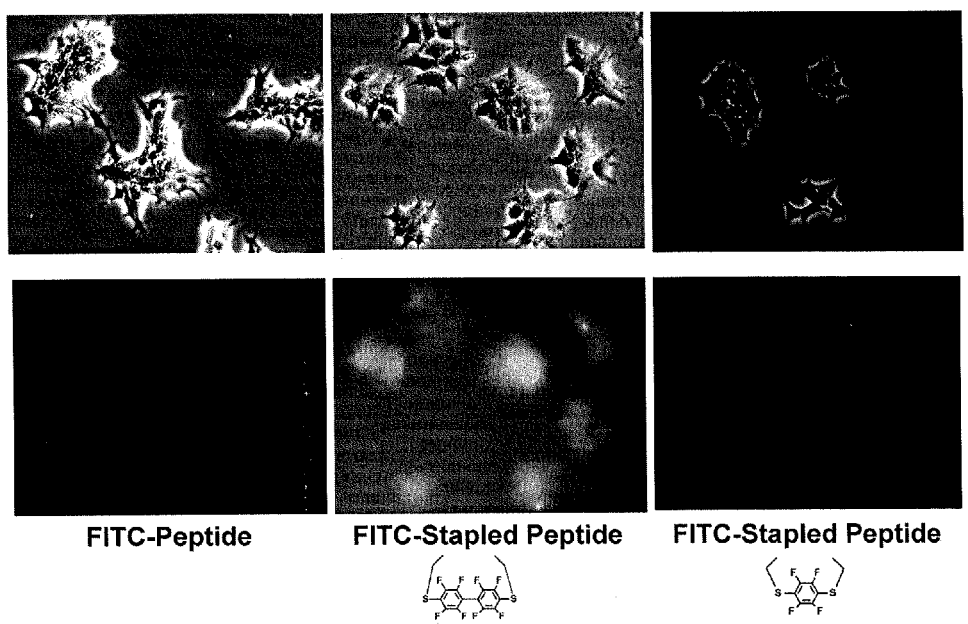
FIG. 24 depicts images of cells with cell-penetrating peptide at 20 µM (left=control, middle=stapled, right=stapled). The peptides were conjugated with a dye.
Figure 25:
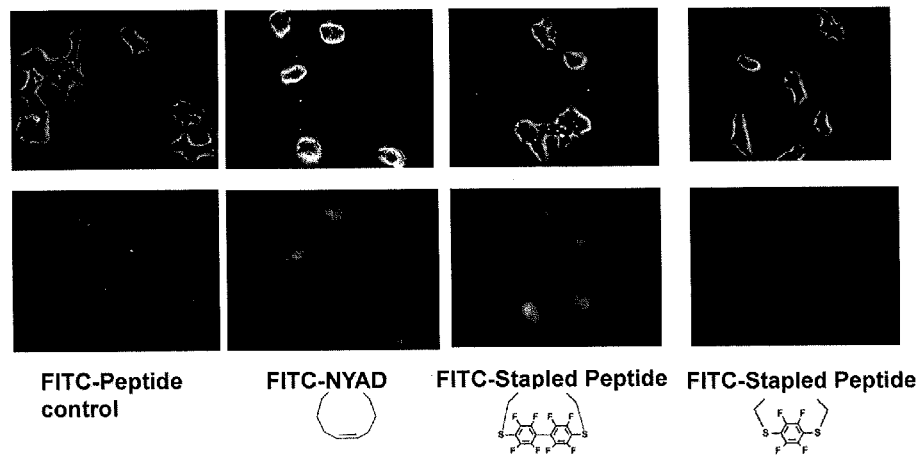
FIG. 25 depicts images of cells with cell-penetrating peptide at 5 µM (left=control, second left=stapled with an alkylene moiety; middle=stapled, right=stapled). The peptides were conjugated with a dye.

By simply incubating unprotected peptide (0.5-2 mM) 4 in the presence of 50 mM solution of TRIS base in DMF for 4.5 hours with either 2a or 2b substrates, significant conversion of the starting material was observed by LC-MS yielding stapled peptides 4a,b (4a is depicted in FIG. 13, bottom left; 4b is depicted in FIG. 14, bottom left). These same experiments were carried out with peptide 5 and similar outcomes were observed. Progress of the reaction and the identity of the products was monitored by LC-MS and in situ $^{19}$F NMR spectroscopy. In both cases, the observed conversions of the starting peptide were greater than 90%.

Figure 27:
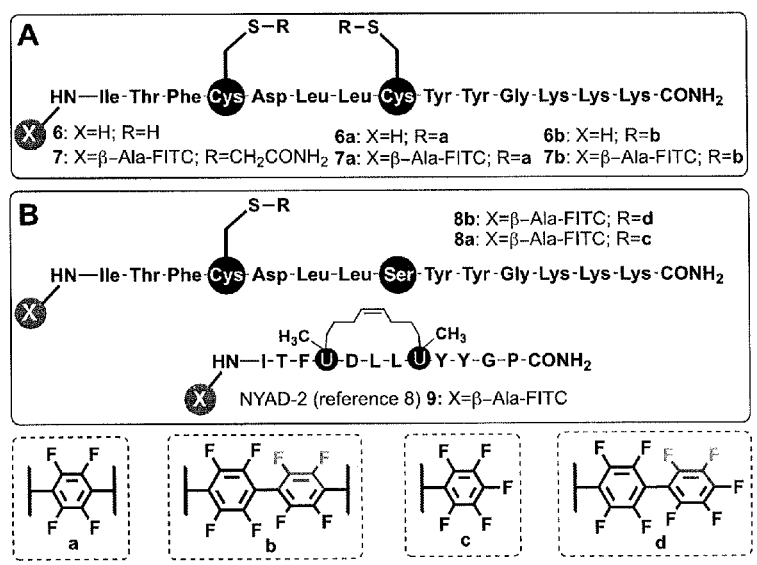
FIG. 27 depicts peptides studied in the context of C-CA model. Figure discloses SEQ ID NOS 44-46, respectively, in order of appearance.

We then decided to evaluate our stapling protocol on more sophisticated peptide sequences to understand how perfluoroaromatic bridges affect the chemical and biological properties of these variants. We thus synthesized a model peptide 6 (FIG. 27) that is capable of binding the C-terminal domain of an HIV-1 capsid assembly polyprotein (C-CA). In particular, previous work showed that stapling of this peptide motif via olefin metathesis efficiently stabilized its α-helical conformation, rendering this peptide more efficient in intracellular uptake and binding ($K_d$~1 µM) to C-CA (FIG. 27).

Figure 28:
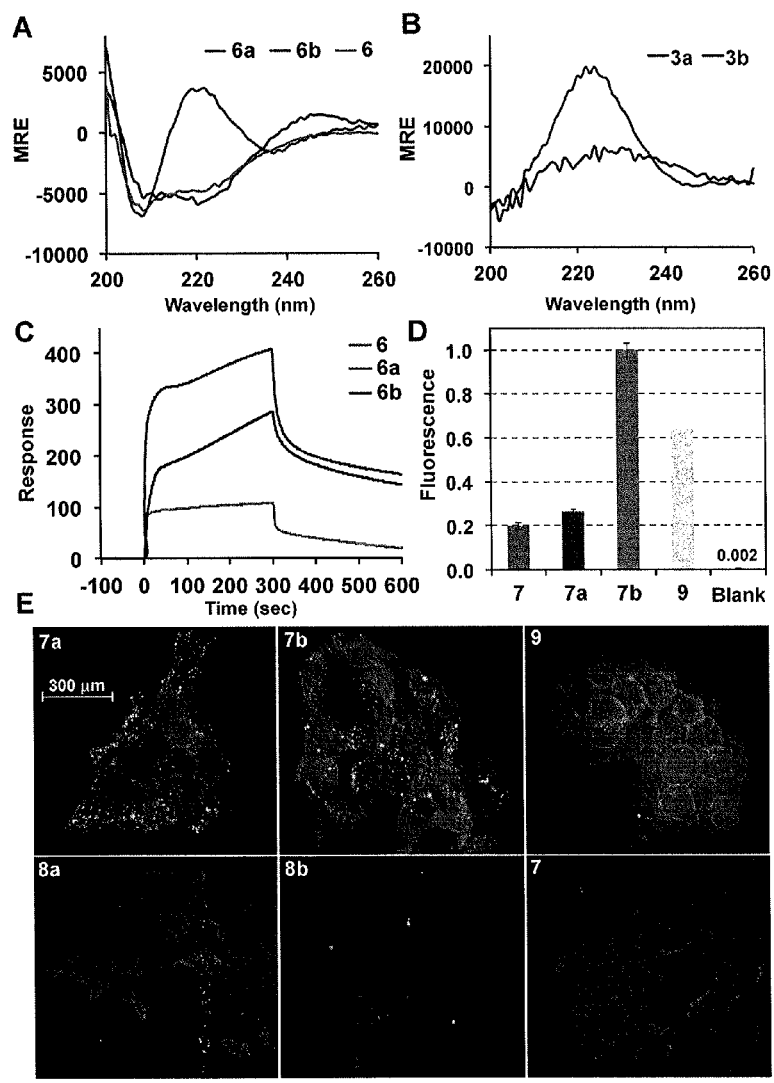
FIG. 28 depicts (A) CD spectra of 6 and 6a,b and (B) of 3a,b; (C) Biacore binding sensograms of 6 and 6a,b with immobilized C-CA (adsorption/desorption time–300 sec); (D) Flow cytometry data for FITC-based peptides incubated with HEK293T cells (25 µM; fluorescence response is normalized to 7b); (E) Z-stack accumulated fluorescent confocal microscopy images of the HEK293T cells treated with peptides 7, 7a-b (5 µM), associated unstapled controls 8a and 8b, and NYAD-2—9.

Our model peptide 6 (FIG. 27A) featuring 14 amino-acid residues with two cysteines positioned in an i, i+4 fashion, was successfully synthesized via Boc/Benzyl in-situ neutralization solid-phase peptide synthesis (SPPS). Peptide 6 was further stapled with 2a and 2b through the developed protocol on a multi-milligram scale, affording the desired peptides in ~70% yield after RP-HPLC purification. Circular dichroism (CD) spectroscopy was used to probe the effect of stapling on the conformational features of the peptides (FIG. 28A). While the CD spectra of 6 and 6b (minima at 208 and 222 nm) showed an α-helical motif, the spectrum of 6a revealed unusual behavior featuring a maxima at 222 nm and a minima at 208 nm (FIG. 28A). We hypothesized that $C_6F_4$ linker may be responsible for this unique behavior and thus performed control CD spectroscopic measurements on 3a and 3b. Indeed, in the case of 3a we observed a well-defined CD spectrum exhibiting absorbance maxima at 222 nm. For 3b, a similar spectrum, but with a decreased molar residual ellipticity (MRE) value centered at ~226 nm was observed (FIG. 28B). While the nature of the signals in the CD spectra of 3a and 3b is yet to be determined, we were able to semi-quantitatively estimate the helical content of 6, 6a-b, assuming that MRE values arising from the introduction of the perfluorinated staple do not change significantly between 3a/3b and 6a/7b respectively. We observed that while 6 species exhibited approximately 16% α-helical structure, stapling with 2a significantly enhances the α-helical content of the stapled peptide 6a up to 53%. For 6b, stapling was done with a longer linker (2b) and the α-helical content changed to 36%. This modest change is not surprising since the length of 2b is significantly longer than the distance between two Cys residues positioned at i, i+4 in a model α-helix. These observations were further corroborated from the molecular dynamics (MD) simulations of peptides 6 and 6a,b.

To test whether the perfluoroaryl crosslinks affects the proteolytic stability of the modified variants, we compared the distributions of cleaved products of 6 and 6a,b by LC-MS after treatment with protease. From these experiments we observed enhanced proteolitic stabilities of stapled 6a,b compared to unstapled peptide 6, when these species were incubated with trypsin or chymotrypsin. This is consistent with the observed conformational changes in stapled peptides 6a,b rendering these structures less prone to amide-bond cleavage by proteases. A drastic difference was observed when proteinase K was incubated with these peptides. As such, no Leu-Leu cleavage was observed for 6a,b (in contrast to 6) upon prolonged incubation of these peptides in the presence of proteinase K (3 hours), suggesting that the perfluoroaryl staple is capable of protecting the amide bonds positioned between the two Cys residues. We then evaluated and compared the binding affinities of peptides 6 and 6a,b using surface-plasmon resonance (SPR) assay enabled by the Biacore system. C-CA protein domain was immobilized on the Au-based chip via covalent attachment chemistry, and peptide analytes were evaluated at 5 µM concentrations (FIG. 28C). From these experiments we observed binding affinity differences, where the stapled peptides 6a,b were identified as better binders than 6. Significantly, observed binding trend correlates with the α-helicity of the peptides. We further investigated whether these stapled peptides possess enhanced cellular interaction properties due to the combination of altered secondary structure and enhanced hydrophobicity provided by a perfluorinated staple moiety. To evaluate these properties we synthesized FITC-based dye-labeled variants of 6a,b referred to as 7a,b (FIG. 27). Stapling of the unprotected FITC-labeled peptide 7 occurred smoothly and was not inhibited by the presence of a thiourea moiety (in contrast to the case of an olefin metathesis approach). Upon incubation of these peptides at 5 µM concentrations with HEK293T cells for 4 hours, we observed significant uptake of the stapled peptides 7a,b (FIG. 28E) localized primarily in the cytosol and no fluorescent positive cells for the unstapled variant 7 via confocal microscopy. Importantly, control experiment with 9 (peptide analog stapled via olefin metathesis, FIG. 27) suggested that 7b qualitatively exhibits similar uptake properties. Additional experiments with flow cytometry revealed similar trend in peptide uptakes (FIG. 28D). Further control experiments with non-stapled peptide variants 8a and 8b (FIG. 27B) featuring perfluoroaromatic units installed only on one cysteine residue suggest that stapling is an essential requirement rendering these peptides cell-permeable.

Figure 29:
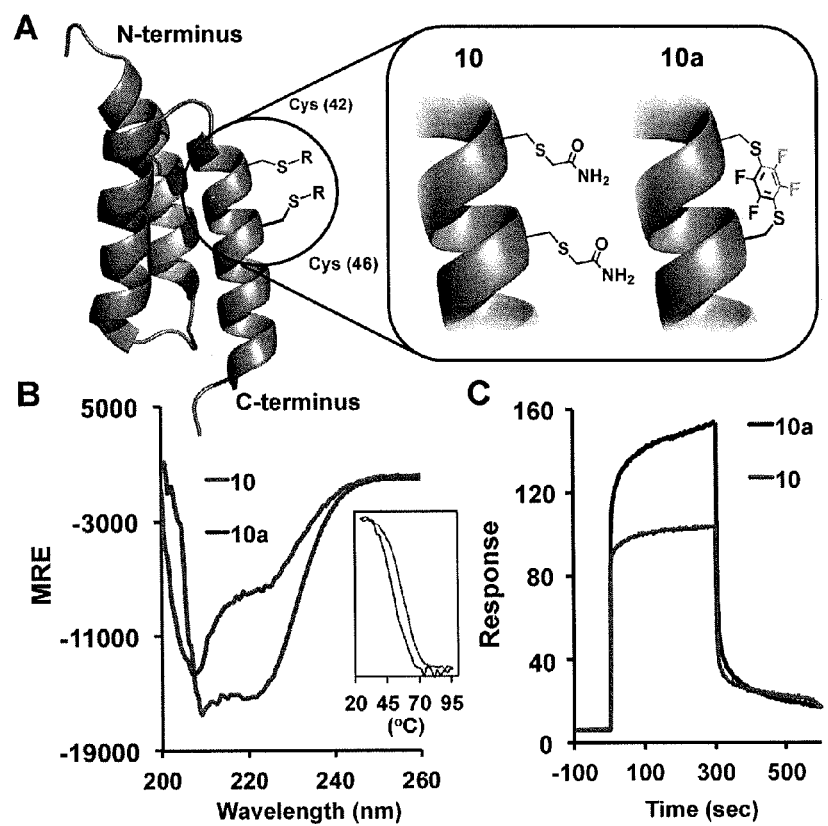
FIG. 29 depicts (A) Representation of the HER-2 affibodies (PDB code: 2B89) with chemically modified Cys positions [Cys$^{42}$, Cys$^{46}$] via stapling (10a) and alkylation (10); (B) CD spectra of 10 and 10a, and the corresponding temperature-dependent melting curves measured from the CD spectra at 222 nm (inset); (C) Biacore binding sensograms of 10, 10a with immobilized HER-2 extracelluar binding region (adsorption/desorption time–300 sec).

Finally, we evaluated whether the developed stapling chemistry is compatible with the conditions used for the total chemical synthesis of proteins. We chose to install a staple on the C-terminal helix of a previously engineered affibody that has ~1 nM affinity for the HER-2 protein receptor. Affibodies 10 and 10a were prepared via consecutive native chemical ligation (NCL) from three fragments, where the C-terminal peptide was stapled using the developed protocol (FIG. 29A) Upon examination of the CD spectra of the synthesized affibodies 10 and 10a we observed a well-defined α-helical motif (FIG. 29B), suggesting the introduction of the perfluoroaryl staples did not alter the overall protein topology (note, that the contributions of the perfluoroaryl moieties in these CD spectra should still persist, vide supra). Notably, temperature dependent melting properties of 10a was not compromised from the introduction of the staple. Furthermore, upon evaluating binding properties of these affibodies (FIG. 29C) we observed similar binding of the stapled affibody as compared to the alkylated congener 10. To the best of our knowledge, this is the first example demonstrating the possibility of incorporating stapled peptide motifs within the structure of a larger protein scaffold without significantly altering their functional properties.

In conclusion, we demonstrated a new and mild synthetic platform for cysteine arylation. The developed method operates at room temperature in polar organic solvents and shows excellent selectivity and functional group tolerance. As a result, we were able to utilize this approach towards stapling unprotected peptides, thereby positively altering their biological properties. We further demonstrated incorporation of a perfluoroaryl staple within the small tri-helical affibody protein. We believe this approach may expand the toolkit of available chemical transformations to alter the properties of biomolecules that contain a thiol. In addition, our approach is complementary in several aspects to the olefin metathesis mediated peptide stapling. The chemistry reported here, operates on unprotected peptides, does not necessitate the use of a metal-based catalyst, and poses no requirement for expensive non-natural amino-acid precursors. Furthermore, in contrast to bromoalkyl/benzyl chemistry that can produce over alkylated species, this platform is selective towards cysteines and provides staples featuring lipophilic perfluorinated moieties.

Figure 42:
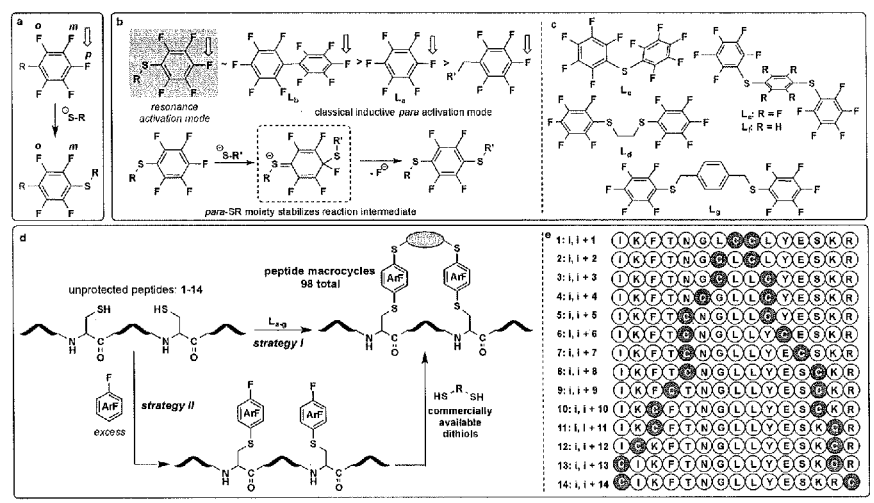
FIG. 42 depicts an unprotected peptide macrocyclization scan enabled by S$_N$Ar "click" transformation between thiols and activated perfluoroaromatics: (a) the reaction scheme highlighting the regioselectivity of the S$_N$Ar process leading to preferential substitution at para position of the pentafluoroaryl moiety with respect to the R substituent; (b) the reactivity trend of perfluoroaryl-based electrophiles governed by two independent activation modes; (c) the library of bifunctional perfluoroaryl-based linkers containing thioether moieties capable of activating corresponding para-CF moiety towards nucleophilic attack via resonance stabilization of the Meisenheimer intermediate; (d) two independent strategies designed to probe macrocyclization scan with linkers $L_a$-$L_g$; and (e) 14 model cysteine-containing unprotected peptides used for the studies (SEQ ID NOS 97-110, respectively, in order of appearance).

Convergent Diversity-Oriented Side-Chain Macrocyclization of Unprotected Polypeptides In certain embodiments, the invention relates to a peptide macrocyclization scan based on the cysteine perfluoroarylation via the $S_NAr$ "click" transformation. Two simple, complementary synthetic strategies embody the versatility of our approach (FIG. 42d). Specifically, access to peptide macrocycles can be achieved by either cross-linking cysteine containing peptides with perfluoroaryl-based linkers, or by incorporating non-crosslinked perfluoroaryl-based moieties first, followed by their macrocyclization with dithiol reagents. The developed macrocyclization scan is enabled by our strategy to maximize the reactivity of perfluoroaryl-based synthons without compromising their synthetic accessibility, robustness and tailorability (FIG. 42b,c). Site-independent reactivity of the described platform ultimately allowed us to conduct highly efficient macrocyclizations in a series of peptides featuring two cysteine residues incorporated at the positions ranging from i, i+1 to i, i+14 (FIG. 42e). The developed approach is fully convergent allowing for rapid and operationally simple generation of chemical complexity from unprotected peptides containing naturally occurring amino-acid residues.

In an effort to expand peptide stapling with two Cys moieties beyond i, i+4 positions, we sought to develop an extended library of bifunctional cross-linking molecules with rationally varied properties containing two perfluoroaryl units. Based on our experimental observations, species containing aliphatic groups in the para position exhibited diminished reactivity toward the nucleophilic attack rendering the $S_NAr$ process slow and inefficient (FIG. 42b). This phenomenon is attributed to the poor electron-withdrawing nature of alkyl-based substituents, which are not sufficiently activating for the para-C—F bond substitution at room temperature.[17] We thus decided to explore a less-developed activation pathway that features a para-substituted thioether group appended on perfluoroaryl-based unit. Our DFT computational studies corroborate the presence of a para-S substituent on the pentafluorophenyl moiety consistently renders a larger para-C—F bond polarization than in the alkyl-based substituent-containing congeners (see FIG. 43). The presence of the same para-thioether moiety on the biaryl variant does not significantly change para-C—F dipole features as compared to $L_b$, though it remains large due to the inductive electron-withdrawing effect produced by the para-S—$C_6F_4$ substituent. Therefore, we chose to focus our efforts on both S-substituted 1-nonafluorobiphenyl and 1-pentafluorobenzene groups for facile nucleophilic aromatic substitution chemistry necessary for the bioconjugation (vide supra).

We utilized two independent routes to synthesize a new class of bifunctional perfluoroaromatic-based linkers $L_c$-$L_g$ (note that, linker $L_c$ can also be obtained from an existing commercial source). Linkers containing alkyl and benzyl moieties were synthesized via $S_NAr$ chemistry between an excess (>25 fold) of commercially available hexafluorobenzene and alkyl/benzyl dithiol species (see Examples). Utilizing an excess of the perfluoroaromatic reagents ensures the formation of the mono-substituted species and minimizes the production of oligomeric and polymeric products. However, no desired product was observed when these conditions were applied to aromatic dithiols. To circumvent this, linkers containing aromatic moieties were synthesized via Cu-mediated cross-coupling of the corresponding aryl halide or dihalide and commercially available pentafluorophenylthiol. The proposed structural formulations of linkers $L_c$-$L_g$ are fully consistent with their heteronuclear NMR spectra in solution.

To probe peptide macrocyclization with the perfluoroaryl-based linkers, we designed a series of 14 peptides featuring a diverse set of natural amino-acid residues and two cysteine moieties deliberately varied at sites from i, i+1 to i, i+14 (labeled as 1'-14', see FIG. 42e). To start, we tested the macrocyclization protocol with linkers $L_a$ and $L_b$ utilizing strategy I (FIG. 42d), wherein bifunctional cross-linkers are expected to interconnect two cysteine sites producing peptide-based macrocyclic structures. Upon treating 7' with two equivalents of $L_a$ in the presence of TRIS base (50 mM, in DMF), we observed nearly complete consumption of the starting material within 2 hours as determined by LC-MS analysis. Under these conditions nearly 80% of the macrocycle product 7a' was observed in addition to a small amount of oxidized 7' formed via intramolecular disulfide formation (data not shown).

When the longer linker $L_b$ was used under the same conditions, the macrocyclic product 7b' formed in >90% yield after 2 hours with a minimal amount of the oxidized by-product. This noticeable increase in the product yield can be attributed to a longer length and higher reactivity of $L_b$ as compared to $L_a$, rendering the process more efficient. $^{19}F$-NMR spectra of the purified peptides 7a'-7b' are consistent with the proposed cysteine arylation, where only resonances observed correspond to the 1,4- and 1,10-substituted patterns on the perfluoroaromatic moieties. Given the high sensitivity of $^{19}F$ nucleus to the local magnetic field, we observed additional complexity in both of these spectra due to the presence of slowly exchanging conformers. The observed dynamic behavior is likely a result of the slow rotation of the perfluoroaromatic ring moieties, which can be modulated by temperature and solvent.

When peptide 7' was treated with the next-generation linkers $L_c$-$L_g$, reaction yields were greater than 85% and not dependent on the chemical nature or length of the moiety. We observed small amounts, less than 10%, of cross-linked by-products resulting from the competing intermolecular processes. Regio- and chemo-selectivity of these processes were confirmed via $^{19}F$ NMR spectroscopy of the purified peptides 7c-7d. Overall, macrocyclization studies with i, i+7 peptide 7' indicates that macrocyclization via $S_NAr$ chemistry between cysteine thiolates and activated perfluoroaromatic linkers $L_a$-$L_g$ is highly efficient and chemoselective. Importantly, in contrast to the stapling chemistry via olefin metathesis, this approach does not necessitate the use of non-natural olefin-containing amino acids as well as precise tuning of the length and stereochemistry of these residues.

Given recent studies demonstrating the feasibility of peptide macrocyclization with hybrid linkers at positions beyond those located on the same face of the α-helical loop (single turn—i, i+4; double turn—i, i+7; triple turn—i, i+11), we sought to further test the developed chemistry by scanning the polypeptide in either direction via this platform. Conducting macrocyclization reactions with conditions employed for peptide 7', we tested the corresponding peptides where cysteine residues are positioned in i, i+6 (peptide 6') and i, i+8 (peptide 8') fashion. We observed greater than 75% macrocyclization yields for all 14 reactions with linkers $L_a$-$L_g$, where more flexible linkers produced the corresponding macrocycles 6e-g and 8e-g almost exclusively with yields equal or greater than 90%.

We further tested this approach by probing the lower and upper limits of the scan with peptides 1'-5' and 9'-14'. The upper limit of our macrocyclic scan was tested with peptides 9'-14', which were subjected to linkers $L_a$-$L_g$. The reaction with linker $L_a$ produced the desired cyclic peptide 14a in only 40% yield, while the oxidized by-product was observed to be the major species for this reaction (ca. 50%). On the other hand, when linker $L_b$ was used with peptide 14, the macrocyclic species 14b formed in nearly quantitative yield. Importantly, reactions with linkers $L_c$, $L_e$ and $L_f$ also produced yields greater than 90% for the desired peptide macrocycles, whereas reduced yields were observed for $L_d$ and $L_g$. The observed reactivity trends suggest that a proper combination of linker length and electrophilicity are necessary for efficient macrocyclization for longer peptides.

Figure 44:
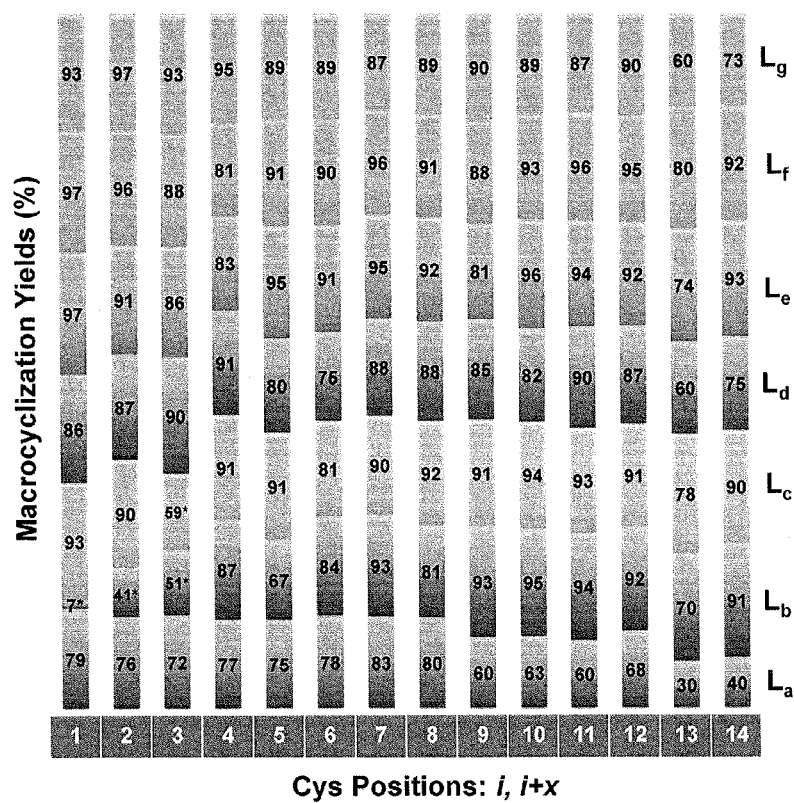
FIG. 44 depicts a bar graph summary of the macrocyclization scan with peptides 1'-14' and linkers $L_a$-$L_g$. Number within each bar represents corresponding yield of the macrocyclization product. Note, for yields denoted with *, re-optimized conditions were employed.

Interestingly, only small amounts of cross-linked macrocyclic species were observed when $L_b$ was reacted with peptides 1' and 2', where instead large quantities of by-products were observed (see SI). Observed diminished yields of 1b' and 2b' are likely due to the conformational rigidity and length of $L_b$, which is incompatible with the relatively short distance separating the Cys residues in peptides 1' and 2'. On the other hand, reactions with other linkers produced corresponding macrocyclic peptides in yields greater than 75%. All transformations involving the new family of flexible linkers $L_d$-$L_g$ produced peptide macrocyclic products with most yields consistently greater than 90% (see FIG. 44). Upon further investigation, we discovered that macrocyclic peptides 1b' and 2b' could be obtained in better yields, when re-optimized conditions featuring higher dilution and lower stoichiometric ratio of the organic linker are employed (FIG. 44). Given previously recognized difficulties associated with macrocyclization strategies of short peptide sequences (<4 residues) using bifunctional cross-linkers, this approach demonstrates how this chemistry can circumvent previous limitations. Similarly, i, i+4 peptide 4' and its nearest peptide scan neighbors 3' and 5' underwent smooth macrocyclization yielding the desired hybrid macrocyclic species as major products in yields greater than 80% with new linkers $L_d$-$L_g$ (see FIG. 44), whereas diminished yields were observed in the formation of 3b' and 3c' (20% and 41%). Employing the re-optimized reaction conditions allowed us to improve the respective yields of peptides 3b' and 3c' (vide supra). Overall these results highlight the feasibility of the macrocyclization scan, ultimately demonstrating that properly designed perfluroaromatic-based linkers can mediate this process generally irrespective of their chemical identity. The observed utility of the perfluoroaryl-based $S_NAr$ approach for macrocyclization at cysteine residues significantly expands access to these hybrid structures when compared to the chemistry featuring allyl and benzyl halides, where yields were found to be extremely sensitive to the linker.

Overall, utilizing only 7 model linkers we produced 98 macrocyclic peptides without optimization of the conditions for each reaction (FIG. 44). In all but one instance we observed at least a 30% yield of the desired peptide macrocycle, and for reactions employing next-generation linkers $L_c$-$L_g$ the yields were greater than 60% (FIG. 44). Approximately half of all the macrocyclization reactions tested, product yields were greater than 90%, and for the most of the reactions conducted with the new linkers $L_c$-$L_g$ yields were greater than 80%. To the best of our knowledge, the cysteine perfluoroarylation platform represents the first instance where a macrocyclization scan can be carried out in a manner generally independent of the positions of the side-chain amino-acid residues.

To further highlight the generality of the developed macrocyclization platform we envisioned that it should be possible to avoid the requirement for the linker syntheses by utilizing a reverse strategy. Specifically, we envisioned incorporating pentafluorophenyl or nonafluorobiphenyl moieties directly onto unprotected cysteine-containing peptides, which then can undergo macrocyclization with commercially available dithiol reagents (FIG. 42e, strategy II). To test this hypothesis, we utilized peptide 7', which was treated with excess of hexafluorobenzene and decafluorobiphenyl reagents yielding bis-perfluoroarylated cysteine peptides 7a" and 7b", respectively. 1,4-Butanedithiol and 1,4-benzene-dimethanethiol were chosen as model dithiol reagents to test for the desired macrocyclization chemistry with 7a' and 7b". As a standard protocol, 1 mM solutions containing perfluoroaryl-containing peptides 7a" and 7b" were treated with 2-fold excess of dithiol linker in the presence of 50 mM solution of TRIS base in DMF. LC-MS analysis of the reactions indicated complete consumption of the starting materials occurred within 2 hours and cyclic products were formed with yields greater than 90% in both cases. These experiments show the reverse strategy for macrocyclization is indeed feasible. Given that perfluorinated moieties in 7a" and 7b" are less sterically hindered than similar cysteine thiolate sites, more rapid and selective macrocyclization chemistry is observed as a result. Importantly, long peptide sequences can undergo efficient macrocyclization via this strategy, as suggested by the nearly quantitative conversion of peptide 14a" to its corresponding macrocycle when treated with 1,4-butanedithiol.

In summary, for the first time, we show how cysteine perfluoroarylation via $S_NAr$ "click" transformation enables a site-independent and convergent diversity-oriented peptide macrocyclization scan. Two complementary strategies allow for the rapid construction of side-chain functionalized peptide macrocycles and simultaneous complexity generation enabled by the highly tailorable perfluoroaryl-based linkers. Studies performed with model compounds suggest that the peptide amino-acid sequence and linker identity do not significantly diminish ones ability to form hybrid macrocycles. Given the recently observed improvements in stability, cell-uptake and target binding affinity of the peptide macrocycles stapled with perfluoroaromatic-based moieties, we envision this newly developed scan will expand the toolbox needed for the development of biologically active constrained-peptide therapeutics by allowing one to rationally design and screen for promising protein-binding agents.

Stapled Peptides as Brain Cancer Therapeutics

In certain embodiments, the invention relates to the at-will delivery of fluorine-containing stapled peptides to the cytosol of cancer cells. In certain embodiments, the invention relates to compounds that disrupt the key p53/MDM2 interaction in human glioblastoma cells and thereby cause tumor cell death.

Gliomas are very difficult to treat by chemotherapy and consequently they are associated with extremely poor prognosis; new therapeutic approaches are needed. In certain embodiments, the invention relates to a fundamentally new way to treat brain cancer. In certain embodiments, the invention relates to a powerful platform that allows for facile delivery of stable peptide variants to disrupt key protein-protein interactions. In certain embodiments, the invention relates to the disruption of the p53/MDM2 interaction inside brain tumor cells, thereby causing cell death. Considering the high level of p53 mutation and MDM2 amplification in glioblastoma patients, this approach provides a novel treatment option. Peptide design, discovery, and engineering are extremely powerful; routine methods exist to morph them into potent bioactive agents. However, robust delivery of peptides into cells does not exist. In certain embodiments, the compounds of the invention solve this problem and allow for the marriage of the peptide discovery engine and the delivery power to the cytosol.

In certain embodiments, the invention relates to creating a robust fluorine-rich stapling peptide platform. Previous studies by several research groups established that certain chemical transformations for side-chain crosslinking in a polypeptide with properly aligned residues results in a so-called "stapled" motif, responsible for improving different chemical and biological properties of their parent-unstapled surrogates. None of the current approaches are modular and versatile nor benefit from the important properties of fluorocarbon-based species. Cysteine perfluoroarylation leads to new compounds with fundamentally new properties owing to the rigidity and lipophilicity of the perfluoroaromatic linkers. In addition, while approximately 30% of pharmaceuticals on the market contain fluorine-based functional groups, this important structural feature has not been explored in the field of conformationally restricted peptide pharmaceuticals.

Figure 30:
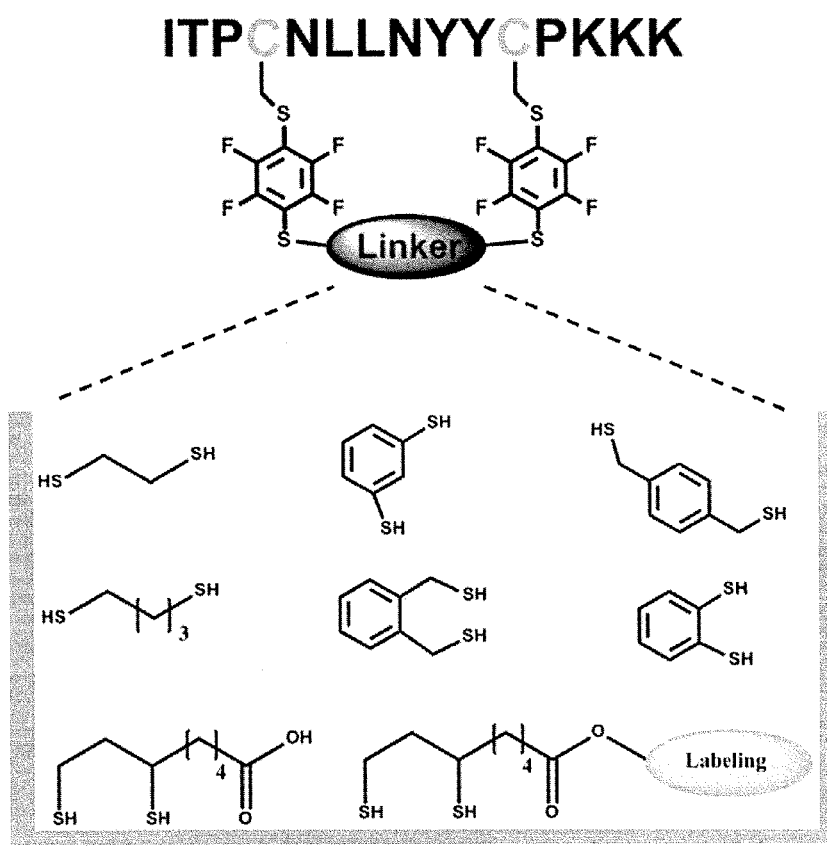
FIG. 30 depicts various linkers that can be used in stapled peptides of the invention (SEQ ID NO: 47).

In certain embodiments, the presence of para-S moiety on the perfluoroaromatic ring drastically increases the reactivity of the corresponding para-CF site towards nucleophilic attack of the second thiolate species. This phenomenon can be qualitatively explained by the ability of para-S site to stabilize negative charge in the transition state of this reaction. Guided by this observation we propose to develop and use a new set of linkers all of which contain para-S moiety, which will drastically increase their reactivity. Furthermore, given that these linkers can be generated in a facile chemical process between corresponding thiols and hexafluorobenzene, in certain embodiments, the linker comprises aryl, alkyl, benzyl, or other types of bridging units. In certain embodiments, the linkers are variable in length, flexibility or polarity. See FIG. 30.

In certain embodiments, the invention relates to peptides that are consistently stapled at a variety of positions from ranging from i, i+2 to i+13 as shown in FIG. 31. In certain embodiments, the invention relates to peptide systems containing multiple staples. In certain embodiments, the invention relates to methods of stapling peptides with >90% yields, rendering purification of final products trivial.

In certain embodiments, the invention relates to treating a cysteine-containing peptide with an excess (>100 fold) of hexafluorobenzene or decafluorobiphenyl, leading to the formation of non-bridged (non-stapled) SR species. This class of peptides undergoes facile $S_NAr$ process with thiols at room temperature within several hours resulting in a peptide stapling. In certain embodiments, a large pool of aromatic and aliphatic bifunctional thiol linkers (>100 exist commercially) can be used for stapling. This chemistry offers another potential benefit of running these reactions in water, since it is not limited by the poor perfluoroaryl linker solubility in aqueous media.

In certain embodiments, the invention relates to delivering stapled peptides to the cytosol and striking p53/MDM2 for brain cancer treatment. In certain embodiments, the invention relates to the modification of a D-polypeptide that has sub-nanomolar affinity for MDM2. This D-polypeptide disrupts the p53/MDM2 interaction, causing cell death in glioblastoma cells.

The tumor suppressor protein p53 functions as the 'guardian of the genome' by controlling cellular response to stress signals. Extensive drug discovery efforts have been focused on the p53 pathway because mutations of the TP53 gene or alterations in the p53 pathway account for nearly all cancers. In many cases, the inactivation of p53 stems from the over-expression of its crucial negative regulator MDM2, an E3 ubiquitin ligase binds the N-terminal transactivation domain of p53 and targets it for ubiquitin-dependent degradation. Blocking the p53/MDM2 interaction has been demonstrated to be exceptionally effective strategies for suppression of tumor cell growth. Despite remarkable progress in developing small molecule drugs that aim to target p53/MDM2 interaction, peptides that mimic natural interaction more effectively are still under development to increase the binding affinity and specificity. Certain small D-peptides are capable of binding MDM2 with nanomolar or picomolar affinity via mirror image phage display and rational design. While these peptides are highly resistant to proteolysis yet still capable of p53 activation, clearly of tremendous therapeutic value, the challenge of efficiently delivering them to the cytosol of tumor cells severely limited their application.

In certain embodiments, the invention relates to a stapled peptide sequence designed to bind the C-terminal domain of an HIV-1 capsid assembly polyprotein (C-CA). In certain embodiments, the stapled peptide showed enhancement in binding, cell permeability, and proteolytic stability properties, as compared to the unstapled analog. Specifically, perfluoroaryl crosslinks affected the proteolytic stability of the modified variants; we compared the distributions of cleaved products of unstapled and stapled peptide variants by LC-MS after treatment with proteases such as trypsin, chymotrypsin, and proteinase K. This is consistent with the observed conformational changes in stapled peptides rendering these structures less prone to amide-bond cleavage by proteases. A drastic difference was observed when proteinase K was incubated with these peptides, no Leu-Leu cleavage was observed upon prolonged incubation suggesting the perfluoroaryl staple protects the amide bonds positioned between the two Cys residues. We also observed binding affinity differences in that the stapled peptides were better binders than unstapled variant. Significantly, the binding trend correlated with the α-helicity of the peptides. From a set of confocal microscopy and flow cytometry experiments we further concluded that that perfluoroaromatic stapling is an essential requirement rendering these peptides cell-permeable, while no significant cell-permeability was observed for unfunctionalized peptides as well as species containing perfluoroaryl group attached only at one cysteine residue (unstapled control).

In certain embodiments, the invention relates to enhancing the α-helical fold in the stapled peptides and increasing their cell permeability. Combination of these two vital parameters in our stapled peptides will render this class of substances capable of inhibiting the p53/MDM2 interaction in cancer cells. In certain embodiments, the invention relates to human glioblastoma U87. In certain embodiments, the invention relates to a L-peptide inhibitor ($^L$PMI) from phage display library with an affinity of 10 nM, and a rationally evolved inhibitor with an affinity of 0.45 nM ($^D_p$PMI). In certain embodiments, the invention relates to the ability of the compounds to efficiently enter cells. In certain embodiments, the invention relates to the inhibitory effects of the compounds on p53/MDM2 interactions in human glioblastoma U87. In certain embodiments, at the protein level, the inhibition results in stabilization and accumulation of the p53 protein, and activation and expression of MDM2 and other p53 regulated protein. In certain embodiments, the invention relates to the examination of the protein level of p53, MDM2 and another p53 regulated protein, p21. At the cellular level, these events cause cell cycle arrest and apoptosis. In certain embodiments, the invention relates to the use of bromodeoxyuridine (BrdU) staining to analyze the cell cycle, and MTS assays in conjunction with TUNEL assays to detect apoptosis.

Figure 32:
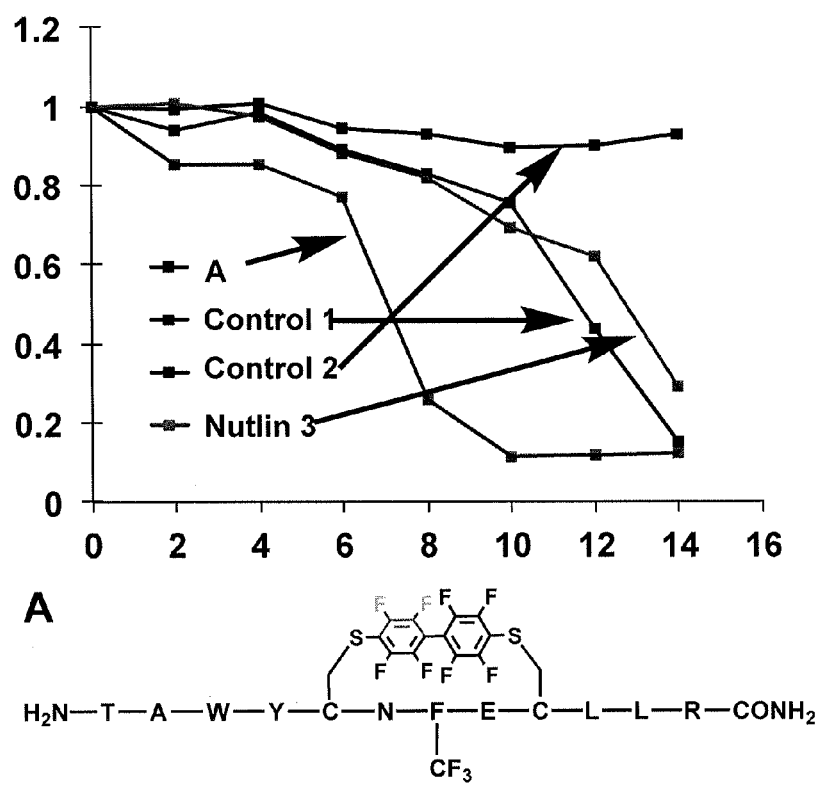
FIG. 32 depicts the results of a MTS assay after treatment of U87 cells with stapled peptide A, two negative controls, and nutlin-3, a positive control (SEQ ID NO:19).
Figure 34:
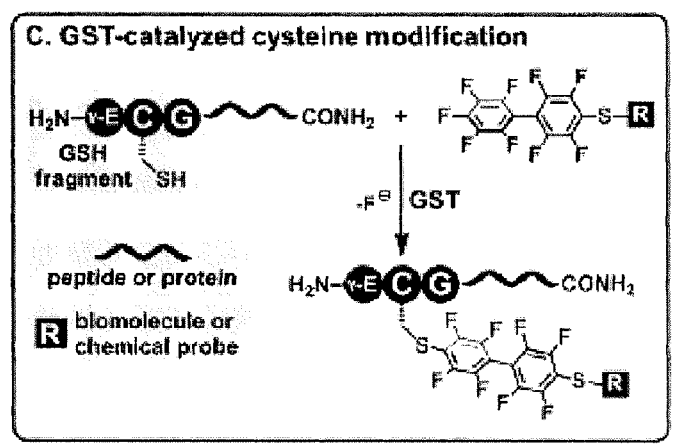
FIG. 34 depicts GST-catalyzed cysteine modification. GST catalyzes the conjugation of probes bearing a 4-mercaptoperfluorobiphenyl moiety (Cys-III) to the N-terminal γ-Glu-Cys-Gly sequence of a peptide or protein. Amino acids are shown in single-letter code. γ-E stands for γ-glutamyl.

U87 cells were treated with stapled peptides of the invention. Cell viability was monitored using MTS assay. Stapled peptide $^D_p$PMI exhibited a high level of cell death, compared to the controls (FIG. 32).

In certain embodiments, the invention relates to the investigation of the proteolytic stability, including degradation rates and dominant cleavage pathways, of the stapled peptides by exposing the peptides to various proteases such as trypsin, chymotrypsin, and proteinase K.

In certain embodiments, the invention relates to the investigation of the efficiency of cellular uptake of stapled peptides. In certain embodiments, the efficiency of cellular uptake is studied using flow cytometry. In certain embodiments, the uptake of FITC-labeled peptide is quantitatively measured by allowing trypsin degradation of the cell membrane. In certain embodiments, confocal microscopy imaging in both live and fixed cells is used. In certain embodiments, the specific intracellular localization of the peptides will be analyzed by staining the plasma membrane, nucleus, endosome or other organelles. In certain embodiments, the cell lines are selected from the group consisting of CHO-K1, U87, HeLa, and HEK293T. In certain embodiments, the invention relates to the investigation of the mechanism of cellular uptake of the stapled peptides. In certain embodiments, the uptake is by direct penetration or by endocytosis.

In certain embodiments, the invention relates to a method of delivering potent polypeptides into the cytosol of brain tumor cells. In certain embodiments, the invention provides a diverse toolkit that allows brain researchers to rapidly introduce fluorine-rich linkers within peptides thereby improving their cellular uptake, proteolytic resistance and target binding.

Enzyme-Catalyzed $S_NAr$ Processes

In certain embodiments, the invention relates to this synthetic model to study enzyme catalyzed (glutathione S-transferase) $S_NAr$ process, which will enable us to perform these stapling reactions in minutes rather than hours.

In certain embodiments, the invention relates to chemistry suitable for aqueous conditions, such as that involving glutathione S-transferase (GSTs). GSTs catalyze $S_NAr$ reactions between Cys residue of glutathione (GSH-γ-Glu-Cys-Gly) and various electrophiles, thus allowing the cell detox xenobiotics in vivo.

In certain embodiments, the invention relates to a bioconjugated compound made by a perfluoroaryl-cysteine $S_NAr$ "click" reaction and catalyzed by GST. GST facilitates this bioconjugation in aqueous media, and introduces previously unattainable chemo- and regioselective functionalization of a single cysteine thiol on the peptide chain in the presence of other unprotected cysteine residues and reactive functional groups. This process is fast and can be completed in seconds providing an entry to a new peptide macrocyclization. This chemistry can be carried out at different temperatures (for example, about 4° C. to about 60° C.) and is compatible with the addition of organic co-solvents (for example, up to about 20%).

Given the broad scope of electrophiles accepted by GST isozymes, the promiscuity of this enzyme family is sufficient to mediate reactions between perfluoroaryl electrophiles and peptides containing GSH fragment (γ-Glu-Cys-Gly) in aqueous environment.

Figure 35:
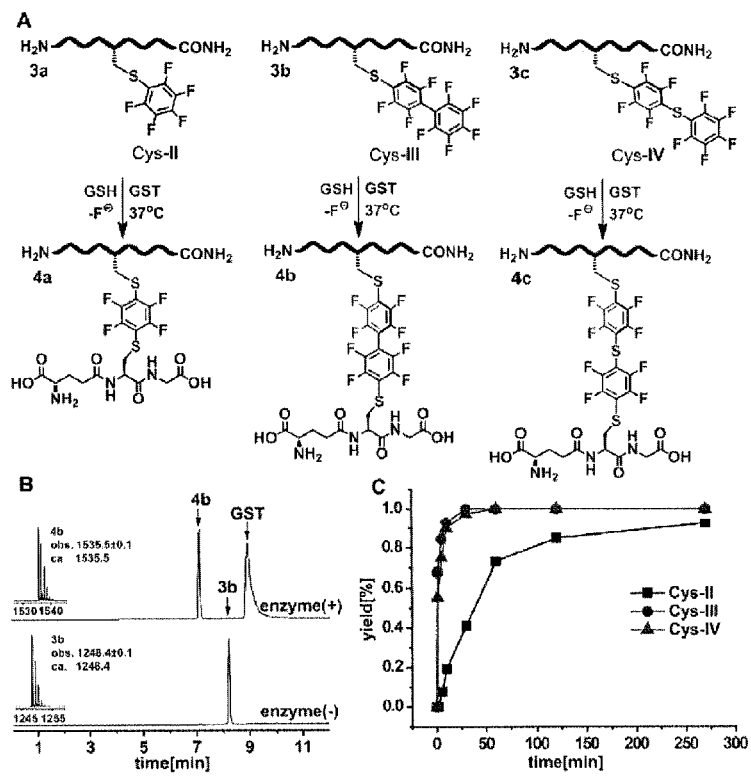
FIG. 35 depicts GST-catalyzed conjugation of GSH to peptides containing cysteines modified with perfluoroaryl electrophiles. (A) reaction conditions: 1 mM 3a-c, 1 mM GSH, 2 mg/mL GST, 20 mM tris(2-carboxylethyl)phosphine hydrochloride (TCEP.HCl), 0.1 M phosphate buffer, pH=8.0, 37° C. Peptide sequences of 3a-c: H$_2$N-VTLPSTC*GAS-CONH$_2$ (SEQ ID NO: 5), C* stands for the modified cysteine. (B) LCMS analysis of crude reaction with peptide containing Cys-111 residue at 30 minutes, (C) Rates of formation of GSH-conjugated product with different electrophiles. Yields were LCMS-yields calculated by UV280.
Figure 37:
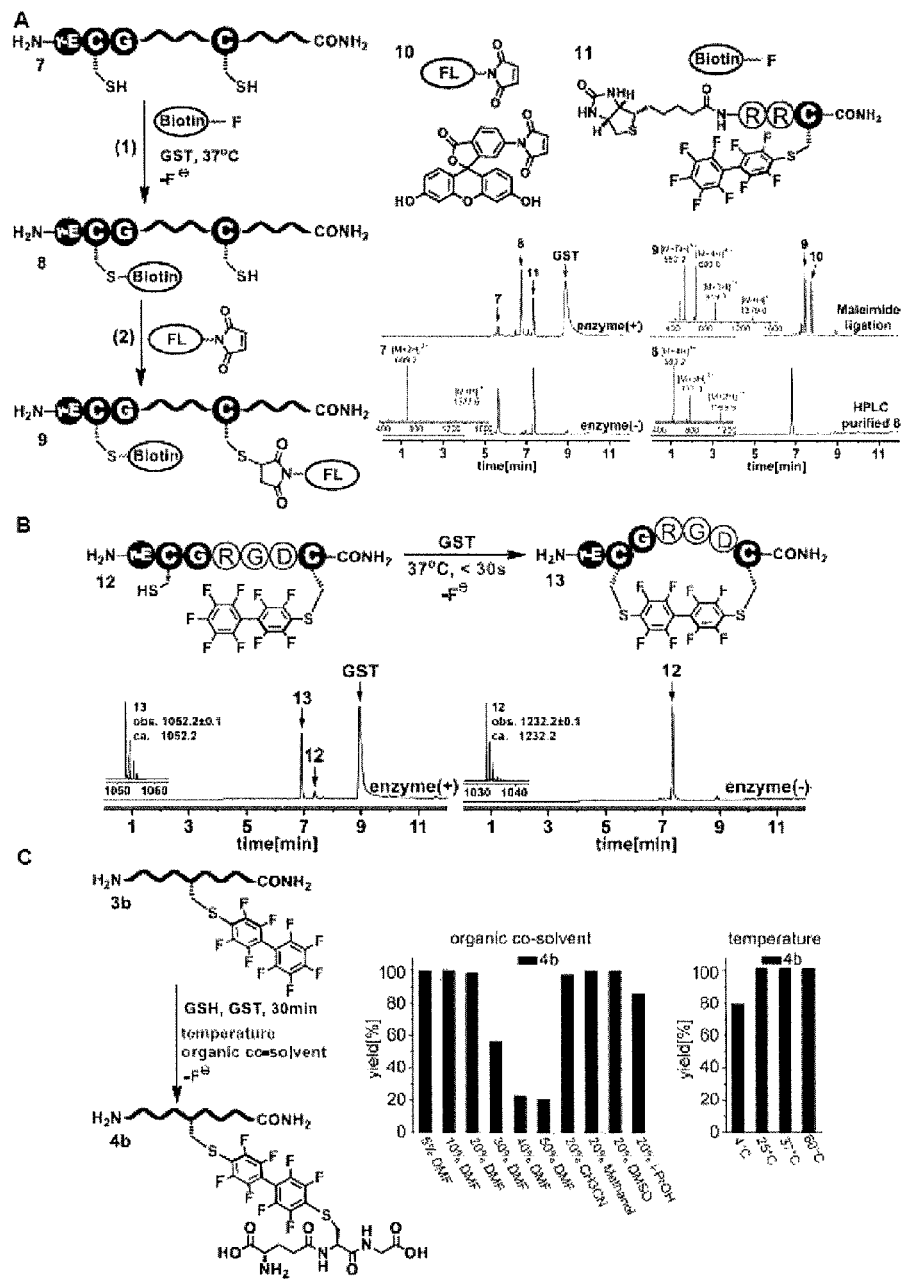
FIG. 37 depicts the synthetic utility of GST-catalyzed cysteine modification. LCMS traces are shown as total ion current. Yields are LCMS-yields calculated by UV280. (A) Sequential labeling of biotin and fluorescein (FL) probes to peptide 7 containing two cysteines. Peptide sequence: H$_2$N-γ-ECGPTAAKESCLL-CONH$_2$ (SEQ ID NO: 6). Reaction conditions: (1) 0.5 mM 11, 1 mM 7, 2 mg/mL GST, 20 mM TCEP.HCl, 0.1 M phosphate, pH=8.0, 37° C., 40 minutes; (2) 0.5 mM 8, 1 mM 10, 0.1 M phosphate, pH=6.0, 10 minutes. (B) Peptide macrocyclization catalyzed by GST. Reaction conditions: 1 mM 12, 2 mg/mL, GST, 20 mM TCEP.HCl, 0.1 M phosphate, pH=8.0, 37° C. (figure discloses SEQ ID NOS 78-79, respectively, in order of appearance). (C) GST-catalyzed conjugation of GSH to peptide with Cys-111 residue at various mixed solvent conditions and temperatures. Reaction conditions were the same as those in FIG. 35 except solvents (Left panel, percentages shown are volume ratio) and temperatures (right panel). DMF: dimethylformamide, DMSO: dimethylsulfoxide, i-PrOH: isopropanol.
Figure 38:
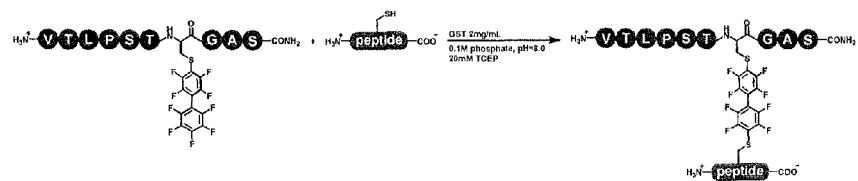
FIG. 38 depicts the scope of the GST-catalyzed reaction. Figure discloses SEQ ID NOS 80-93, respectively, in order of appearance.
Figure 40:
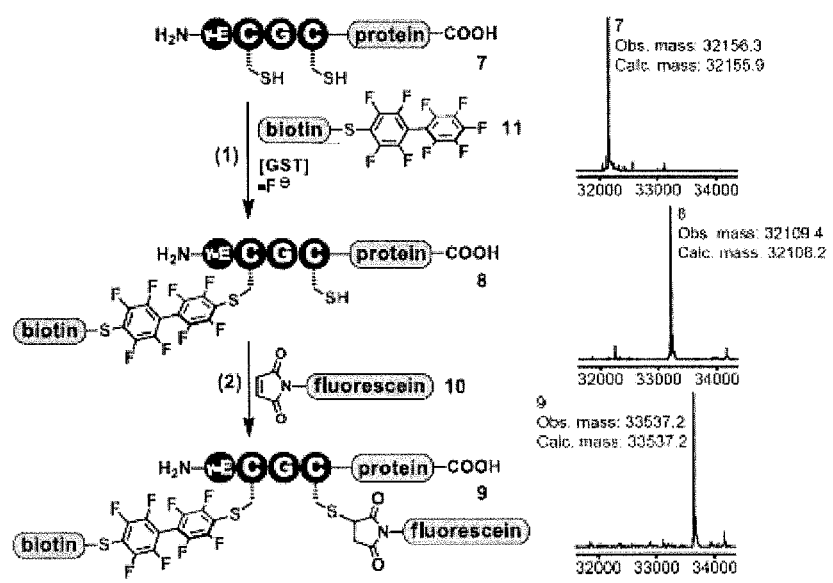
FIG. 40 depicts sequential labeling of biotin and fluorescein (FL) probes to protein 7 containing two cysteines. Figure discloses SEQ ID NOS 94-96, respectively, in order of appearance.
Figure 41:
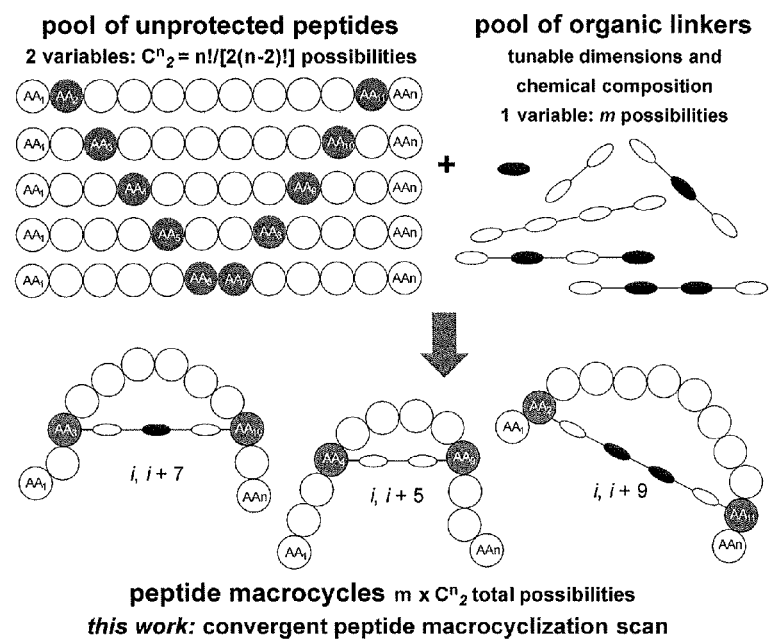
FIG. 41 depicts convergent diversity-oriented synthetic (DOS) platform for a peptide macrocyclization scan utilizing a library of chemically tailorable bifunctional linkers. AA$_x$ refers to a specific amino acid residue in the peptide chain sequence.

In certain embodiments, increasing the electrophilicity of the perfluoroaryl moiety improves the reactivity of the peptide-based substrate, thus enabling the desired enzymatic conjugation with peptides containing γ-Glu-Cys-Gly sequence. In certain embodiments, reactions with model peptides bearing different para-thioether substituted perfluoroaryl side chains show enhanced reaction rates as compared to peptide containing penta-fluoro-phenylalanine I (FIG. 35). Specifically, peptide containing cysteine modified with perfluorophenyl residue (Cys-II) (FIGS. 35A and 35C, 3a) reacted with GSH in the presence of GST at a high rate, yielding 93% of GSH-conjugated product in less than four hours. Notably, reactions with peptides containing Cys moiety functionalized with perfluorobiphenyl species (Cys-III) (FIGS. 35A and 35B, 3b) and perfluorobiphenyl sulfide (Cys-IV) (FIG. 35A, 3c) proceeded with quantitative conversions in less than 30 minutes (FIG. 37C).

Figure 36:
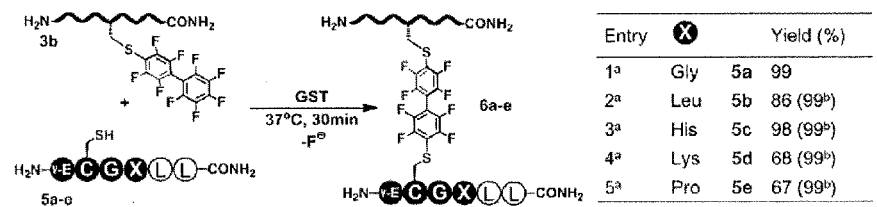
FIG. 36 depicts the conjugation of peptide containing Cys-111 residue to peptides with N-terminal γ-Glu-Cys-Gly sequence under GST-catalysis. Yields were LCMS-yields calculated by UV280. [a] Reaction conditions: 2 mM 3b, 1 mM 5a-e, 2 mg/mL GST, 20 mM TCEP.HCl, 0.1 M phosphate, pH=8.0, 37° C. [b] Yields of reactions at 120 minutes. Figure discloses SEQ ID NOS 76-77, respectively, in order of appearance.

In certain embodiments, the invention relates to ligations between two peptides containing Cys-II residue and 6-mer peptides containing a N-terminal γ-Glu-Cys-Gly. In certain embodiments, the invention involves glycyl-modified GSH-based peptides, where the first amino acid linked to Gly of the GSH was varied (FIG. 36, 5a-e). All studied reactions proceeded quantitatively within two hours (FIG. 36, entries 1-5), and reaction with 5a showed high conversion within 30 minutes (FIG. 36, entry 1). We observed decreased reaction rates with 5b and 5e as compared to 5a, which is consistent with the steric encumbrance of the Leu and Pro residues that may be important interacting with GST. Changing the second amino acid in the sequence linked to the Gly site to a less bulky residue had no effect on the conjugation rate. Nucleophilic residues (His and Lys, FIG. 36, entries 3 and 4) are compatible with the reaction. Surprisingly, the reaction with 5c produced 98% conversion within 30 minutes, suggesting that His residue may favor the reaction.

This reaction is highly selective for arylation of cysteine thiols, as evidenced by the competition experiment with a large excess of external thiol added (4-mercaptophenylacetic acid—MPAA, 100-fold, data not shown); less than X % of arylated MPAA was detected, while the GST catalyzed product of peptide 5a proceeded in high yield. While the peptide sequences can affect the relative rates of the GST catalyzed click reaction, the observed product formation for species containing Cys-III has thus far been independent of the peptide sequence employed, further suggesting that the electrophilicity of the perfluoroaryl substituents (3b, data for other sequences not shown) can dominate the GST-catalyzed $S_NAr$ reaction with modified GSH (vide supra). These results show that the promiscuity associated with GST is adequate to catalyze the bioconjugation of two modified polypeptide fragments and is unique as it demonstrates the possibility for enhancing a click reaction via enzymatic catalysis.

Figure 11:
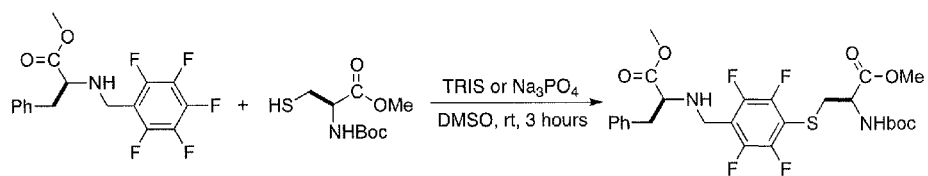
FIG. 11 depicts a model heterocoupling reaction. The product was observed in >95% yield by $^{19}F$ NMR, 89% isolated yield. The reaction also proceeds well in DMF with $Na_3PO_4$ (>95% in 5 h).
Figure 12:
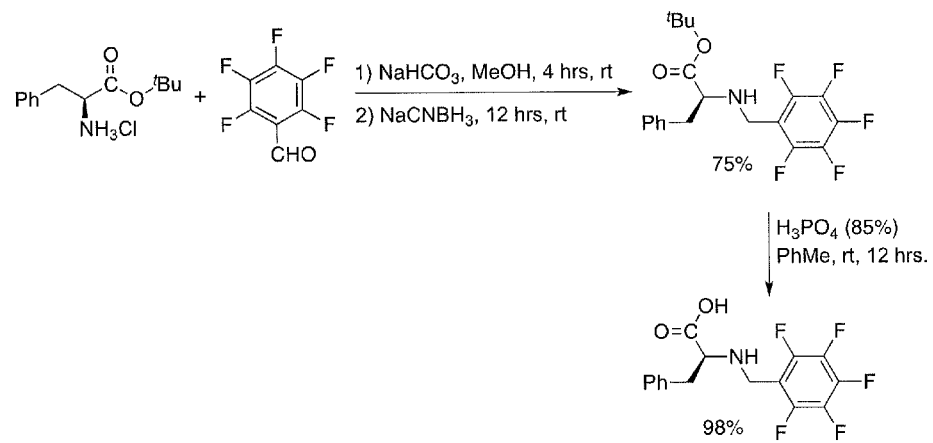
FIG. 12 depicts the synthesis of a precursor for peptide synthesis. The precursor was made on a gram-scale, and no column chromatographic purification was necessary.

The unique chemo- and regioselectivity of the GST-catalyzed arylation reaction can be further exploited to label one Cys residue in the presence of another on a fully unprotected peptide or protein. We sought to first label the N-terminal GSH Cys with biotin and subsequently react a separate Cys with a fluorophore maleimide. This provides the very first example of site-specific labeling of two Cys residues within the same unprotected peptide or protein. Biotin probe containing Cys-III moiety (FIG. 37A, 11) was conjugated to the Cys position of γ-Glu-Cys-Gly fragment in 7. The enzymatic reaction produced solely the mono-labeled product 8, and the presence of another intact cysteine was confirmed by reaction with fluorescein-5-maleimide (10), thereby producing dual-labeled species 9 (FIG. 37A). The authentic sample was prepared using protected peptides to confirm the product identity. Importantly, highly regiospecific and orthogonal modification of two chemically identical Cys sites was enabled by the selective recognition property associated with the GST enzyme and the peptide substrate. This result indicates that the GST-catalyzed arylation could greatly expand the scope of previous cysteine modification methods, which necessitate the use of protecting groups or multiple steps to differentially functionalize two or more cysteine residues. In addition, initial experiments with protein substrate showed selective arylation of Cys at N-terminal γ-Glu-Cys-Gly sequence (data not shown).

In addition, experiments with protein substrate showed similar selectivity in arylation of Cys at N-terminal γ-Glu-Cys-Gly sequence. This discovered transformation is not fundametally limited to specific temperatures, solvent conditions and peptides featuring γ-Glu-Cys-Gly sequence. For example, the reaction between 3b and GSH under GST catalysis produces the desired S-arylated product 4b at temperature ranging from 4 to 60° C. (FIG. 37C, right panel), as well as in the presence of up to 20% organic co-solvent (FIG. 37C, left panel). Finally, our experiments show that the N-terminal Glu-Cys-Gly or Asp-Cys-Gly sequences can also be recognized by GST and selectively S-arylated with peptide 3b though with lower efficiency as compared to peptides with N-terminal γ-Glu-Cys-Gly moiety. This observation implies that the requirement for a N-terminal γ-Glutamic acid residue could be potentially circumvented with re-engineered GST.

Cyclic peptides constitute a very important class of medicinally relevant macrocycles. Although various methods to access this class of structures have been previously developed, synthesis of macrocyclic peptide fragments remains challenging. We found intramolecular arylation catalyzed by GST of a peptide containing γ-Glu-Cys-Gly fragment and Cys-III site afforded quantitative conversion of substrate to the cyclized product in less than 30 seconds (FIG. 37B). In contrast, the control experiment without GST produced no product as observed by LCMS analysis. Furthermore, the cyclization reaction was shown to be dominant even with GSH added as a competing substrate (data not shown). The perfluorinated moiety used in this example can potentially enhance the cell-permeability of cyclic peptides as shown previously.

This discovered transformation is not limited to specific temperatures or solvent conditions. The reaction between 3b and GSH under GST catalysis produces the desired S-arylated product 4b at temperature ranging from 4 to 60° C. (FIG. 37C, right panel), as well as in the presence of up to 20% organic co-solvent (FIG. 37C, left panel).

In certain embodiments, the invention relates to a powerful glutathione S-transferase catalyzed $S_NAr$ process for site-specific cysteine modification. In certain embodiments, the inventive methods are ways of selectively modifying cysteine in an N-terminal γ-Glu-Cys-Gly sequence embedded within long peptide chains. The unique chemical orthogonality of the discovered arylation enabled by GST offers an attractive opportunity to modify multiple cysteine sites with different chemical probes or biomolecules avoiding the use of protecting groups and long synthetic procedures.

Exemplary Compounds

In certain embodiments, the invention relates to a compound comprising substructure I:

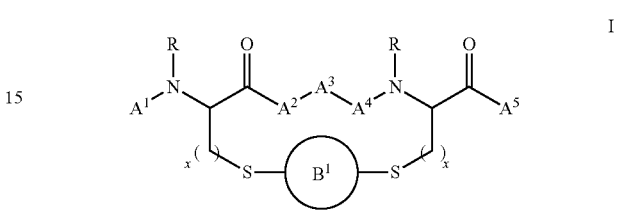

wherein, independently for each occurrence, $A^1$ is H, an amine protecting group, a natural or unnatural amino acid, a peptide, an oligopeptide, a polypeptide, or a protein;

$A^2$, $A^3$, and $A^4$ are selected from the group consisting of a natural amino acid, an unnatural amino acid, and a plurality of natural amino acids or unnatural amino acids;

$A^5$ is OH, a carboxylate protecting group, a natural or unnatural amino acid, a peptide, an oligopeptide, a polypeptide, or a protein;

x is 0, 1, 2, 3, 4, 5, or 6;

is a perfluorinated aryl para-substituted diradical; and

R is H or alkyl.

In certain embodiments, the invention relates to any one of the aforementioned compounds, wherein the compound comprising substructure I is selected from the group consisting of (SEQ ID NOS 7-21, respectively, in order of appearance):

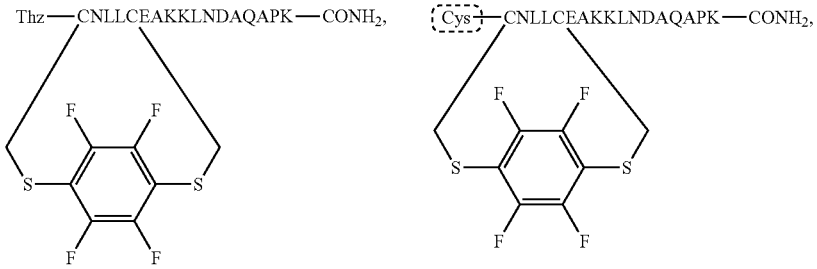

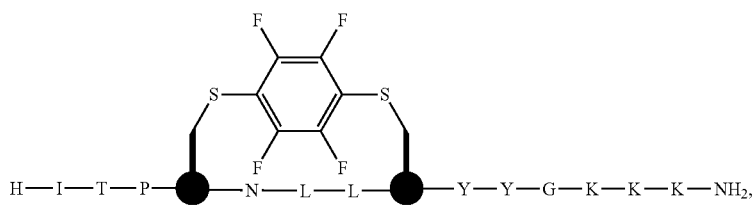

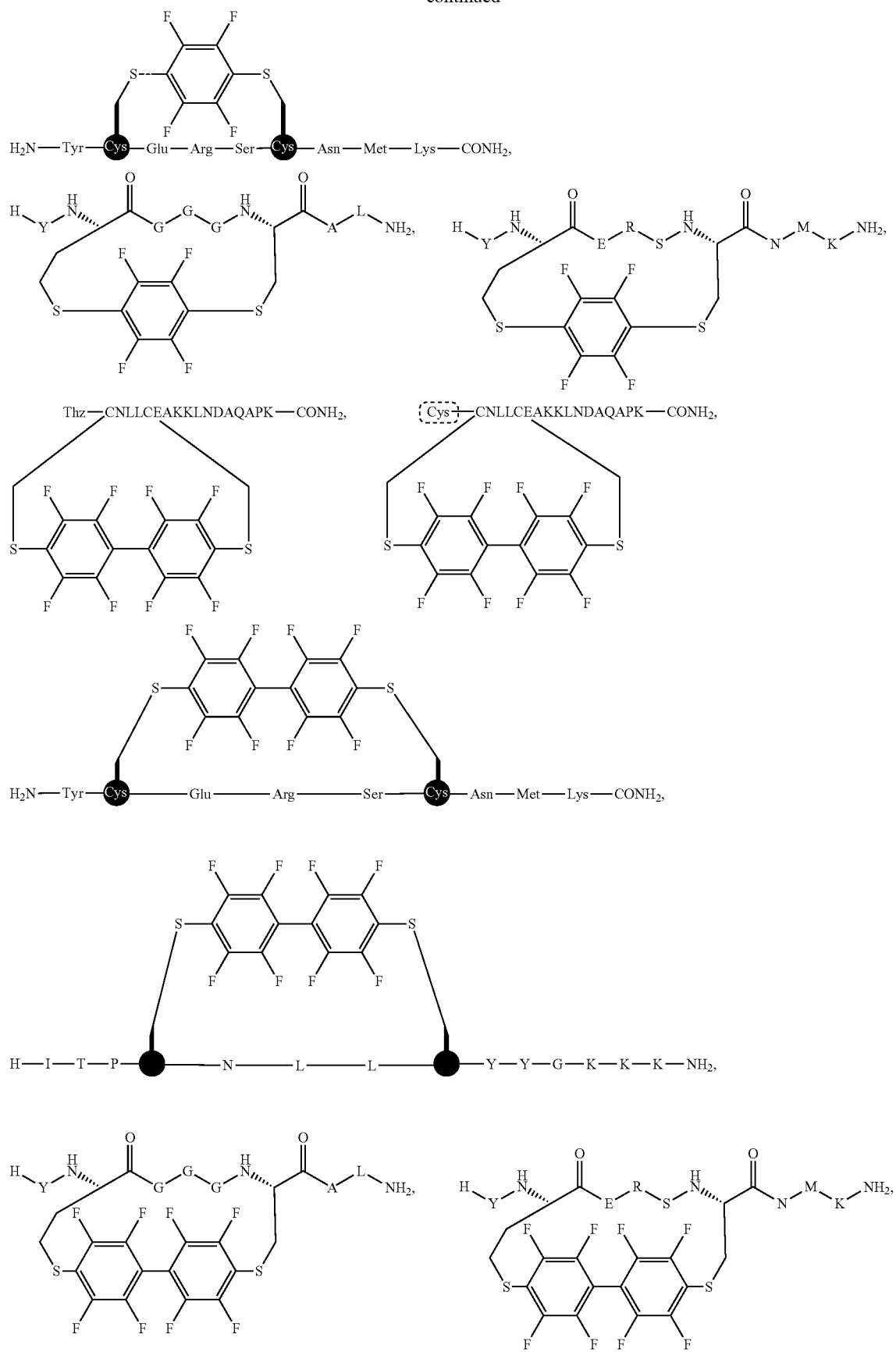

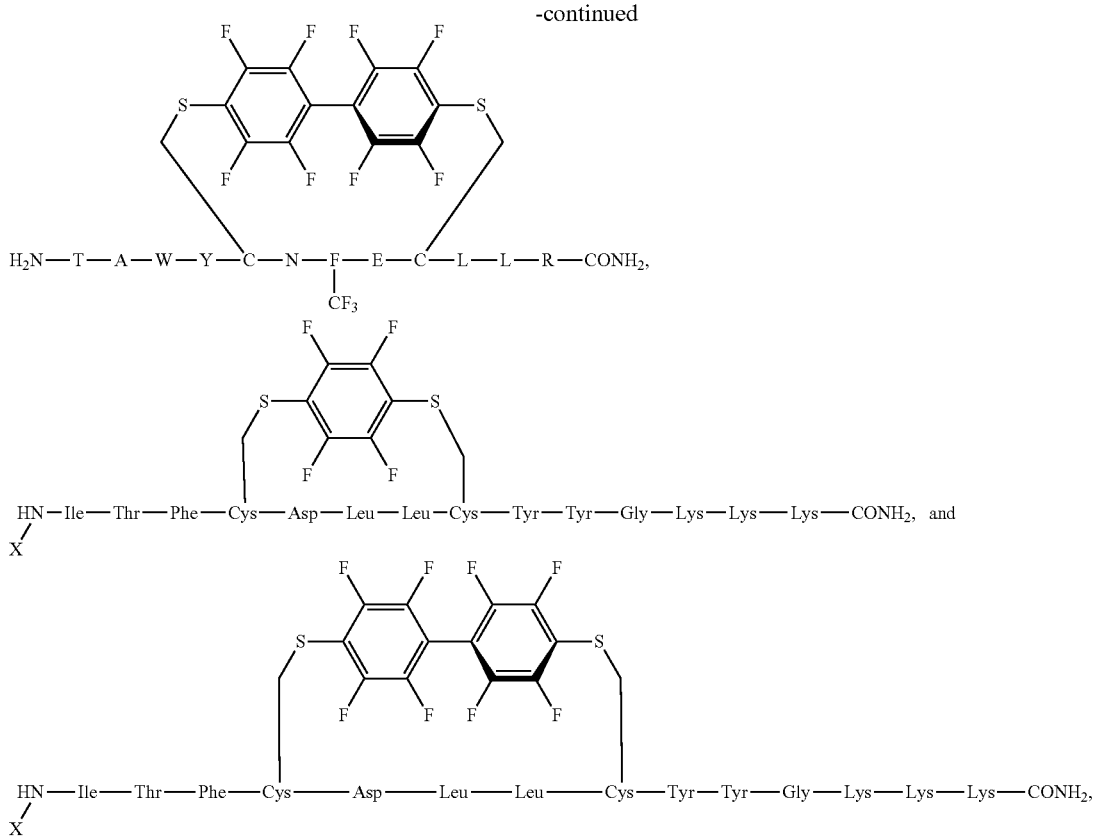

wherein X is H or

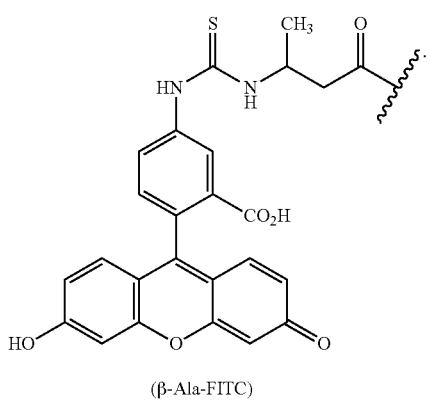 [SMILES: *C(=O)CC(C)NC(=S)Nc1ccc(-c2c3ccc(=O)cc-3oc3cc(O)ccc23)c(C(=O)O)c1]

(β-Ala-FITC)

In certain embodiments, the invention relates to a compound comprising substructure II:

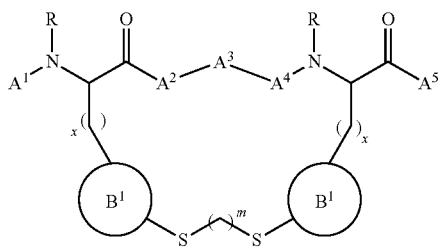

II wherein, independently for each occurrence, $A^1$ is H, an amine protecting group, a natural or unnatural amino acid, a peptide, an oligopeptide, a polypeptide, or a protein;

$A^2$, $A^3$, and $A^4$ are selected from the group consisting of a natural amino acid, an unnatural amino acid, and a plurality of natural amino acids or unnatural amino acids;

$A^5$ is OH, a carboxylate protecting group, a natural or unnatural amino acid, a peptide, an oligopeptide, a polypeptide, or a protein;

$B^1$ is a perfluorinated aryl para-substituted diradical;

m is 1, 2, 3, 4, 5, or 6;

x is 0, 1, 2, 3, 4, 5, or 6; and

R is H or alkyl.

In certain embodiments, the invention relates to any one of the aforementioned compounds, wherein the compound comprising substructure II is selected from the group consisting of (SEQ ID NOS 22-23, respectively, in order of appearance):

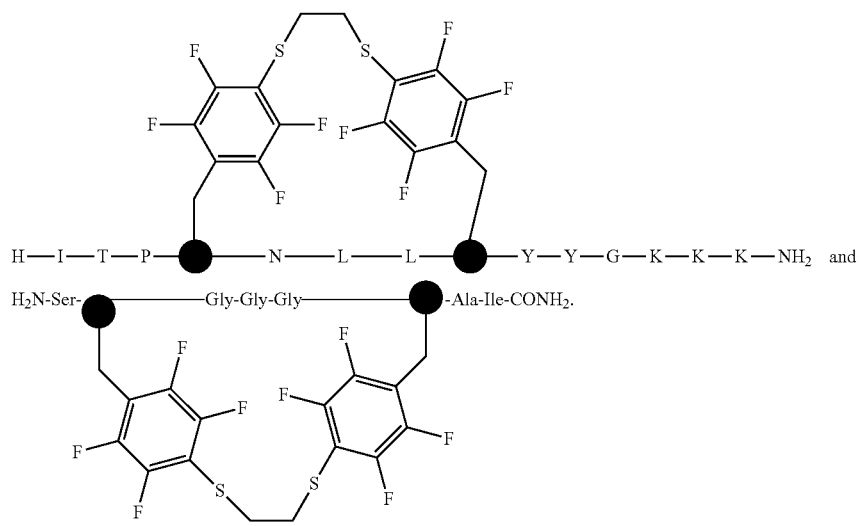

In certain embodiments, the invention relates to a compound comprising substructure III:

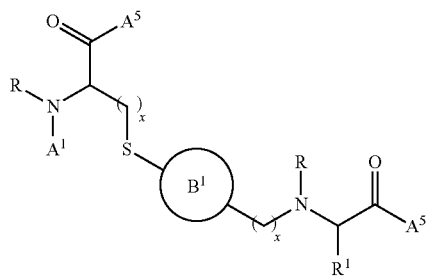

wherein, independently for each occurrence, $A^1$ is H, an amine protecting group, a natural or unnatural amino acid, a peptide, an oligopeptide, a polypeptide, or a protein;

$A^5$ is OH, a carboxylate protecting group, a natural or unnatural amino acid, a peptide, an oligopeptide, a polypeptide, or a protein;

is a perfluorinated aryl para-substituted diradical;

x is 0, 1, 2, 3, 4, 5, or 6;

R is H or alkyl; and $R^1$ is H, alkyl, alkylthioalkyl, aralkyl, heteroaralkyl, hydroxyaralkyl, $HO_2C$-alkyl, $H_2N$—C(O)-alkyl, heterocycloalkyl, guanidinylalkyl, aminoalkyl, or hydroxyalkyl.

In certain embodiments, the invention relates to a compound comprising substructure IV:

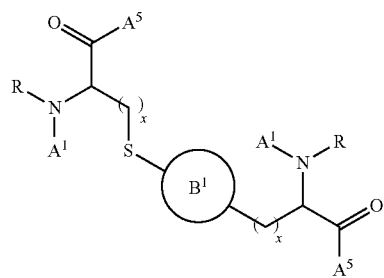

wherein, independently for each occurrence, $A^1$ is H, an amine protecting group, a natural or unnatural amino acid, a peptide, an oligopeptide, a polypeptide, or a protein;

$A^5$ is OH, a carboxylate protecting group, a natural or unnatural amino acid, a peptide, an oligopeptide, a polypeptide, or a protein;

x is 0, 1, 2, 3, 4, 5, or 6;

is a perfluorinated aryl para-substituted diradical; and

R is H or alkyl.

In certain embodiments, the invention relates to a compound comprising substructure V:

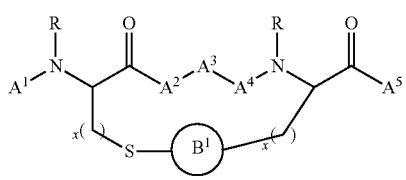

wherein, independently for each occurrence,

A¹ is H, an amine protecting group, a natural or unnatural amino acid, a peptide, an oligopeptide, a polypeptide, or a protein;

A², A³, and A⁴ are selected from the group consisting of a natural amino acid, an unnatural amino acid, and a plurality of natural amino acids or unnatural amino acids;

A⁵ is OH, a carboxylate protecting group, a natural or unnatural amino acid, a peptide, an oligopeptide, a polypeptide, or a protein;

x is 0, 1, 2, 3, 4, 5, or 6;

is a perfluorinated aryl para-substituted diradical; and

R is H or alkyl.

In certain embodiments, the invention relates to a compound comprising substructure VI:

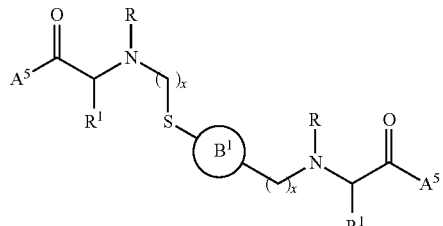

wherein, independently for each occurrence,

A⁵ is OH, a carboxylate protecting group, a natural or unnatural amino acid, a peptide, an oligopeptide, a polypeptide, or a protein;

is a perfluorinated aryl para-substituted diradical;

x is 0, 1, 2, 3, 4, 5, or 6;

R is H or alkyl; and

R¹ is H, alkyl, alkylthioalkyl, aralkyl, heteroaralkyl, hydroxyaralkyl, HO₂C-alkyl, H₂N—C(O)-alkyl, heterocycloalkyl, guanidinylalkyl, aminoalkyl, or hydroxyalkyl.

In certain embodiments, the invention relates to any one of the aforementioned compounds, wherein the compound comprising substructure VI is (SEQ ID NOS 24-25, respectively, in order of appearance)

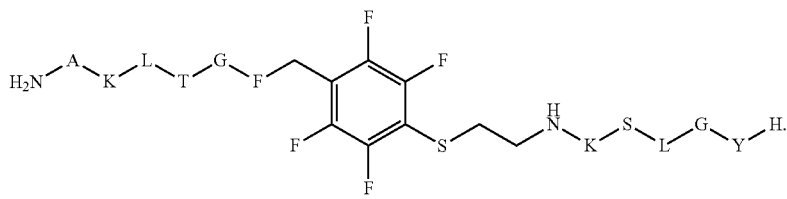

In certain embodiments, the invention relates to a compound comprising substructure VII:

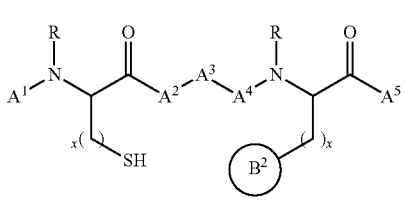

wherein, independently for each occurrence,

A¹ is H, an amine protecting group, a natural or unnatural amino acid, a peptide, an oligopeptide, a polypeptide, or a protein;

A², A³, and A⁴ are selected from the group consisting of a natural amino acid, an unnatural amino acid, and a plurality of natural amino acids or unnatural amino acids;

A⁵ is OH, a carboxylate protecting group, a natural or unnatural amino acid, a peptide, an oligopeptide, a polypeptide, or a protein;

x is 0, 1, 2, 3, 4, 5, or 6;

is a perfluorinated aryl radical; and

R is H or alkyl.

In certain embodiments, the invention relates to a compound comprising substructure VIII:

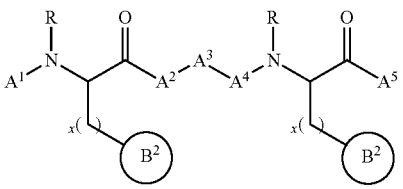

wherein, independently for each occurrence,

A¹ is H, an amine protecting group, a natural or unnatural amino acid, a peptide, an oligopeptide, a polypeptide, or a protein;

A², A³, and A⁴ are selected from the group consisting of a natural amino acid, an unnatural amino acid, and a plurality of natural amino acids or unnatural amino acids;

A⁵ is OH, a carboxylate protecting group, a natural or unnatural amino acid, a peptide, an oligopeptide, a polypeptide, or a protein;

x is 0, 1, 2, 3, 4, 5, or 6;

is a perfluorinated aryl radical; and

R is H or alkyl.

In certain embodiments, the invention relates to any one of the aforementioned compounds, wherein the compound comprising substructure VIII is selected from the group consisting of (SEQ ID NOS 26-27, respectively, in order of appearance):

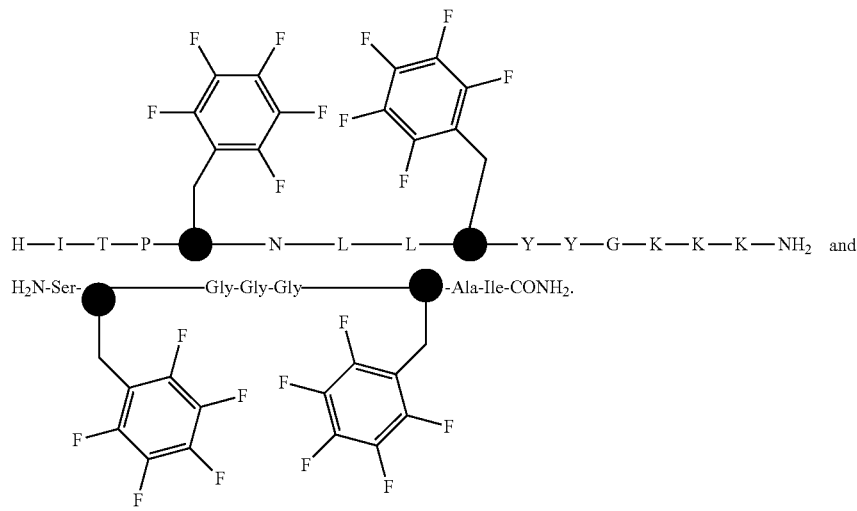

In certain embodiments, the invention relates to a compound comprising substructure IX:

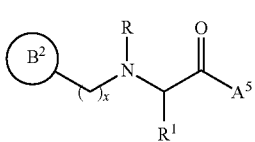

wherein, independently for each occurrence, $A^5$ is OH, a carboxylate protecting group, a natural or unnatural amino acid, a peptide, an oligopeptide, a polypeptide, or a protein;

is a perfluorinated aryl radical;

x is 0, 1, 2, 3, 4, 5, or 6;

R is H or alkyl; and $R^1$ is H, alkyl, alkylthioalkyl, aralkyl, heteroaralkyl, hydroxyaralkyl, $HO_2C$-alkyl, $H_2N$—C(O)-alkyl, heterocycloalkyl, guanidinylalkyl, aminoalkyl, or hydroxyalkyl.

In certain embodiments, the invention relates to any one of the aforementioned compounds, wherein the compound comprising substructure IX is (SEQ ID NO: 28)

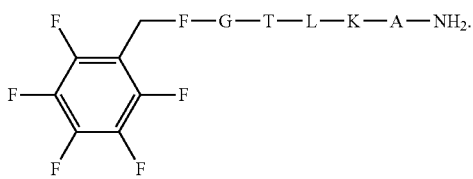

Exact Mass: 814.38

In certain embodiments, the invention relates to a compound comprising substructure X:

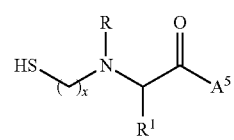

wherein, independently for each occurrence, $A^5$ is OH, a carboxylate protecting group, a natural or unnatural amino acid, a peptide, an oligopeptide, a polypeptide, or a protein;

x is 0, 1, 2, 3, 4, 5, or 6;

R is H or alkyl; and $R^1$ is H, alkyl, alkylthioalkyl, aralkyl, heteroaralkyl, hydroxyaralkyl, $HO_2C$-alkyl, $H_2N$—C(O)-alkyl, heterocycloalkyl, guanidinylalkyl, aminoalkyl, or hydroxyalkyl.

In certain embodiments, the invention relates to any one of the aforementioned compounds, wherein the compound comprising substructure X is (SEQ ID NO: 29)

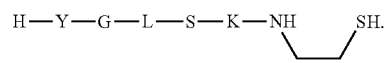

In certain embodiments, the invention relates to a compound comprising substructure XI or substructure XII:

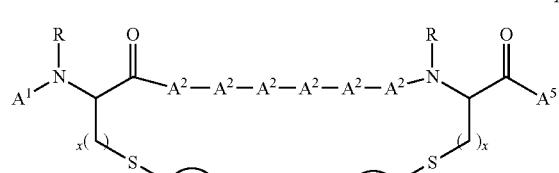

XI

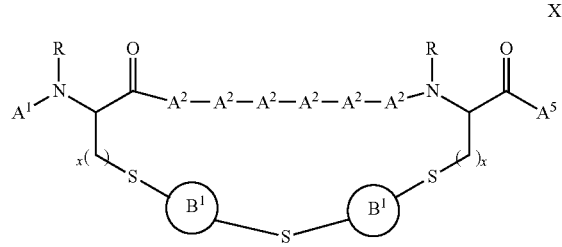

XII wherein, independently for each occurrence,

A¹ is H, an amine protecting group, a natural or unnatural amino acid, a peptide, an oligopeptide, a polypeptide, or a protein;

A² is selected from the group consisting of a natural amino acid, an unnatural amino acid, and a plurality of natural amino acids or unnatural amino acids;

A⁵ is OH, a carboxylate protecting group, a natural or unnatural amino acid, a peptide, an oligopeptide, a polypeptide, or a protein;

is a perfluorinated aryl para-substituted diradical;

x is 0, 1, 2, 3, 4, 5, or 6;

R is H or alkyl; and

L is a substituted or unsubstituted alkyl diradical, a substituted or unsubstituted aryl diradical, or a substituted or unsubstituted aralkyl diradical.

In certain embodiments, the invention relates to any one of the aforementioned compounds, wherein L is —CH₂CH₂—, —(CH₂)₄—, 1,3-phenylene, 1,2-phenylene, 2,3,5,6-tetrafluoro-1,4-phenylene,

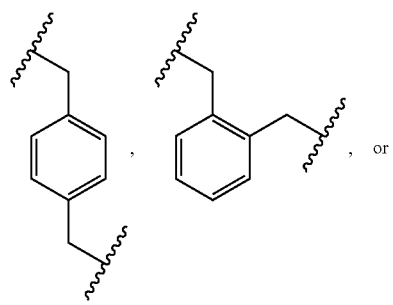

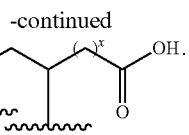

In certain embodiments, the invention relates to any one of the aforementioned compounds, wherein the compound of substructure XI is (SEQ ID NO: 30):

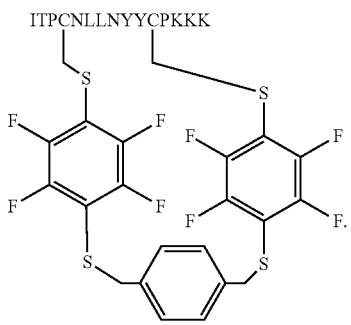

In certain embodiments, the invention relates to any one of the aforementioned compounds, wherein the compound is depicted in the Figures.

In certain embodiments, the invention relates to any one of the aforementioned compounds, wherein A², A³, and A⁴ are natural or unnatural amino acids.

In certain embodiments, the invention relates to any one of the aforementioned compounds, wherein A² represents one natural or unnatural amino acid. In certain embodiments, the invention relates to any one of the aforementioned compounds, wherein A³ represents one natural or unnatural amino acid. In certain embodiments, the invention relates to any one of the aforementioned compounds, wherein A⁴ represents one natural or unnatural amino acid.

In certain embodiments, the invention relates to any one of the aforementioned compounds, wherein A² represents two natural or unnatural amino acids. In certain embodiments, the invention relates to any one of the aforementioned compounds, wherein A³ represents two natural or unnatural amino acids. In certain embodiments, the invention relates to any one of the aforementioned compounds, wherein A⁴ represents two natural or unnatural amino acids.

In certain embodiments, the invention relates to any one of the aforementioned compounds, wherein A² represents three natural or unnatural amino acids. In certain embodiments, the invention relates to any one of the aforementioned compounds, wherein A³ represents three natural or unnatural amino acids. In certain embodiments, the invention relates to any one of the aforementioned compounds, wherein A⁴ represents three natural or unnatural amino acids.

In certain embodiments, the invention relates to any one of the aforementioned compounds, wherein none of A¹, A², A³, A⁴, and A⁵ comprises cysteine. In certain embodiments, the invention relates to any one of the aforementioned compounds, wherein one or more of A¹, A², A³, A⁴, and A⁵ comprises arginine, histidine, lysine, aspartic acid, glutamic acid, serine, threonine, asparagine, glutamine, glycine, proline, alanine, valine, isoleucine, leucine, methionine, phenylalanine, tyrosine, or tryptophan.

In certain embodiments, the invention relates to any one of the aforementioned compounds, wherein A¹ is an amine protecting group selected from the group consisting of an N,O- acetal, allyloxycarbonyl (Aloc), benzyl (Bn), benzyloxycarbonyl (Cbz), benzyloxymethyl (BOM), t-butoxycarbonyl (Boc), t-butyldimethylsilyl (TBDMS), t-butyldiphenylsilyl (TBDPS), diphenylmethyl, diphenylmethylene, ethoxycarbonyl, 9-fluorenylmethoxycarbonyl (Fmoc), p-methoxybenzyl (PMB), methoxycarbonyl, methoxymethyl (MOM), p-methoxyphenyl (PMP), p-nitrocinnamyloxycarbonyl (Noc), tosyl (Ts), 2-tosylethoxycarbonyl (Tsoc), 2,2,2-trichloroethoxycarbonyl (Troc), trifluoroacetyl, triisopropylsilyl (TIPS), trimethylsilyl (TMS), 2-(trimethylsilyl)ethoxycarbonyl (Teoc), 2-(trimethylsilyl)ethoxymethyl (SEM), or trityl (Tr).

In certain embodiments, the invention relates to any one of the aforementioned compounds, wherein $A^5$ is a carboxylate protecting group selected from the group consisting of allyl, benzyl, benzyloxymethyl (BOM), t-Bu, t-butyldimethylsilyl (TBDMS), t-butyldiphenylsilyl (TBDPS), diphenylmethyl, 9-fluorenylmethyl (Fm), 2-methoxyethoxymethyl (MEM), methoxymethyl (MOM), p-nitrobenzyl (PNB), an ester, a 1,3-oxazoline, pivaloyloxymethyl (Pom), 2-tosylethyl (TSE), 2,2,2-trichloroethyl (TCE), triethylsilyl (TES), trimethylsilyl (TMS), 2-(trimethylsilyl)ethoxymethyl (SEM), or 2-(trimethylsilyl)ethyl (TMSE).

In certain embodiments, the invention relates to any one of the aforementioned compounds, wherein $B^1$ is 2,3,5,6-tetrafluorophenylene or 2,2',3,3',5,5',6,6'-octafluoro-1,1'-biphenyl-4,4'-ene.

In certain embodiments, the invention relates to any one of the aforementioned compounds, wherein R is H.

In certain embodiments, the invention relates to any one of the aforementioned compounds, wherein m is 2, 3, or 4.

In certain embodiments, the invention relates to any one of the aforementioned compounds, wherein x is 1, 2, or 3. In certain embodiments, the invention relates to any one of the aforementioned compounds, wherein x is 1.

In certain embodiments, the invention relates to any one of the aforementioned compounds, wherein $R^1$ is aminoalkyl or aralkyl. In certain embodiments, the invention relates to any one of the aforementioned compounds, wherein $R^1$ is —(CH2)$_4$-NH$_2$. In certain embodiments, the invention relates to any one of the aforementioned compounds, wherein $R^1$ is benzyl.

In certain embodiments, the invention relates to any one of the aforementioned compounds, wherein $B^2$ is pentafluorophenyl or 4'-(2,2',3,3',4,5,5',6,6'-nonafluoro-1,1'-biphenyl).

In certain embodiments, the invention relates to any one of the aforementioned compounds, wherein at least one C—F bond has been replaced with a C-Nu bond; and -Nu is —CN, —I, —N$_3$, —OR, —CCR, or —NR$_2$.

In certain embodiments, the invention relates to any one of the compounds described herein.

Exemplary Conjugated Compounds

In certain embodiments, the invention relates to a hybrid composition, wherein the hybrid composition comprises a linker, any one of the aforementioned compounds, and a detectable moiety; and the linker links the compound to the detectable moiety.

In certain embodiments, the invention relates to any one of the aforementioned hybrid compositions, wherein the detectable moiety is a fluorescent moiety, a dye moiety, a radionuclide, or an MRI contrast agent.

In certain embodiments, the invention relates to a hybrid composition, wherein the hybrid composition comprises a linker, any one of the aforementioned compounds, and a biomolecule; and the linker links the compound to the biomolecule.

In certain embodiments, the invention relates to any one of the aforementioned hybrid compositions, wherein the biomolecule is a protein.

In certain embodiments, the invention relates to any one of the aforementioned hybrid compositions, wherein the biomolecule is DNA or RNA.

In certain embodiments, the invention relates to any one of the aforementioned hybrid compositions, wherein the biomolecule is siRNA.

In certain embodiments, the invention relates to any one of the hybrid compositions described herein.

Exemplary Peptides, Oligopeptides, Polypeptides, and Proteins

In certain embodiments, the invention relates to a peptide, an oligopeptide, a polypeptide, or a protein, wherein the peptide, oligopeptides, polypeptide, or protein comprises substructure I, substructure II, substructure III, substructure IV, substructure V, substructure VI, substructure VII, substructure VIII, substructure IX, substructure X, substructure XI, or substructure XII.

In certain embodiments, the invention relates to a peptide, an oligopeptide, a polypeptide, or a protein, wherein the peptide, oligopeptides, polypeptide, or protein comprises a plurality of substructures selected from the group consisting of substructure I, substructure II, substructure III, substructure IV, substructure V, substructure VI, substructure VII, substructure VIII, substructure IX, substructure X, substructure XI, and substructure XII.

In certain embodiments, the invention relates to a peptide, an oligopeptide, a polypeptide, or a protein, wherein the peptide, oligopeptides, polypeptide, or protein comprises substructure I, substructure II, substructure III, substructure IV, substructure V, substructure VI, substructure XI, or substructure XII.

In certain embodiments, the invention relates to a peptide, an oligopeptide, a polypeptide, or a protein, wherein the peptide, oligopeptides, polypeptide, or protein comprises a plurality of substructures selected from the group consisting of substructure I, substructure II, substructure III, substructure IV, substructure V, substructure VI, substructure XI, and substructure XII.

In certain embodiments, the invention relates to any one of the peptides, oligopeptides, polypeptides, or proteins described herein.

Exemplary Affibodies

In certain embodiments, the invention relates to an affibody comprising substructure I, substructure II, substructure III, substructure IV, substructure V, substructure VI, substructure VII, substructure VIII, substructure IX, substructure X, substructure XI, or substructure XII.

In certain embodiments, the invention relates to an affibody comprising a plurality of substructures selected from the group consisting of substructure I, substructure II, substructure III, substructure IV, substructure V, substructure VI, substructure VII, substructure VIII, substructure IX, substructure X, substructure XI, and substructure XII.

In certain embodiments, the invention relates to an affibody comprising substructure I, substructure II, substructure III, substructure IV, substructure V, substructure VI, substructure XI, or substructure XII.

In certain embodiments, the invention relates to an affibody comprising a plurality of substructures selected from the group consisting of substructure I, substructure II, substructure III, substructure IV, substructure V, substructure VI, substructure X, substructure XI, and substructure XII.

As used herein the term "affibody" refers to a small protein composed of alpha helices. In certain embodiments, the affibody is engineered to bind a target protein or target peptide with high affinity. In certain embodiments, affibodies are antibody mimetics. In certain embodiments, affibodies lack disulfide bridges. In certain embodiments, the affibody comprises a three-helix bundle. In certain embodiments, the affibody has a molar mass of less than about 8 kDa. In certain embodiments, the affibody has a molar mass of about 6 kDa.

In certain embodiments, the invention relates to any one of the affibodies described herein.

Exemplary Methods

In certain embodiments, the invention relates to a method of making a compound comprising substructure I, according to Scheme 1:

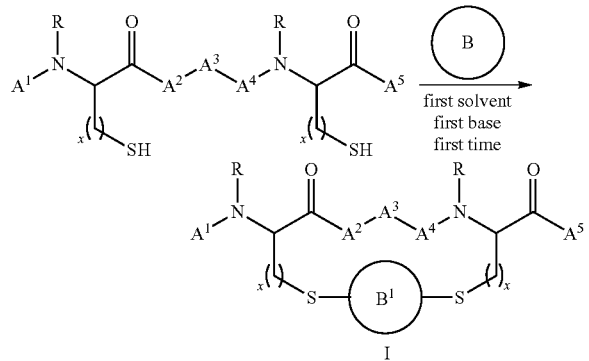

wherein, independently for each occurrence, $A^1$ is H, an amine protecting group, a natural or unnatural amino acid, a peptide, an oligopeptide, a polypeptide, or a protein;

$A^2$, $A^3$, and $A^4$ are selected from the group consisting of a natural amino acid, an unnatural amino acid, and a plurality of natural amino acids or unnatural amino acids;

$A^5$ is OH, a carboxylate protecting group, a natural or unnatural amino acid, a peptide, an oligopeptide, a polypeptide, or a protein;

x is 0, 1, 2, 3, 4, 5, or 6;

R is H or alkyl;

is a perfluorinated aryl compound; and

is a perfluorinated aryl para-substituted diradical.

In certain embodiments, the invention relates to a method of making a compound comprising substructure II, according to Scheme 2:

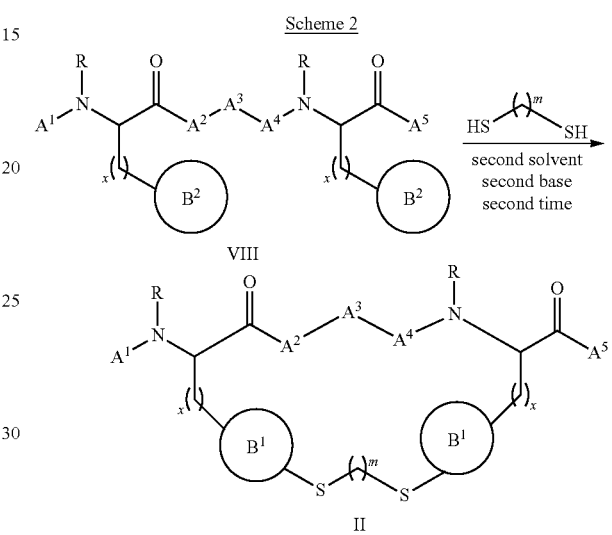

wherein, independently for each occurrence, $A^1$ is H, an amine protecting group, a natural or unnatural amino acid, a peptide, an oligopeptide, a polypeptide, or a protein;

$A^2$, $A^3$, and $A^4$ are selected from the group consisting of a natural amino acid, an unnatural amino acid, and a plurality of natural amino acids or unnatural amino acids;

$A^5$ is OH, a carboxylate protecting group, a natural or unnatural amino acid, a peptide, an oligopeptide, a polypeptide, or a protein;

R is H or alkyl;

x is 0, 1, 2, 3, 4, 5, or 6;

is a perfluorinated aryl radical;

m is 1, 2, 3, 4, 5, or 6; and

is a perfluorinated aryl para-substituted diradical.

In certain embodiments, the invention relates to a method of making a compound comprising substructure III, according to Scheme 3:

Scheme 3

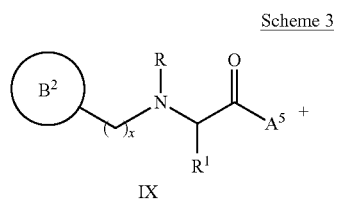

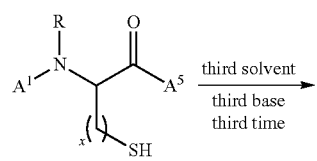

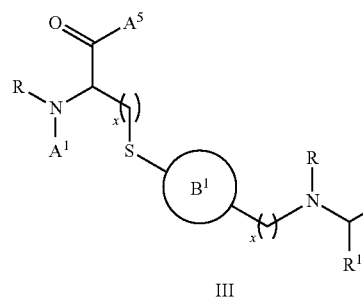

wherein, independently for each occurrence, $A^1$ is H, an amine protecting group, a natural or unnatural amino acid, a peptide, an oligopeptide, a polypeptide, or a protein;

$A^5$ is OH, a carboxylate protecting group, a natural or unnatural amino acid, a peptide, an oligopeptide, a polypeptide, or a protein;

R is H or alkyl;

x is 0, 1, 2, 3, 4, 5, or 6;

is a perfluorinated aryl radical;

$R^1$ is H, alkyl, alkylthioalkyl, aralkyl, heteroaralkyl, hydroxyaralkyl, $HO_2C$-alkyl, $H_2N$—C(O)-alkyl, heterocycloalkyl, guanidinylalkyl, aminoalkyl, or hydroxyalkyl; and

is a perfluorinated aryl para-substituted diradical.

In certain embodiments, the invention relates to a method of making a compound comprising substructure IV, according to Scheme 4:

Scheme 4

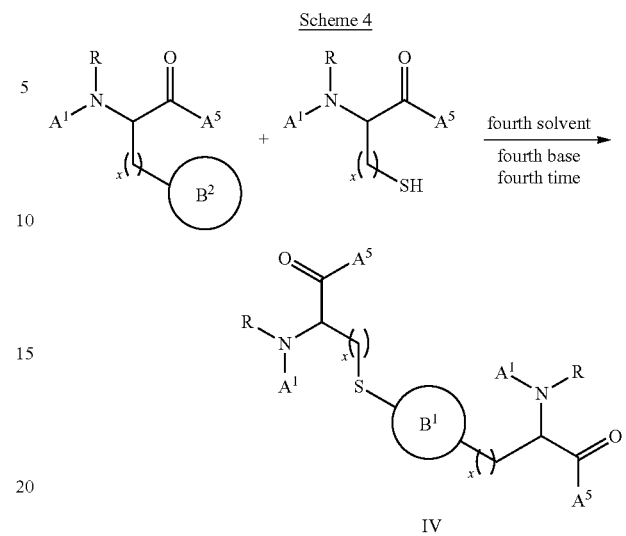

wherein, independently for each occurrence, $A^1$ is H, an amine protecting group, a natural or unnatural amino acid, a peptide, an oligopeptide, a polypeptide, or a protein;

$A^5$ is OH, a carboxylate protecting group, a natural or unnatural amino acid, a peptide, an oligopeptide, a polypeptide, or a protein;

R is H or alkyl;

x is 0, 1, 2, 3, 4, 5, or 6;

is a perfluorinated aryl radical; and

is a perfluorinated aryl para-substituted diradical.

In certain embodiments, the invention relates to a method of making a compound comprising substructure V, according to Scheme 5:

Scheme 5

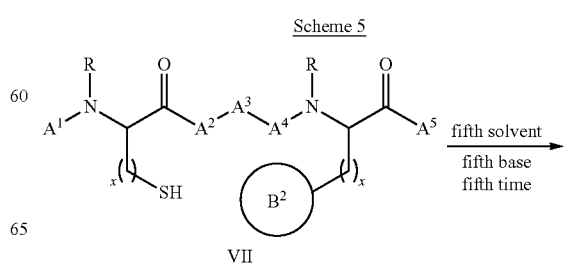

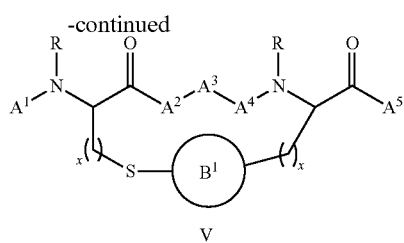

wherein, independently for each occurrence,

A¹ is H, an amine protecting group, a natural or unnatural amino acid, a peptide, an oligopeptide, a polypeptide, or a protein;

A², A³, and A⁴ are selected from the group consisting of a natural amino acid, an unnatural amino acid, and a plurality of natural amino acids or unnatural amino acids;

A⁵ is OH, a carboxylate protecting group, a natural or unnatural amino acid, a peptide, an oligopeptide, a polypeptide, or a protein;

R is H or alkyl;

x is 0, 1, 2, 3, 4, 5, or 6;

is a perfluorinated aryl radical; and

is a perfluorinated aryl para-substituted diradical.

In certain embodiments, the invention relates to a method of making a compound comprising substructure VI, according to Scheme 6:

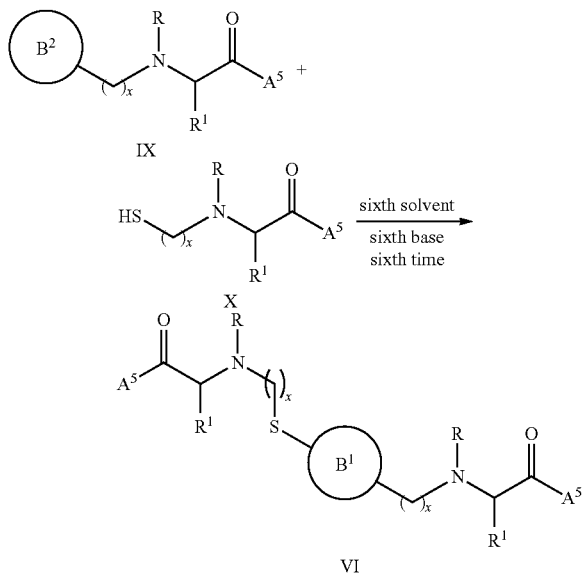

wherein, independently for each occurrence,

A⁵ is OH, a carboxylate protecting group, a natural or unnatural amino acid, a peptide, an oligopeptide, a polypeptide, or a protein;

R is H or alkyl;

x is 0, 1, 2, 3, 4, 5, or 6;

R¹ is H, alkyl, alkylthioalkyl, aralkyl, heteroaralkyl, hydroxyaralkyl, HO₂C-alkyl, H₂N—C(O)-alkyl, heterocycloalkyl, guanidinylalkyl, aminoalkyl, or hydroxyalkyl;

is a perfluorinated aryl radical; and

is a perfluorinated aryl para-substituted diradical.

In certain embodiments, the invention relates to a method of making a compound according to Scheme 7:

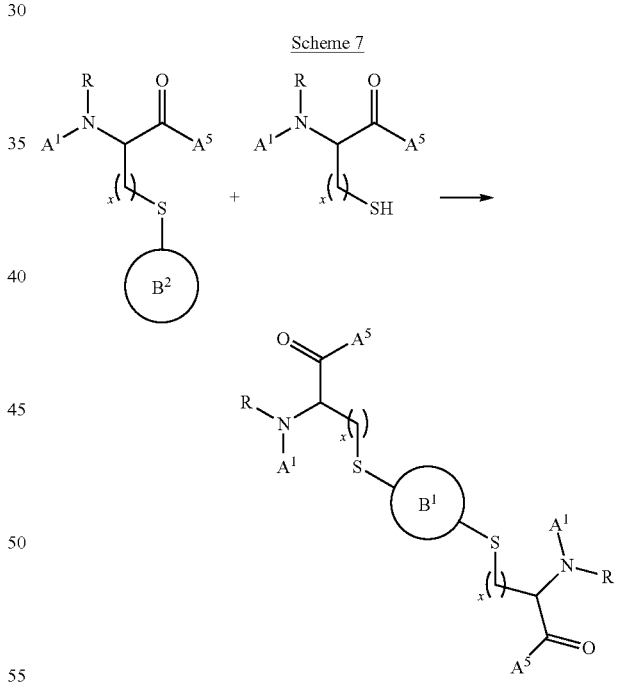

wherein, independently for each occurrence,

A¹ is H, an amine protecting group, a natural or unnatural amino acid, a peptide, an oligopeptide, a polypeptide, or a protein;

A⁵ is OH, a carboxylate protecting group, a natural or unnatural amino acid, a peptide, an oligopeptide, a polypeptide, or a protein;

R is H or alkyl;

x is 0, 1, 2, 3, 4, 5, or 6;

is a perfluorinated aryl radical; and

is a perfluorinated aryl para-substituted diradical.

In certain embodiments, the invention relates to any one of the aforementioned methods, further comprising adding a catalyst. In certain embodiments, the catalyst is glutathione S-transferase (GST). In certain embodiments, the GST is intracellular GST.

In certain embodiments, the invention relates to any one of the aforementioned methods, wherein the reaction takes place in vivo.

In certain embodiments, the invention relates to any one of the aforementioned methods, wherein the product is a hybrid biopolymer.

In certain embodiments, the invention relates to any one of the aforementioned methods, wherein $A^2$, $A^3$, and $A^4$ are natural or unnatural amino acids.

In certain embodiments, the invention relates to any one of the aforementioned methods, wherein $A^2$ represents one natural or unnatural amino acid. In certain embodiments, the invention relates to any one of the aforementioned methods, wherein $A^3$ represents one natural or unnatural amino acid. In certain embodiments, the invention relates to any one of the aforementioned methods, wherein $A^4$ represents one natural or unnatural amino acid.

In certain embodiments, the invention relates to any one of the aforementioned methods, wherein $A^2$ represents two natural or unnatural amino acids. In certain embodiments, the invention relates to any one of the aforementioned methods, wherein $A^3$ represents two natural or unnatural amino acids. In certain embodiments, the invention relates to any one of the aforementioned methods, wherein $A^4$ represents two natural or unnatural amino acids.

In certain embodiments, the invention relates to any one of the aforementioned methods, wherein $A^2$ represents three natural or unnatural amino acids. In certain embodiments, the invention relates to any one of the aforementioned methods, wherein $A^3$ represents three natural or unnatural amino acids. In certain embodiments, the invention relates to any one of the aforementioned methods, wherein $A^4$ represents three natural or unnatural amino acids.

In certain embodiments, the invention relates to any one of the aforementioned methods, wherein the first solvent, the second solvent, the third solvent, the fourth solvent, the fifth solvent, or the sixth solvent is DMF, $CH_3CN$, $CH_3OH$, DMSO, tris(2-carboxyethyl)phosphine (TCEP), dibutyl ether, tetrahydrofuran (THF), 1,4-dioxane, DME, dichloromethane, dichloroethane, acetone, diethyl ether, hexanes, or a mixture thereof.

In certain embodiments, the invention relates to any one of the aforementioned methods, wherein the first base, the second base, the third base, the fourth base, the fifth base, or the sixth base is triethylamine, $Na_3PO_4$, or tris(hydroxymethyl)aminomethane (TRIS).

In certain embodiments, the invention relates to any one of the aforementioned methods, wherein the first time, the second time, the third time, the fourth time, the fifth time, or the sixth time is from about 30 min to about 24 h. In certain embodiments, the invention relates to any one of the aforementioned methods, wherein the first time, the second time, the third time, the fourth time, the fifth time, or the sixth time is about 1 h, about 2 h, about 3 h, about 4 h, about 5 h, about 6 h, about 7 h, about 8 h, about 9 h, about 10 h, about 11 h, about 12 h, about 13 h, about 14 h, or about 15 h.

In certain embodiments, the invention relates to any one of the aforementioned methods, wherein none of $A^1$, $A^2$, $A^3$, $A^4$, and $A^5$ comprises cysteine. In certain embodiments, the invention relates to any one of the aforementioned methods, wherein one or more of $A^1$, $A^2$, $A^3$, $A^4$, and $A^5$ comprises arginine, histidine, lysine, aspartic acid, glutamic acid, serine, threonine, asparagine, glutamine, glycine, proline, alanine, valine, isoleucine, leucine, methionine, phenylalanine, tyrosine, or tryptophan.

In certain embodiments, the invention relates to any one of the aforementioned methods, wherein $A^1$ is an amine protecting group selected from the group consisting of an N,O-acetal, allyloxycarbonyl (Aloc), benzyl (Bn), benzyloxycarbonyl (Cbz), benzyloxymethyl (BOM), t-butoxycarbonyl (Boc), t-butyldimethylsilyl (TBDMS), t-butyldiphenylsilyl (TBDPS), diphenylmethyl, diphenylmethylene, ethoxycarbonyl, 9-fluorenylmethoxycarbonyl (Fmoc), p-methoxybenzyl (PMB), methoxycarbonyl, methoxymethyl (MOM), p-methoxyphenyl (PMP), p-nitrocinnamyloxycarbonyl (Noc), tosyl (Ts), 2-tosylethoxycarbonyl (Tsoc), 2,2,2-trichloroethoxycarbonyl (Troc), trifluoroacetyl, triisopropylsilyl (TIPS), trimethylsilyl (TMS), 2-(trimethylsilyl)ethoxycarbonyl (Teoc), 2-(trimethylsilyl)ethoxymethyl (SEM), or trityl (Tr).

In certain embodiments, the invention relates to any one of the aforementioned methods, wherein $A^5$ is a carboxylate protecting group selected from the group consisting of allyl, benzyl, benzyloxymethyl (BOM), t-Bu, t-butyldimethylsilyl (TBDMS), t-butyldiphenylsilyl (TBDPS), diphenylmethyl, 9-fluorenylmethyl (Fm), 2-methoxyethoxymethyl (MEM), methoxymethyl (MOM), p-nitrobenzyl (PNB), an ester, a 1,3-oxazoline, pivaloyloxymethyl (Pom), 2-tosylethyl (TSE), 2,2,2-trichloroethyl (TCE), triethylsilyl (TES), trimethylsilyl (TMS), 2-(trimethylsilyl)ethoxymethyl (SEM), or 2-(trimethylsilyl)ethyl (TMSE).

In certain embodiments, the invention relates to any one of the aforementioned methods, wherein

is hexafluorophenyl or decafluorobiphenyl.

In certain embodiments, the invention relates to any one of the aforementioned methods, wherein

is 2,3,5,6-tetrafluorophenylene or 2,2',3,3',5,5',6,6'-octafluoro-1,1'-biphenyl-4,4'-ene.

In certain embodiments, the invention relates to any one of the aforementioned methods, wherein R is H.

In certain embodiments, the invention relates to any one of the aforementioned methods, wherein m is 2, 3, or 4.

In certain embodiments, the invention relates to any one of the aforementioned methods, wherein x is 1, 2, or 3. In certain embodiments, the invention relates to any one of the aforementioned methods, wherein x is 1.

In certain embodiments, the invention relates to any one of the aforementioned methods, wherein $R^1$ is aminoalkyl or aralkyl. In certain embodiments, the invention relates to any one of the aforementioned methods, wherein $R^1$ is —$(CH_2)_4$—$NH_2$. In certain embodiments, the invention relates to any one of the aforementioned methods, wherein $R^1$ is benzyl.

In certain embodiments, the invention relates to any one of the aforementioned methods, wherein $$B^2$$

is pentafluorophenyl or 4'-(2,2',3,3',4,5,5',6,6'-nonafluoro-1,1'-biphenyl).

In certain embodiments, the invention relates to any one of the aforementioned methods, wherein the temperature is between about 10° C. and about 50° C. In certain embodiments, the invention relates to any one of the aforementioned methods, wherein the temperature is about 16° C., about 17° C., about 18° C., about 19° C., about 20° C., about 21° C., about 22° C., about 23° C., about 24° C., or about 25° C.

The reactions typically proceed at mild temperatures and pressures to give high yields of the product. Thus, yields of desired products greater than 45%, greater than 75%, greater than 80%, greater than 85%, greater than 90%, or greater than 95% may be obtained from reactions at mild temperatures according to the invention.

In certain embodiments, the reactions take place under an inert atmosphere of a gas such as nitrogen or argon.

The reaction processes of the invention can be conducted in continuous, semi-continuous or batch fashion and may involve a liquid recycle operation as desired. The processes of this invention are preferably conducted in batch fashion. Likewise, the manner or order of addition of the reaction ingredients, base, and solvent are not generally critical to the success of the reaction, and may be accomplished in any conventional fashion.

The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. When complete conversion is not desired or not obtainable, the starting materials can be separated from the product and then recycled back into the reaction zone.

The processes may be conducted in glass lined, stainless steel, fluoropolymer coated (e.g., Teflon coated) or similar type reaction equipment. The reaction zone may be fitted with one or more internal and/or external heat exchanger(s) in order to control undue temperature fluctuations, or to prevent any possible "runaway" reaction temperatures.

Furthermore, one or more of the reactants can be immobilized on or incorporated into a polymer or other insoluble matrix by, for example, derivatization with one or more of the substituents of the aryl group or an amino acid residue.

The ability to provide synthesis schemes for the compounds of the invention that can be carried out under mild conditions has broad application.

In addition, the subject methods can be used as part of combinatorial synthesis schemes to yield libraries of compounds. Accordingly, another aspect of the invention relates to use of the subject method to generate variegated libraries of compounds, and to the libraries themselves. The libraries can be soluble or linked to insoluble supports, e.g., through a substituent of a reactant (prior to carrying out a reaction of the invention).

Further, the methods of the invention can be used to produce synthetic intermediates that, after being subjected to additional methods known in the art, are transformed to desired end products.

Exemplary Therapeutic Methods

In certain embodiments, the invention relates to a method of disrupting or inhibiting the p53/MDM2 interaction in a cell comprising the step of:

contacting the cell with an effective amount of any one of the aforementioned compounds, thereby disrupting or inhibiting the p53/MDM2 interaction.

In certain embodiments, the invention relates to a method of enhancing the activity of p53 in a cell comprising the step of:

contacting the cell with an effective amount of any one of the aforementioned compounds, thereby enhancing the activity of p53.

In certain embodiments, the invention relates to any one of the aforementioned methods, wherein the method is a method of prolonging the half-life of p53, as compared to the half-life of p53 in the absence of the compound under the same experimental conditions.

In certain embodiments, the invention relates to any one of the aforementioned methods, wherein the cell is a cancer cell.

In certain embodiments, the invention relates to any one of the aforementioned methods, wherein the cell is a glioblastoma cell.

In certain embodiments, the invention relates to a method of a disease in a subject in need thereof comprising the step of:

administering to the subject an effective amount of any one of the aforementioned compounds, thereby treating the disease.

In certain embodiments, the invention relates to any one of the aforementioned methods, wherein the disease is cancer. In one group of embodiments, the invention relates to any one of the aforementioned methods, wherein the disease is selected from the group consisting of breast cancer, prostate cancer, lymphoma, skin cancer, pancreatic cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma. In some embodiments, the cancer being treated is metastatic. In other embodiments, the cancer being treated is resistant to anticancer agents.

In certain embodiments, the disease is a tumor that is deficient in the p53 protein. The p53 protein is a tumor suppressor protein that is encoded in humans by the TP53 gene. The p53 protein regulates the cell cycle and therefore functions as a tumor suppressor that is involved in preventing cancer. Involvement of mutations in the p53 gene and human tumor types can be found in Nature, 1989, 342:705-708.

In certain embodiments, the invention relates to any one of the aforementioned methods, further comprising the step of: monitoring the cell or the subject by $^{19}F$ NMR.

A subject in need thereof (or a mammal in need thereof) may include, for example, a subject who has been diagnosed with any one of the aforementioned diseases, or a subject who has been treated for any one of the aforementioned diseases, including subjects that have been refractory to the previous treatment.

In some embodiments, the subject pharmaceutical compositions of the present invention will incorporate the substance or substances to be delivered in an amount sufficient to deliver to a patient a therapeutically effective amount of an incorporated therapeutic agent or other material as part of a prophylactic or therapeutic treatment. The desired concentration of the active agent will depend on absorption, inactivation, and excretion rates of the drug as well as the delivery rate of the compound. It is to be noted that dosage values may also vary with the severity of the condition to be alleviated. It is to be further understood that for any particular subject, specific dosage regimens should be adjusted over time according to the individual need and the professional judgment of the person administering or supervising the administration of the compositions. Typically, dosing will be determined using techniques known to one skilled in the art.

The dosage of the subject agent may be determined by reference to the plasma concentrations of the agent. For example, the maximum plasma concentration ($C_{max}$) and the area under the plasma concentration-time curve from time 0 to infinity (AUC (0-4)) may be used. Dosages for the present invention include those that produce the above values for $C_{max}$ and AUC (0-4) and other dosages resulting in larger or smaller values for those parameters.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular agent employed, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could prescribe and/or administer doses of the agents of the invention employed in the pharmaceutical composition at levels lower than that required in order to achieve the desired therapeutic effect and gradually increase the dosage until the desired effect is achieved.

In general, a suitable daily dose of an agent of the invention will be that amount of the agent which is the lowest dose effective to produce a therapeutic effect. Such an effective dose will generally depend upon the factors described above.

If desired, the effective daily dose of the agent may be administered as two, three, four, five, six or more sub-doses administered separately at appropriate intervals throughout the day, optionally, in unit dosage forms.

The precise time of administration and amount of any particular agent that will yield the most effective treatment in a given patient will depend upon the activity, pharmacokinetics, and bioavailability of a particular agent, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

While the subject is being treated, the health of the subject may be monitored by measuring one or more of the relevant indices at predetermined times during a 24-hour period. All aspects of the treatment, including supplements, amounts, times of administration and formulation, may be optimized according to the results of such monitoring. The patient may be periodically reevaluated to determine the extent of improvement by measuring the same parameters, the first such reevaluation typically occurring at the end of four weeks from the onset of therapy, and subsequent reevaluations occurring every four to eight weeks during therapy and then every three months thereafter. Therapy may continue for several months or even years, with a minimum of one month being a typical length of therapy for humans. Adjustments, for example, to the amount(s) of agent administered and to the time of administration may be made based on these reevaluations.

Treatment may be initiated with smaller dosages which are less than the optimum dose of the compound. Thereafter, the dosage may be increased by small increments until the optimum therapeutic effect is attained. In addition, the combined use an agent that modulates an autotrophy-associated gene product and a second agent, e.g., another agent useful for the treatment of the autophagy-related disease, may reduce the required dosage for any individual agent because the onset and duration of effect of the different compounds and/or agents may be complimentary.

In one aspect of the invention, a compound of the invention, or a pharmaceutically acceptable salt thereof, can be used alone or in combination with another therapeutic agent to treat diseases such cancer. It should be understood that the compounds of the invention can be used alone or in combination with an additional agent, e.g., a therapeutic agent, said additional agent being selected by the skilled artisan for its intended purpose. For example, the additional agent can be a therapeutic agent that is art-recognized as being useful to treat the disease or condition being treated by the compound of the present invention. The additional agent also can be an agent that imparts a beneficial attribute to the therapeutic composition e.g., an agent that affects the viscosity of the composition.

The combination therapy contemplated by the invention includes, for example, administration of a compound of the invention, or a pharmaceutically acceptable salt thereof, and additional agent(s) in a single pharmaceutical formulation as well as administration of a compound of the invention, or a pharmaceutically acceptable salt thereof, and additional agent(s) in separate pharmaceutical formulations. In other words, co-administration shall mean the administration of at least two agents to a subject so as to provide the beneficial effects of the combination of both agents. For example, the agents may be administered simultaneously or sequentially over a period of time.

It should further be understood that the combinations included within the invention are those combinations useful for their intended purpose. The agents set forth below are illustrative for purposes and not intended to be limited. The combinations, which are part of this invention, can be the compounds of the present invention and at least one additional agent selected from the lists below. The combination can also include more than one additional agent, e.g., two or three additional agents if the combination is such that the formed composition can perform its intended function.

In certain embodiments, the co-administration of two or more therapeutic agents achieves a synergistic effect, i.e., a therapeutic effect that is greater than the sum of the therapeutic effects of the individual components of the combination. The term "synergistic" refers to a combination which is more effective than the additive effects of any two or more single agents. A synergistic effect permits the effective treatment of a disease using lower amounts (doses) of individual therapy. The lower doses result in lower toxicity without reduced efficacy. In addition, a synergistic effect can result in improved efficacy. Finally, synergy may result in an improved avoidance or reduction of disease as compared to any single therapy. Combination therapy can allow for the product of lower doses of the first therapeutic or the second therapeutic agent (referred to as "apparent one-way synergy" herein), or lower doses of both therapeutic agents (referred to as "two-way synergy" herein) than would normally be required when either drug is used alone.

Definitions

For convenience, certain terms employed in the specification, examples, and appended claims are collected here.

The articles "a" and "an" are used herein to refer to one or to more than one (i.e., to at least one) of the grammatical object of the article. By way of example, "an element" means one element or more than one element.

The term "heteroatom" is art-recognized and refers to an atom of any element other than carbon or hydrogen. Illustrative heteroatoms include boron, nitrogen, oxygen, phosphorus, sulfur and selenium.

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxycarbonyl" means an alkoxy group, as defined herein, appended to the parent molecular moiety through a carbonyl group, represented by —C(C=O)—, as defined herein. Representative examples of alkoxycarbonyl include, but are not limited to, methoxycarbonyl, ethoxycarbonyl, and tert-butoxycarbonyl.

The term "alkoxysulfonyl" as used herein, means an alkoxy group, as defined herein, appended to the parent molecular moiety through a sulfonyl group, as defined herein. Representative examples of alkoxysulfonyl include, but are not limited to, methoxysulfonyl, ethoxysulfonyl and propoxysulfonyl.

The term "arylalkoxy" and "heteroalkoxy" as used herein, means an aryl group or heteroaryl group, as defined herein, appended to the parent molecular moiety through an alkoxy group, as defined herein.

The term "alkyl" means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

The term "alkylcarbonyl" as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonyloxy" and "arylcarbonyloxy" as used herein, means an alkylcarbonyl or arylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy. Representative examples of arylcarbonyloxy include, but are not limited to phenylcarbonyloxy.

The term "alkylsulfonyl" as used herein, means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylthio" as used herein, means an alkyl group, as defined herein, appended to the parent molecular moiety through a sulfur atom. Representative examples of alkylthio include, but are not limited, methylthio, ethylthio, tert-butylthio, and hexylthio. The terms "arylthio," "alkenylthio" and "arylakylthio," for example, are likewise defined.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "amido" as used herein, means —NHC(=O)—, wherein the amido group is bound to the parent molecular moiety through the nitrogen. Examples of amido include alkylamido such as $CH_3C(=O)N(H)—$ and $CH_3CH_2C(=O)N(H)—$.

The term "amino" as used herein, refers to radicals of both unsubstituted and substituted amines appended to the parent molecular moiety through a nitrogen atom. The two groups are each independently hydrogen, alkyl, alkylcarbonyl, alkylsulfonyl, arylcarbonyl, or formyl. Representative examples include, but are not limited to methylamino, acetylamino, and acetylmethylamino.

The term "aromatic" refers to a planar or polycyclic structure characterized by a cyclically conjugated molecular moiety containing 4n+2 electrons, wherein n is the absolute value of an integer. Aromatic molecules containing fused, or joined, rings also are referred to as bicyclic aromatic rings. For example, bicyclic aromatic rings containing heteroatoms in a hydrocarbon ring structure are referred to as bicyclic heteroaryl rings.

The term "aryl," as used herein, means a phenyl group or a naphthyl group. The aryl groups of the invention can be optionally substituted with 1, 2, 3, 4 or 5 substituents independently selected from the group consisting of alkenyl, alkoxy, alkoxycarbonyl, alkoxysulfonyl, alkyl, alkylcarbonyl, alkylcarbonyloxy, alkylsulfonyl, alkylthio, alkynyl, amido, amino, carboxy, cyano, formyl, halo, haloalkoxy, haloalkyl, hydroxyl, hydroxyalkyl, mercapto, nitro, phosphinyl, silyl and silyloxy.

The term "arylene," is art-recognized, and as used herein, pertains to a bidentate moiety obtained by removing two hydrogen atoms of an aryl ring, as defined above.

The term "arylalkyl" or "aralkyl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "arylalkoxy" or "arylalkyloxy" as used herein, means an arylalkyl group, as defined herein, appended to the parent molecular moiety through an oxygen. The term "heteroarylalkoxy" as used herein, means an heteroarylalkyl group, as defined herein, appended to the parent molecular moiety through an oxygen.

The term "arylalkylthio" as used herein, means an arylalkyl group, as defined herein, appended to the parent molecular moiety through an sulfur. The term "heteroarylalkylthio" as used herein, means an heteroarylalkyl group, as defined herein, appended to the parent molecular moiety through an sulfur.

The term "arylalkenyl" as used herein, means an aryl group, as defined herein, appended to the parent molecular moiety through an alkenyl group. A representative example is phenylethylenyl.

The term "arylalkynyl" as used herein, means an aryl group, as defined herein, appended to the parent molecular moiety through an alkynyl group. A representative example is phenylethynyl.

The term "arylcarbonyl" as used herein, means an aryl group, as defined herein, appended to the parent molecular moiety through a carbonyl group, as defined herein. Representative examples of arylcarbonyl include, but are not limited to, benzoyl and naphthoyl.

The term "arylcarbonylalkyl" as used herein, means an arylcarbonyl group, as defined herein, bound to the parent molecule through an alkyl group, as defined herein.

The term "arylcarbonylalkoxy" as used herein, means an arylcarbonylalkyl group, as defined herein, bound to the parent molecule through an oxygen.

The term "aryloxy" as used herein, means an aryl group, as defined herein, appended to the parent molecular moiety through an oxygen. The term "heteroaryloxy" as used herein, means a heteroaryl group, as defined herein, appended to the parent molecular moiety through an oxygen.

The term "carbonyl" as used herein, means a —C(C=O)— group.

The term "carboxy" as used herein, means a —CO$_2$H group.

The term "cycloalkyl" as used herein, means monocyclic or multicyclic (e.g., bicyclic, tricyclic) hydrocarbons containing from 3 to 12 carbon atoms that is completely saturated or has one or more unsaturated bonds but does not amount to an aromatic group. Examples of a cycloalkyl group include cyclopropyl, cyclobutyl, cyclopentyl, cyclopentenyl, cyclohexyl and cyclohexenyl.

The term "cycloalkoxy" as used herein, means a cycloalkyl group, as defined herein, appended to the parent molecular moiety through an oxygen.

The term "cyano" as used herein, means a —CN group.

The term "formyl" as used herein, means a —C(C=O)H group.

The term "halo" or "halogen" means —Cl, —Br, —I or —F.

The term "haloalkoxy" as used herein, means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl" means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heterocyclyl", as used herein, include non-aromatic, ring systems, including, but not limited to, monocyclic, bicyclic and tricyclic rings, which can be completely saturated or which can contain one or more units of unsaturation, for the avoidance of doubt, the degree of unsaturation does not result in an aromatic ring system) and have 3 to 12 atoms including at least one heteroatom, such as nitrogen, oxygen, or sulfur. For purposes of exemplification, which should not be construed as limiting the scope of this invention, the following are examples of heterocyclic rings: azepines, azetidinyl, morpholinyl, oxopiperidinyl, oxopyrrolidinyl, piperazinyl, piperidinyl, pyrrolidinyl, quinicludinyl, thiomorpholinyl, tetrahydropyranyl and tetrahydrofuranyl. The heterocyclyl groups of the invention are substituted with 0, 1, 2, 3, 4 or 5 substituents independently selected from alkenyl, alkoxy, alkoxycarbonyl, alkoxysulfonyl, alkyl, alkylcarbonyl, alkylcarbonyloxy, alkylsulfonyl, alkylthio, alkynyl, amido, amino, carboxy, cyano, formyl, halo, haloalkoxy, haloalkyl, hydroxyl, hydroxyalkyl, mercapto, nitro, phosphinyl, silyl and silyloxy.

The term "heteroaryl" as used herein, include aromatic ring systems, including, but not limited to, monocyclic, bicyclic and tricyclic rings, and have 3 to 12 atoms including at least one heteroatom, such as nitrogen, oxygen, or sulfur. For purposes of exemplification, which should not be construed as limiting the scope of this invention: azaindolyl, benzo(b)thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl. The heteroaryl groups of the invention are substituted with 0, 1, 2, 3, 4 or 5 substituents independently selected from alkenyl, alkoxy, alkoxycarbonyl, alkoxysulfonyl, alkyl, alkylcarbonyl, alkylcarbonyloxy, alkylsulfonyl, alkylthio, alkynyl, amido, amino, carboxy, cyano, formyl, halo, haloalkoxy, haloalkyl, hydroxyl, hydroxyalkyl, mercapto, nitro, phosphinyl, silyl and silyloxy.

The term "heteroarylene," is art-recognized, and as used herein, pertains to a bidentate moiety obtained by removing two hydrogen atoms of a heteroaryl ring, as defined above.

The term "heteroarylalkyl" or "heteroaralkyl" as used herein, means a heteroaryl, as defined herein, appended to the parent molecular moiety through an alkyl group, as defined herein. Representative examples of heteroarylalkyl include, but are not limited to, pyridin-3-ylmethyl and 2-(thien-2-yl)ethyl.

The term "hydroxy" as used herein, means an —OH group.

The term "hydroxyalkyl" as used herein, means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "mercapto" as used herein, means a —SH group.

The term "nitro" as used herein, means a —$NO_2$ group.

The term "phosphinyl" as used herein includes derivatives of the $H_3P$— group, wherein the hydrogens are independently replaced with alkyl, adamantyl, fluoroalkyl, cycloalkyl, aryl, heteroaryl, heterocyclyl, aryloxy, or heteroaryloxy groups.

The term "silyl" as used herein includes hydrocarbyl derivatives of the silyl ($H_3Si$—) group (i.e., (hydrocarbyl)$_3Si$—), wherein a hydrocarbyl groups are univalent groups formed by removing a hydrogen atom from a hydrocarbon, e.g., ethyl, phenyl. The hydrocarbyl groups can be combinations of differing groups which can be varied in order to provide a number of silyl groups, such as trimethylsilyl (TMS), tert-butyldiphenylsilyl (TBDPS), tert-butyldimethylsilyl (TBS/TBDMS), triisopropylsilyl (TIPS), and [2-(trimethylsilyl)ethoxy]methyl (SEM).

The term "silyloxy" as used herein means a silyl group, as defined herein, is appended to the parent molecule through an oxygen atom.

The definition of each expression, e.g., alkyl, m, n, and the like, when it occurs more than once in any structure, is intended to be independent of its definition elsewhere in the same structure.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*.

Certain compounds contained in compositions of the invention may exist in particular geometric or stereoisomeric forms. In addition, polymers of the invention may also be optically active. The invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991). Protected forms of the inventive compounds are included within the scope of this invention.

A "polar solvent" means a solvent which has a dielectric constant (8) of 2.9 or greater, such as DMF, THF, ethylene glycol dimethyl ether (DME), DMSO, acetone, acetonitrile, methanol, ethanol, isopropanol, n-propanol, t-butanol or 2-methoxyethyl ether. Preferred polar solvents are DMF, DME, NMP, and acetonitrile.

An "aprotic solvent" means a non-nucleophilic solvent having a boiling point range above ambient temperature, preferably from about 25° C. to about 190° C., more preferably from about 80° C. to about 160° C., most preferably from about 80° C. to 150° C., at atmospheric pressure. Examples of such solvents are acetonitrile, toluene, DMF, diglyme, THF or DMSO.

A "polar, aprotic solvent" means a polar solvent as defined above which has no available hydrogens to exchange with the compounds of this invention during reaction, for example DMF, acetonitrile, diglyme, DMSO, or THF.

A "hydroxylic solvent" means a solvent that comprises a hydroxyl moiety; for example, water, methanol, ethanol, tert-butanol, and ethylene glycol are hydroxylic solvents.

For purposes of this invention, the chemical elements are identified in accordance with the Periodic Table of the Elements, CAS version, Handbook of Chemistry and Physics, 67th Ed., 1986-87, inside cover.

EXEMPLIFICATION

The invention now being generally described, it will be more readily understood by reference to the following examples, which are included merely for purposes of illustration of certain aspects and embodiments of the invention, and are not intended to limit the invention.

Example 1

Reaction Development

Figure 2:
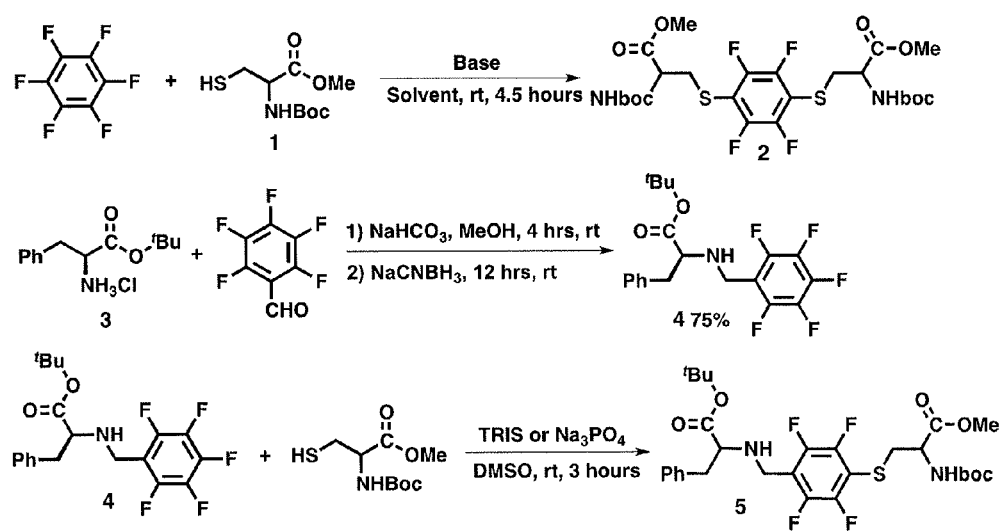
FIG. 2 depicts model "fluoroaryl-thiol-click" reactions on protected and functionalized amino acids.

We first focused on developing the conditions for coupling thiols and perfluorinated substrates using a model system featuring protected amino acid precursors. Reacting protected cysteine 1 with hexafluorobenzene in the presence of base in polar organic solvent for 4.5 hours leads to nearly quantitative formation of the disubstituted product 2 (FIG. 2), which was isolated via purification on silica gel and characterized via heteronuclear NMR spectroscopy. Disubstitution was observed to be favored in this process, even when hexafluorobenzene was used in excess to 1. This reactivity pattern is likely observed due to the activating ability of the thioether moiety positioned para to the C—F site of the aromatic ring. Significantly, progress of this reaction could be monitored by an in situ $^{19}$F NMR spectroscopy, where the starting material and product could be observed at two distinct resonances ($\delta$ −138 and −167 ppm, respectively). In another model experiment, we prepared a modified version of phenylalanine 4 (FIG. 2), which was designed as a prototype synthon for SPPS chemistry capable of introducing perfluorinated aryl functionality at the N-terminus of the peptide chain. Significantly, 4 could be cleanly coupled with 1 in 3 hours under conditions similar to the coupling of 1 with hexafluorobenzene (FIG. 2).

Example 2

Stapling of Model Systems—Thiolate Amino Acid Residues

Figure 3:
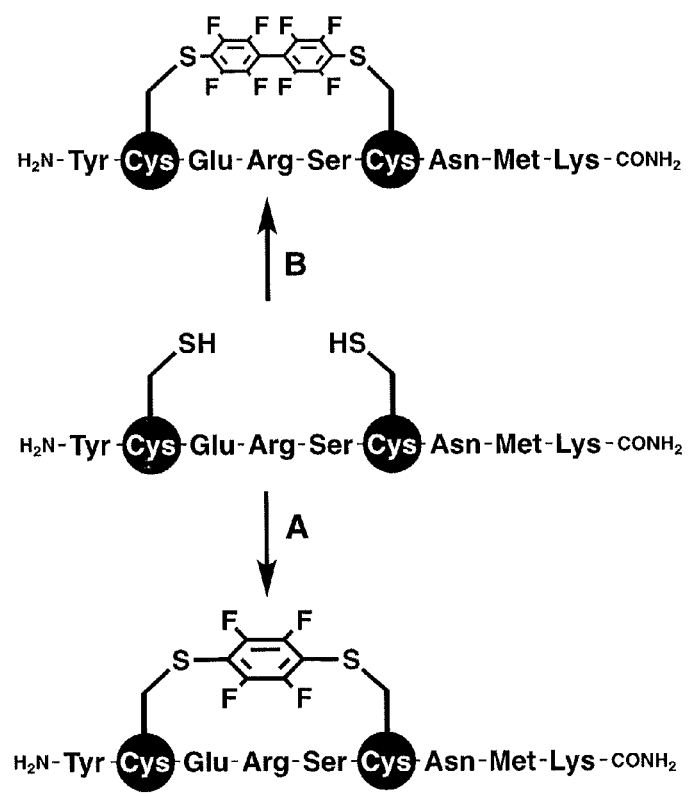
FIG. 3 depicts a stapling strategy via "fluoroaryl-thiol-click" chemistry between cysteine residues and perfluorinated aromatic units. Reaction A utilizes hexafluorobenzene as a stapling reagent, reaction B—decafluorobiphenyl. Figure discloses SEQ ID NOS 15, 34, and 10, respectively, in order of appearance.
Figure 4:
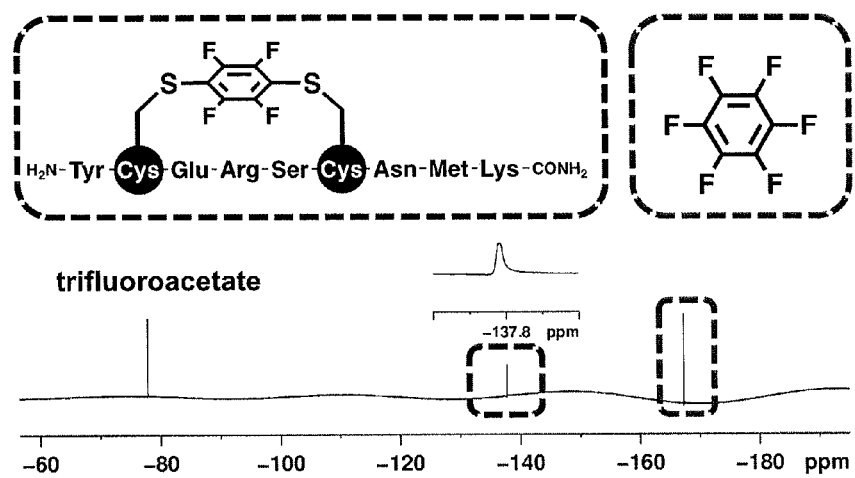
FIG. 4 depicts in situ $^{19}F$-NMR spectrum of the model peptide stapling reaction. Note: trifluoroacetate (TFA) appears in the spectrum since all peptides are isolated and used as TFA salts (SEQ ID NO: 10).

To test the developed protocols (vide supra) with unprotected peptides, we designed a series of random short peptide sequences containing cysteine residues separated by 3 amino acids (i, i+4). Previous studies by several research groups established chemical transformations allowing bridging of two amino acid residues positioned in an i, i+4 fashion. The resulting peptide structure is commonly referred to as a "stapled" peptide motif. Researchers have shown that these "stapled" peptides exhibit different physical and biological properties than their parent precursors. While there are several chemical transformations capable of producing "stapled" peptide motifs, olefin metathesis chemistry is considered to be a "gold standard" for this type of chemistry. Yet, the metathesis-based approach suffers from several limitations, including (1) the use of a metal-based catalyst, (2) the requirement for olefin functionalized non-natural amino-acid residues, and (3) frequent failure of the stapling protocol to operate on unprotected peptide species. In contrast, by using the "fluoroaryl-thiol-click" protocol, we were able to efficiently staple a variety of unprotected small peptides. For example, by simply incubating unprotected peptide sample in the presence of 50 mM solution of TRIS base in DMF for 2-6 hours (exact reaction times depend on the peptide sequence) with either hexafluorobenzene or decafluorobiphenyl substrates, nearly quantitative conversion of the starting material was observed (FIG. 3). Progress of the reaction and the identity of the products can be conveniently monitored by LC-MS and in situ $^{19}$F NMR spectroscopy (FIG. 4).

Example 3

Stapling of Model Systems—Perfluoroaryl Amino Acid Residues

Figure 5:
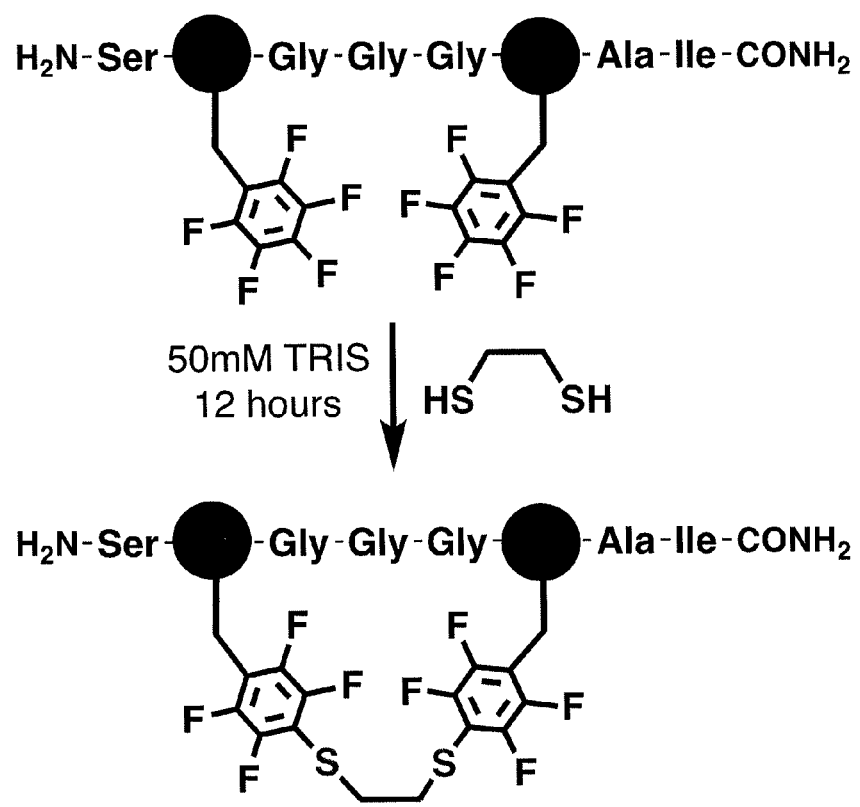
FIG. 5 depicts a stapling strategy for peptides containing perfluorinated amino acid residues. Figure discloses SEQ ID NOS 27 and 23, respectively, in order of appearance.

We also envisioned another potential approach to peptide stapling via developed "fluoroaryl-thiol-click" reaction, where perfluorinated functionalities are furnished within the peptide framework and positioned to react with bifunctional thiol linkers. To probe this scenario we synthesized a short, random sequence incorporating pentafluorophenylalanine residues at the i, i+4 positions (note: pentafluorophenylalanine amino acid precursors are commercially available for both "boc" and "fmoc" SPPS chemistries). Upon reacting this peptide with ethylenedithiol (EDT) for 12 hours under conditions similar to the ones used for stapling cysteine residues (vide supra), we observed nearly quantitative conversion of the starting material. LC-MS unequivocally confirmed the formation of a stapled product in this reaction (FIG. 5). Like in the case for cysteine modification, one can envision using dithiol linkers of various lengths, most of which are commercial entities. Furthermore, through this approach we envision the possibility of performing "fluoroaryl-thiol-click" stapling protocol on the resin before peptide deprotection, making the overall method extremely versatile.

Example 4

Stapling of One Peptide to Another Peptide

To probe whether the developed approach can be used for the coupling of two independent peptide fragments, we synthesized two random sequences, where one peptide chain was furnished with a perfluorinated moiety attached on the N-terminus and a second peptide chain was functionalized with a cysteamine moiety at the C-terminus. Synthesis of both peptides was accomplished via conventional SPPS "fmoc" chemistry, where for the perfluorinated aryl terminated species we utilized 13u deprotected version of amino acid 5 (vide supra). Upon mixing both peptides in 50 mM solution of TRIS in DMF with additional $Na_3PO_4$ base for 12 hours at room temperature, we observed ~60% conversion of the starting materials cleanly forming the desired coupled peptide product. While optimization studies for this type of reaction are currently underway, this experiment clearly demonstrates potential of utilizing "fluoroaryl-thiol-click" reaction for various peptides and potentially larger and more structurally complex biomolecules.

Example 5

Evaluation of Conformation of Stapled Peptides

Figure 6:
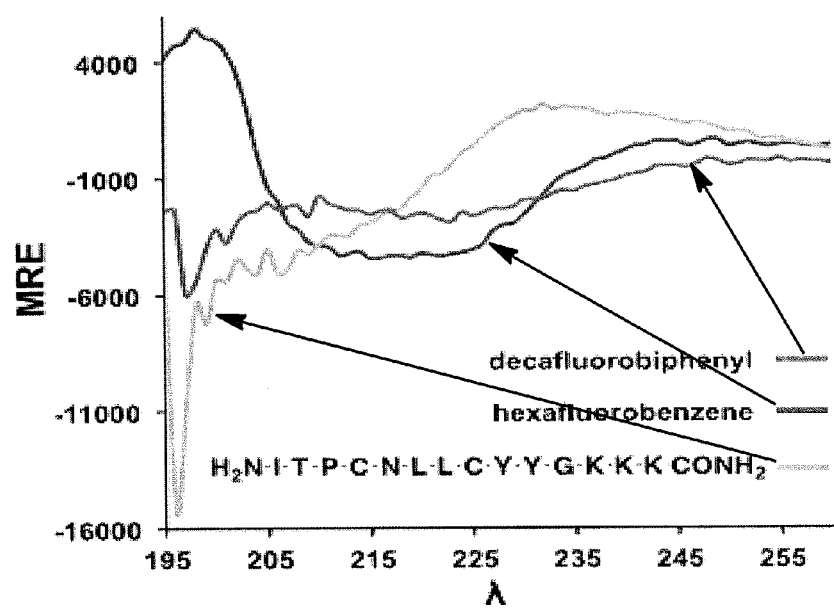
FIG. 6 depicts circular dichroism (CD) spectra indicating conformation changes occurring in the peptide due to "fluoroaryl-thiol-click" reaction (SEQ ID NO: 35).
Figure 7:
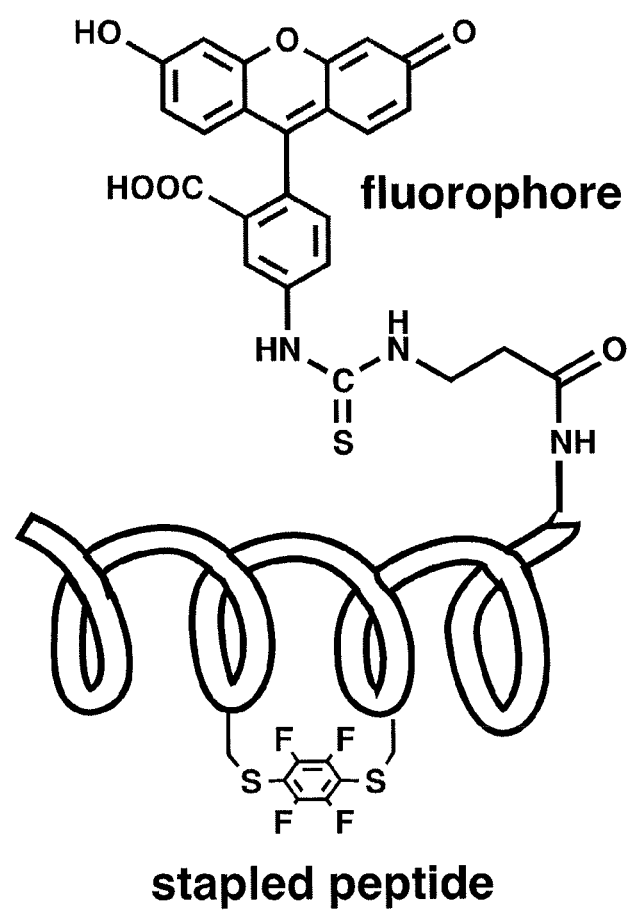
FIG. 7 depicts stapled peptide (ITPCNLLCYYGKKK) (SEQ ID NO: 1) labeled with a fluorescent tag (FITC) used to probe intracellular uptake.

We explored whether permanent alterations to the native peptide conformation could be achieved via "fluoroaryl-thiol-click" stapling. To address this hypothesis we synthesized a peptide structurally resembling the sequence of an HIV-1 Capsid Assembly Inhibitor (CAI). In particular, Cowburn et al. showed that stapling this peptide motif via olefin metathesis could efficiently stabilize its alpha-helix conformation, enabling more efficient intracellular uptake and increasing binding affinity towards the C-terminal domain of the HIV-1 capsid. Zhang, H., et al. *J. Mol. Bio.* 2008, 378, 565-580. Our model peptide featuring 14 residues was synthesized via "boc" SPPS chemistry on a 0.4-mmol scale, purified, and subsequently stapled with mono and biaryl motifs. Circular dichroism (CD) spectroscopy was further used to probe the effect of stapling on the conformational features of the peptide (FIG. 6). Specifically, we observed that while the native peptide species exhibits nearly a random-coil structure, stapling with hexafluorobenzene changes its CD spectra significantly and suggests that the helical structure was stabilized. A similar effect on a smaller magnitude is observed when the stapling is done with a decafluorobiphenyl linker. Studies aimed at the elucidation of the three-dimensional structure of these stapled peptides via 2D-NMR spectroscopy are underway. Furthermore, we are currently evaluating cell-penetrating properties of a FITC-labeled variant of this peptide via fluorescent confocal microscopy using a MT-2 cell line (FIG. 7). Importantly, stapling of the FITC-labeled peptide occurred smoothly and was not inhibited by the presence of a thiourea moiety (in contrast to the olefin metathesis approach). We are particularly interested in investigating whether stapled peptides will possess any enhanced cellular uptake properties due to the combination of helical stabilization and enhanced hydrophobicity provided by a perfluorinated moiety.

Example 6

Incorporation of Stapled Motif in Affibody

Figure 8:
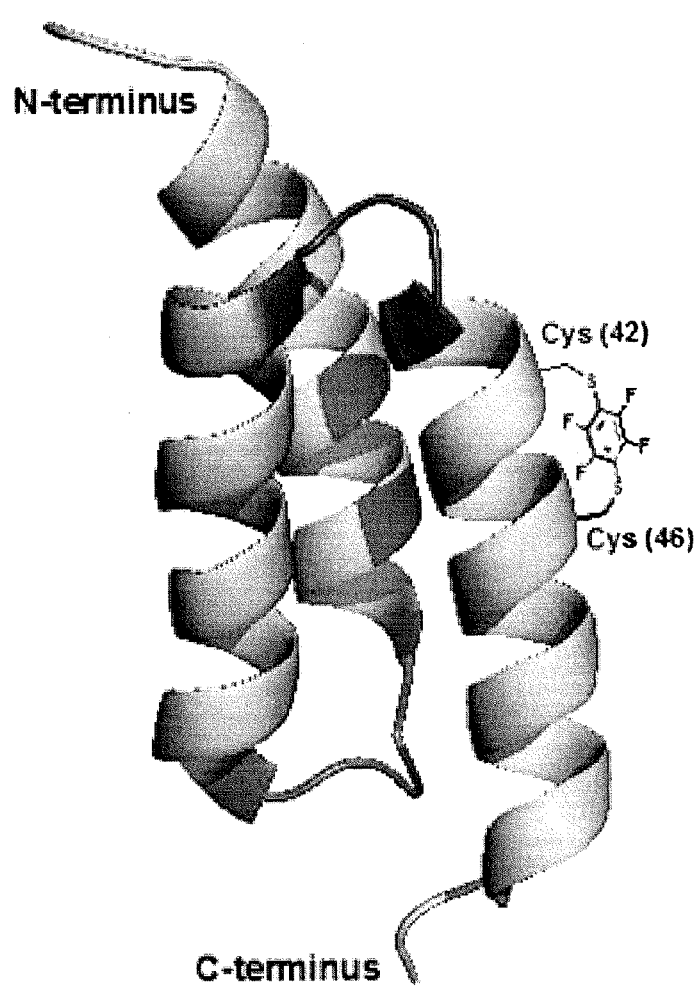
FIG. 8 depicts a model affibody protein featuring stapled motif accessed via "fluoro-thiol-click" chemistry.
Figure 9:
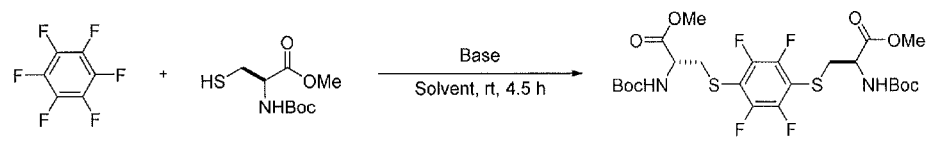
FIG. 9 depicts various experimental conditions for a model homocoupling reaction. The reactions were carried out on the bench-top, under ambient conditions, with ACS-grade solvents.
Figure 10:
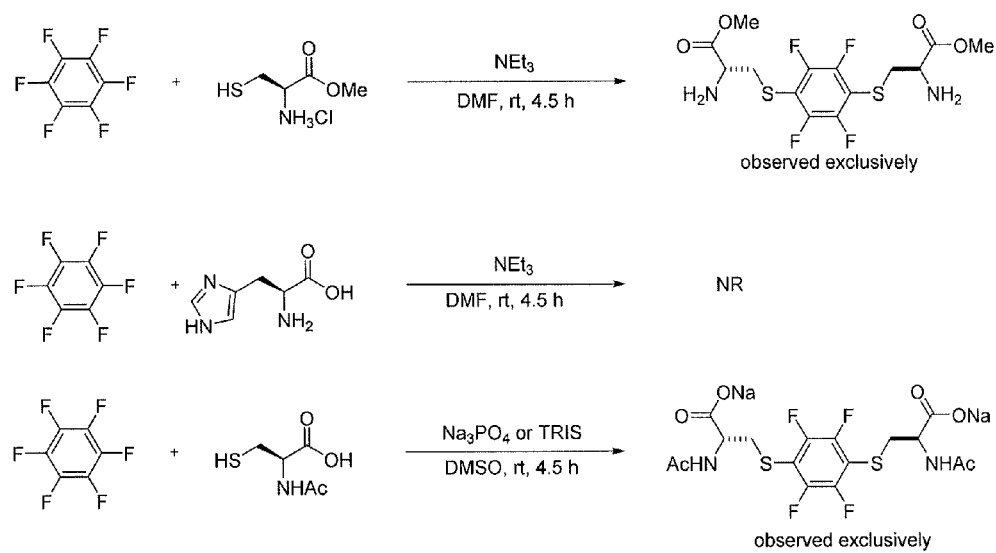
FIG. 10 depicts various reaction schemes showing the functional group tolerance and selectivity of the coupling reaction.

We are working to demonstrate the feasibility of incorporating a perfluoroaryl-stapled motif within the sequence of a small protein affibody (FIG. 8). This can be accomplished by synthesizing small peptide fragments, which are then coupled together via the native chemical ligation (NCL) protocol. Importantly, preliminary work indicates that the perfluoroaryl staple motif is chemically orthogonal to the conditions of NCL. This observation ultimately opens up a wide array of opportunities in accessing a series of synthetic proteins, properties of which can be rationally tuned via the described stapling approach. This may potentially render these systems towards higher protease degradation stability and enhanced cellular uptake features. We are currently exploring this research strategy in the context of the Human Epidermal Growth Factor Receptor 2 (HER-2) affibody (FIG. 8).

Example 7

Stapling Unprotected Peptides

1. General Considerations.

Hexafluorobenzene and decafluorobiphenyl were purchased from Oakwood Chemical and used as received. 2-(1H-Benzotriazol-1-yl)-1,1,3,3-tetramethyluronium hexafluorophosphate (HBTU) and α-Boc\Benzyl protected L-amino acids (Chem-Impex International, USA or Peptide International, USA). MBHA resin was obtained from Anaspec, USA. N,N-Dimethylformamide (DMF), dichloromethane (DCM), diethyl ether, and HPLC-grade acetonitrile were purchased from VWR International. Trifluoroacetic acid (TFA) was purchased from NuGenTec, USA or Halocarbon, USA. All other reagents were purchased from Sigma-Aldrich unless otherwise noted and used as received. HER-2 was bought from R&D Systems, Inc., Minneapolis, Minn. (catalog number: 1129-ER-050; lot number: FXR0711121) and reconstituted at 100 µg/mL concentration in PBS buffer.

All reactions with 1 were carried out under the atmosphere of dry argon gas. All reactions with peptides were conducted under ambient conditions. Peptides 4 and 5 were synthesized on a 0.4 mmol scale using Fmoc-Rink-MBHA resin using manual Fmoc/t-Butyl SPPS. Peptides 6, 7 and 8 were synthesized using MBHA resin support by manual in situ neutralization Boc/Benzyl SPPS. Each amino acid coupling was performed in the presence of HBTU reagent (coupling time— 12-15 min). In the case of Boc chemistry, final resins were washed with DCM, dried in air and simultaneously cleaved and side-chain deprotected by treatment with 10% (v/v) p-thiocresol and 10% (v/v) p-cresol in anhydrous HF for 1 hr at 0° C. Resulting crude peptide material was triturated with chilled diethyl ether, dissolved in 50:50 (MeCN:$H_2O$) mixture containing 0.1% TFA and subsequently lyophilized. Labeling of peptides with FITC was performed on the resin bound protected peptides by treating the protected peptide resin with the solution of fluorescein isothiocyanate (isomer I) (Sigma-Aldrich, 1.2 eq) dissolved in 2:1:1 mixture of pyridine/$CH_2Cl_2$/DMF, overnight. In all cases resulting crude peptide material was purified on preparative RP-HPLC (Agilent Zorbax SB $C_{18}$ column: 21.2×250 mm). HPLC fractions containing only product material (screened by MALDI) were combined and lyophilized. NMR spectra were acquired using Bruker Avance III spectrometer equipped with an autoswitchable probe and processed using TopSpin 3.1 software package. LC-MS spectra were acquired using Agilent 6520 ESI-QTOF mass-spectrometer equipped with $C_3$ and $C_{18}$ Zorbax columns. Spectra were processed using Agilent Mass Hunter software package. Deconvoluted mass spectra were obtained using maximum entropy setting.

2. Synthetic Procedures.

a. Representative Synthesis of 3a.

A mixture of hexafluorobenzene (280 mg, 1.5 mmol) and N-(tert-Butoxycarbonyl)-L-cysteine methyl ester (706 mg, 3 mmol) and $Na_3PO_4$ (600 mg, 3.7 mmol) was magnetically stirred in 15 mL of dry acetonitrile for 4.5 h at room temperature under an atmosphere of dry argon. The resulting mixture was filtered through a pad of Celite® on a glass-fritted filter, evaporated in vacuo and subsequently purified on a silica gel column (product elutes with 4:1 hexanes/EtOAc solvent mixture). Obtained fractions containing product were combined and dried in vacuo to afford the title compound 3a as an off-white solid (760 g, 82%). $^1$H NMR (400.1 MHz, $CDCl_3$): δ 5.47 (m, 2H), 4.48 (m, 2H), 3.68 (s, 3H), 3.61 (s, 3H), 3.41 (m, 1), 3.24 (m, 1), 2.88 (m, 2), 1.36 (s, 6), 1.31 (s, 6); $^{13}$C {$^1$H} NMR (100.6 MHz, $CDCl_3$, 24° C.): δ 170.8 (s), 170.3 (s), 155.1 (s), 154.7 (s), 147.9 (bm), 145.5 (bm), 114.1 (s), 80.1 (s), 80.0 (s), 54.9 (s), 53.7 (s), 52.6 (s), 36.3 (s), 28.2 (s), 28.0 (s), 27.1 (s); $^{19}$F {$^1$H} NMR (376.4 MHz, $CDCl_3$): δ −132.6 (bs, 4F). LC-MS: m/z calcd for [M+Na]$^+$: 639.1434. found: 639.1473.

B. Representative Synthesis of 3b.

This compound was synthesized and isolated in a procedure analogous to the one used for 3a. (850 mg, 74%). $^1$H NMR (400.1 MHz, $CDCl_3$): δ 5.45 (m, 2H), 4.61 (m, 2H), 3.68 (s, 6H), 3.5 (bm, 4H), 1.40 (s, 12H); $^{13}$C {$^1$H} NMR (100.6 MHz, $CDCl_3$, 24° C.): δ 170.3 (s), 154.8 (s), 148.2 (d), 145.8 (d), 145.1 (d), 142.6 (d), 116.5 (m), 106.9 (m), 80.4 (s), 53.6 (s), 52.6 (s), 52.6 (s), 36.4 (s), 28.1 (s); $^{19}$F {$^1$H} NMR (376.4 MHz, $CDCl_3$): δ −131.8 (bs, 4F), −137.6 (bs, 4F). LC-MS: m/z calcd for [M+$NH_4^+$]$^+$: 782.1816. found: 782.1797.

C. Representative Protocol for Peptide Stapling with 2a.

To a solid sample of peptide (7.5 µmoles) in a plastic Eppendorf tube was added 1.9 mL of 100 µM solution (~25 equiv.) of hexafluorobenzene in DMF and 1.5 mL of 50 mM solution of TRIS base in DMF. The tube was vigorously mixed on a shaker for 30 seconds and left at room temperature for 4.5 hours. Reaction mixture with peptides 4 and 5 were characterized by LC-MS. Resulting mixture from the reactions of peptides 6 and 7 was diluted with 6 mL of 0.1% TFA solution in water and subjected to purification on HPLC. Fractions containing stapled peptide product (analyzed by LC-MS) were combined and lyophilized. 6a and 7a were isolated in 73% and 69% yields, respectively.

D. Representative Protocol for Peptide Stapling with 2b.

To a solid sample of peptide (7.5 μmoles) in a plastic Eppendorf tube dissolved in 3 mL of DMF was added 0.15 mL of 100 μM solution (~2 equiv.) of decafluorobiphenyl 2b dissolved in DMF and 1.5 mL of 50 mM solution of TRIS base in DMF. The tube was vigorously mixed on a shaker for 30 seconds and left at room temperature for 4.5 hours. Reaction mixture with peptides 4 and 5 were characterized by LC-MS. Resulting mixture from the reactions of peptides 6 and 7 was diluted with 6 mL of 0.1% TFA solution in water and subjected to purification on HPLC. Fractions containing stapled peptide product (analyzed by LC-MS) were combined and lyophilized. 6b and 7b were isolated in 68% and 65% yields, respectively.

E. Syntheses of 8a and 8b.

8a and 8b were synthesized from 8 similarly to the procedure used to prepare 7a and 7b using 10 equiv. of perfluoroaryl reagent 2a and 2b respectively. All starting material was consumed within 4 hours of the reaction time. Resulting products were purified via HPLC and analyzed using LC-MS (vide supra).

F. Synthesis of the Stapled Affibody 10a.

Peptide $Thz^{41}$-$K^{58}$—$CONH_2$ (1.0 mM) was treated with hexafluorobenzene (20.0 mM) or decafluorobiphenyl (5.0 mM) in the solution of TRIS base in DMF (25.0 mM) for 4 hours at room temperature to provide corresponding stapled peptide (77.3% yield, calcd 2119.5 Da, obsd 2119.0±0.1 Da). The stapled [$Thz^{41}$-$Lys^{58}$] peptide was then treated with 0.2 M $MeONH_2$.HCl at pH 4.0 at room temperature for 5 hours to give stapled [$Cys^{41}$-$Lys^{58}$] peptide (Ma, 82% yield, calcd 2107.4 Da, obs 2107.0±0.1 Da) after RP-HPLC purification and lyophilization.

G. General Strategy for One-Pot Native Chemical Ligation of Peptides I, II, and IIIa:

[$Thz^{23}$-$Gly^{40}$]-thioester (3.2 μmol) and stapled [$Cys^{41}$-$Lys^{58}$] peptide (3.0 umol) were dissolved in a buffer (1.0 mL, pH 6.8) with guanidine.HCl (6 M), TCEP.HCl (20 mM), MPAA (40 mM) and sodium phosphate (0.2 M). The reaction mixture was incubated at room temperature for 7 hours. Without isolation, the crude reaction mixture was treated with $MeONH_2$.HCl at pH 4.0 at room temperature overnight to give stapled [$Cys^{23}$-$Gly^{40}$]-[$Cys^{41}$-$Lys^{58}$]. Then, [$Val^1$-$Leu^{22}$]-thioester (3.0 μmol) was added to the reaction mixture with the adjustment of pH 6.8 and incubated at room temperature for 5 hours to give stapled [$Val^1$-$Leu^{22}$]-[$Cys^{23}$-$Gly^{40}$]-[$Cys^{41}$-$Lys^{58}$] peptide (IVa, 34% yield, calcd 6861.4 Da, obsd 6862.3±0.1 Da) after purification by RP-HPLC.

H. Alkylation of Stapled [$Val^1$-$Leu^{22}$]-[$Cys^{23}$-$Gly^{40}$]-[$Cys^{41}$-$Lys^{58}$] Peptides:

Stapled [$Val^1$-$Leu^{22}$]-[$Cys^{23}$-$Gly^{40}$]-[$Cys^{41}$-$Lys^{58}$] peptides were alkylated at the two cysteine position with 2-bromoacetamide (50 mM) at room temperature in a buffer [pH 7.1, guanidine.HCl (6 M), TCEP.HCl (20 mM) and sodium phosphate (0.2 M)]. After 30 minutes, the reactions were quenched with MESNa (100 mM) to give stapled [$Val^1$-$Lys^{58}$] peptides (Va, 78.3% yield, calcd 6976.9 Da, obsd 6976.4±0.1 Da) after RP-HPLC purification and lyophilization.

I. Refolding of Stapled [$Val^1$-$Lys^{58}$] Peptide Va:

The stapled [$Val^1$-$Lys^{58}$] peptides were dissolved in a buffer (pH 7.5) with guanidine.HCl (6 M), TCEP.HCl (20 mM), Tris (20 mM) and NaCl (150 mM), and then sequentially diluted from guanidine.HCl (6 M) to guanidine.HCl (1 M). The peptide solutions were desalted into a buffer (pH 7.5) with Tris (20 mM) and NaCl (150 mM) using a HiTrap Desalting column (GE Healthcare, UK) and provided the stapled [$Val^1$-$Lys^{58}$] peptides (10a, 78% yield, calcd 6976.9 Da, obsd 6977.0±0.1 Da).

3. Cell Imaging.

293T HEK cells were cultured with DMEM with 10% FBS (v/v) in imaging dishes (70K cells/well) in 37° C., 5% $CO_2$ incubator for two days until they are about 70% confluent. Appropriate amounts of peptides 7, 7a, 7b, 8a and 8b dissolved in autoclaved $H_2O$ were added to the cells to final concentrations of 5 μM. Peptide 9 was first dissolved in DMSO to make a 200 μM stock and then added to cells to a final concentration of 5 μM. The cells were incubated with the samples for 4 hours at 37° C. and 5% $CO_2$. After incubation, cells were washed 3 times with DPBS and then fixed with 4% formaldehyde in DPBS for 10 minutes. They are then washed 3 times with HBSS and stained with 5 μg/mL wheat germ agglutinin-tetramethylrhodamine conjugate in HBSS for 20 minutes. The cells were subsequently washed with HBSS once and DPBS twice and stained with 5 μg/mL diamidino-2-phenylindole (DAPI) in DPBS for 30 minutes. They were washed 3 times with DPBS and covered in one drop of pri-Gold and cover slide. Images of peptide localization in cells were taken on PerkinElmer Ultraview Spinning Disk Confocal with 30% of its maximum laser power in 488 channel with 500 ms exposure time and 0.5 μm Z-stacking Image processing was done using Volocity software package (PerkinElmer).

4. Molecular Cloning, Protein Expression and Purification.

The plasmids encode Gag-derived proteins from the HIV-1 strain. The full-length gag expression vector was obtained from the Invitrogen. After PCR amplification and purification, the C-CA DNA fragment was obtained by digestion and then inserted into the pET21b vector with subsequently overnight ligation. The C-CA protein were expressed and purified.

5. Circular Dichroism Spectroscopy (CD).

CD measurements were done with Aviv 202 spectrometer using 1 mm quartz cuvette. Peptide solutions were made by dissolving solid samples in 25% acetonitrile/water mixture, CD spectra of 3a and 3b were measured in acetonitrile, CD spectra of affibodies was collected in 10 mM phosphate buffer. Concentration of affibodies was estimated by UV absorbance measurements at 280 nm. Contribution of the perfluorinated staple in 6a on the absorbance value at 280 nm was taken into account (estimated molar extinction coefficient for [—S—$C_6F_4$—S-]~5000 $cm^{-1}M^{-1}$ from UV measurements of solutions of 6 and 6a) in these measurements. Data processing included solvent background correction (subtraction) and adjustment for pathlength and concentration (MRE=[θ]λ=$θ_{obs}$×1/(10 lcn); $θ_{obs}$=measured ellipticity, θ=mean residual ellipticity in deg×$cm^2$×$dmol^{-1}$, 1=pathlength (cm); c=concentration of peptide (M); n=# of amino acids). α-helicities of the peptides were estimated using previously established methods.

6. Proteolysis Assays.

100 μL of peptide (100 μM) in phosphate buffer (pH 8.1) was mixed and incubated with 40 μL of the protease solution (trypsin—70 μg/mL; chymotrypsin—50 μg/mL) at 37° C. Aliquots of 35 μL were quenched with 55 μL of 1% TFA solution in MeCN and subjected to LC-MS analysis at 10, 25 and 40 minutes respectively. Peptide concentrations at different time points were quantified by integration of the TIC trace relative to the starting peptide sample. Results of these experiments are summarized in the Figure below. Note, that in the case of experiments with unstapled peptide 7, <1% of the intact peptide was observed after 10 minutes.

For experiments with proteinase K, 100 µL of peptide (100 µM) in phosphate buffer was incubated with the 40 µL of protease solution (100 µg/mL) for 3 hours at 37° C. 35 µL aliquot of the cleaved peptide solution was diluted with 55 µL of 1% TFA solution in MeCN and subjected to LC-MS analysis.

7. Flow Cytometry.

293T HEK cells were cultured with DMEM with 10% FBS (v/v) in 24-well plates (70K cells/well) in 37° C., 5% $CO_2$ incubator for two days until ~70% confluent. Solid peptide samples were dissolved in autoclaved $H_2O$ (except for NYAD-2, which was dissolved in DMSO) were added to the cells to final concentrations of 5 µM or 25 µM. The cells were incubated with the samples for 4 hours at 37° C. and 5% $CO_2$. After incubation, cells were lifted by pipetting then transferred to V-bottom 96-well plates and spun at 1000 rpm for 3 min to pellet. The pellets were washed 4 times with DPBS then re-suspended in PBS with 2% FBS (v/v), 0.1% BSA (w/v) and 1% pen-strep (v/v) for FACS analysis on BD LSR II HTS instrument.

8. Biacore Mesurements.

Biacore 2000 and 3000 instruments (GE) were used for on-surface real-time biospecific interaction analysis between HER-2 with affibodies, and C-CA with peptides. HER-2 (~3000 RU) and C-CA (~2500 RU) were immobilized onto a CM5 sensor chip according to the normal procedures.[4] A second flow-cell surface was activated and deactivated with ethanolamine and used as a reference surface. Binding analyses were done at 25° C., and commercial HBS buffer (GE) was used as the running buffer for all of the measurements (300 sec—adsorption, 300 sec—desorption, 10 µL/min flow rate). Surface regeneration between each binding experiment was done with 10 mM glycine solution (pH 2, 5 minutes, 10 µL/min flow rate).

9. Molecular Dynamics Simulations

Molecular dynamics simulations were performed for the wild-type 6 and the two stapled peptides 6a,b to characterize the effects of the staples on peptide structure. All simulations were performed using Gromacs 4.5.5 in conjunction with the OPLS-AA force field and TIP4P water model.

Simulations were run in the isobaric-isothermal (NPT) ensemble at a temperature of 300 K and a pressure of 1 bar. The temperature was maintained using the v-rescale thermostat with a coupling time constant $\tau_T$=0.1 ps. To avoid the "hot solvent-cold solute" problem, the peptide and solvent were coupled to separate thermostats. The pressure was controlled using an isotropic Parrinello-Rahman barostat with a coupling time of $\tau_P$=2.0 ps and a compressibility of $4.5 \times 10^{-5}$ $bar^{-1}$. All bonds were constrained with the LINCS algorithm. A 2 fs time step with the leap-frog algorithm was used to evolve the dynamics. The non-bonded interactions (Lennard-Jones and electrostatic) were truncated at 1.0 nm without shift or switch functions. Long-range electrostatic interactions beyond the cut-off distance were calculated by the Particle Mesh Ewald summation method with a Fourier spacing of 0.12 nm and an interpolation order of 4. A long-range analytic dispersion correction was applied to both the energy and pressure to account for the truncation of Lennard-Jones interactions.

The initial structure of the wild type peptide was prepared with the Molefacture plugin in VMD. The stapled peptides were constructed using the Builder module of PyMol. The simulation system was set up as follows. The starting structure was solvated in a cubic periodic box of water after an energy minimization in vacuum. The dimension of the water box was chosen such that the minimum distance between any atom of the fully extended wild type peptide and the box walls is 1.0 nm. $Na^+$ and $Cl^-$ ions were added to obtain a neutral system with physiological ion concentration of 150 mM. The resulting system was further optimized by steepest descent algorithm to remove bad contacts. A 50 ps NVT (isochoric-isothermal) and a 50 ps NPT simulations with the peptide heavy atoms restrained by a harmonic potential with a force constant of 1000 $kJ \cdot mol^{-1} \cdot nm^{-2}$ were implemented sequentially to equilibrate the solvent molecules and adjust the density.

All the three peptides were started from the α-helix conformation. Each peptide was subjected to ten independent runs with different initial velocities assigned from the Maxwell-Boltzmann distribution at 300 K. Before data collection, an additional 100 ps NVT simulation followed by a 100 ps NPT simulation was also performed to equilibrate the whole system. During production, the trajectory was recorded every 10 ps. All production runs were 500 ns in length. The ten independent runs bring a total of 5 µs trajectory and 500,000 snapshots for analysis for each peptide.

Example 8

Convergent Diversity-Oriented Side-Chain Macrocyclization of Unprotected Polypeptides 1. Materials, Methods and General Considerations α-Fmoc protected L-amino acids, 2-(1H-Benzotriazol-1-yl)-1,1,3,3-tetramethyluronium hexafluorophosphate (HBTU), and Rink amide linker were purchased from ChemImpex International (Wood Dale, Ill.). MBHA resin was obtained from Anaspec (Fremont, Calif.). Hexafluorobenzene and decafluorobiphenyl were purchased from Oakwood Chemicals (West Columbia, S.C.). Decafluorobiphenyl sulfide was purchased from SynQuest Laboratories (Alachua, Fla.). N,N-dimethylformamide (DMF), dichloromethane (DCM), diethyl ether, and HPLC-grade acetonitrile were purchased from VWR International (Philadelphia, Pa.). All other reagents were purchased from Sigma-Aldrich and used as received, unless otherwise noted.

LCMS chromatograms and associated mass spectra were acquired using Agilent 6520 ESI-QTOF mass spectrometer equipped with Zorbax SB $C_3$ column: 2.1×150 mm, 5 µm, gradient: 0-2 minutes 5% B, 2-11 minutes 5-65% B, 11-12 minutes 65% B, flow rate: 0.8 mL/min. Data was processed using Agilent Mass Hunter software package. Deconvoluted mass spectra were obtained using maximum entropy setting. All conversions associated with peptides shown in this work were determined by measuring UV absorption at λ=214 nm using LC-MS. First, using Agilent Mass Hunter software package, the peak areas for all relevant chromatographic peaks were integrated. For all reactions, the relevant peaks from UV absorption spectra at λ=214 nm came from unconverted substrate, desired peptide product, disulfide crosslinked byproducts, and other peptide byproducts. Conversion was calculated using equation: % yield=$S_{pro}/S_{all}$ where $S_{pro}$ is the peak area of desired macrocyclized peptide and $S_{all}$ is the sum of all the peak areas including the product peak and byproduct peaks.

NMR spectroscopy was conducted on a 400 MHz Bruker Avance III system and processed with TopSpin 3.1 software supplied by Bruker. Variable temperature NMR spectra were plotted using MestReNova suite, version 7.1. $^1H$ NMR spectra were referenced to residual solvent resonances in deuterated solvents. $^{19}F$ NMR spectra were referenced to $CFCl_3$ external standard at δ 0.0. The following abbreviations are used in the description of the acquired NMR spectra: s—singlet, d—doublet, m—multiplet.

The initial structures of the compounds for DFT calculations were generated and energy minimized with the molecular modeling software Avogadro. After a full geometry optimization at the B3LYP/6-311G(d,p) level with the Gaussian 09 Rev. D.01 package, the Mulliken charges were calculated.

2. Solid-Phase Supported Peptide Synthesis and Purifications

Peptides 1'-14' were synthesized on a 0.2 mmol scale on MBHA resin using manual Fmoc-SPPS chemistry' and home-built flow-based system. Specifically, all reagents and solvents are delivered to a stainless steel reactor containing resin at a constant flow rate using HPLC pump; temperature of the reactor was maintained at 60° C. during the synthesis using water bath. Procedure for amino-acid residue coupling cycle contained 30 second coupling with 1 mmol Fmoc protected amino acids, 1.0 mmol HBTU, and 500 uL of diisopropyl ethyl amine (DIEA) in 2.5 mL of DMF, flow rate was 6 mL/min; 1 minute wash with DMF, flow rate was 20 mL/min; 20 seconds deprotection with 50% (v/v) piperidine in DMF, flow rate was 20 mL/min; and 1 minute wash with DMF, flow rate was 20 mL/min. The C-terminal amide was introduced using Fmoc-Rink amide linker. Side-chain protections for L-amino acids were as followed: Arg(Pbf), Cys(Trt), Glu(tBu), Ser(tBu), Lys(Boc), Tyr(tBu), and Thr(tBu). The resin was washed thoroughly with DCM and air dried after completion of the stepwise SPPS. The peptide is then simultaneously cleaved from the resin and side-chain deprotected by treatment with 2.5% (v/v) water, 2.5% (v/v) 1,2-ethanedithiol (EDT), and 1% (v/v) triisoproprylsilane in neat trifluoroacetic acid (TFA) for 2 hours at room temperature. Resulting solution containing peptide was evaporated by blowing a stream of nitrogen gas over its surface for 20-30 minutes, then triturated and washed with cold diethyl ether. Obtained gummy-like solid was dissolved in 50% $H_2O$: 50% acetonitrile containing 0.1% TFA and lyophilized. The same solvent compositions were used in most of the experiments in this Example and will be referred to as A: 0.1% TFA in $H_2O$; and B: 0.1% TFA in acetonitrile.

The crude peptide was dissolved in 95% A: 5% B with 6 M guanidinium hydrochloride and purified by preparative RP-HPLC (Agilent Zorbax SB $C_{18}$ column: 10×250 mm, 7 μm, linear gradient: 5-50% B over 90 min, flow rate: 5 mL/min). HPLC fractions were spotted with MALDI using alpha-cyano-4-hydroxycinnamic acid (CHCA) matrix in 50% A: 50% B and checked for fractions with desired molecular mass. The purity of fractions was confirmed by analytical RP-HPLC (Agilent Zorbax SB $C_3$ column: 2.1×150 mm, 5 μm, gradient: 0-2 minutes 5% B, 2-11 minutes 5-65% B, 11-12 minutes 65% B, flow rate: 0.8 mL/min). HPLC fractions containing only product material (screened by MALDI) were combined and lyophilized.

3. Synthesis of Linkers $L_d$:

To a magnetically stirred solution of ethanedithiol (0.27 g, 3 mmols) in 30 mL of anhydrous acetonitrile in a Schlenk flask cooled on ice-bath under positive flow of argon gas was added sodium phosphate (0.98 g, 6 mmol), followed by neat hexafluorobenzene (22 g, 75 mmol). Resulting suspension was warmed to room temperature and left stirring for 5 hours under inert atmosphere. Product mixture was then filtered through a pad of Celite™ on a fitted glass filter, evaporated in vacuo and subjected to purification on a silica gel column (2:1 hexanes/dichloromethane). Fractions containing product were combined and dried in vacuo affording $L_d$ as white solid (0.23 g, 18% yield). $^1$H NMR (400.1 MHz, CDCl$_3$, 298 K): δ 3.01 (s, 4H, Alkyl-CH$_2$); $^{19}$F NMR (376.5 MHz, CDCl$_3$, 298 K): δ −132.1 (m, 4F), −151.4 (m, 2F), −160.3 (m, 4F).

$L_g$ was prepared according to the procedure analogous to the one used for the synthesis of $L_d$ (vide supra) on a 3 mmol scale from 1,4-benzenedimethanethiol (Sigma-Aldrich, CAS Number: 105-09-9) affording $L_g$ as a white solid (0.31 g, 20% yield). $^1$H NMR (400.1 MHz, CDCl$_3$, 298 K): δ 7.10 (s, 4H, Ar—H), 4 (s, 4H, Benzyl-CH$_2$); $^{19}$F NMR (376.5 MHz, CDCl$_3$, 298 K): δ −132.4 (m, 4F), −152.1 (m, 2F), −161.1 (m, 4F).

$L_f$:

CuSC$_6$F$_5$ (1.5 g, 5.8 mmol)[4] and 1,4-diiodobenzene (0.66 g, 2 mmol) were combined in a 15 mL oven-dried test-tube equipped with a small magnetic stir bar. Reaction vessel was sealed with Teflon screw-cap septum, evacuated under vacuum and back-filled with argon gas. Anhydrous dimethylformamide (5 mL) was added to the reaction vessel and the resulting mixture was allowed to stir at 140° C. for 2.5 hours. Product mixture was cooled to room temperature, quenched with 10% solution of aqueous hydrochloric acid and extracted with diethyl ether (2 times, 30 mL total). Organic fractions were combined, dried in vacuo and subjected to column chromatography purification on silica gel eluted with 5% dichloromethane in hexanes solvent mixture. Collected product fractions were combined, dried in vacuo and recrystallized from hexanes at −20° C. yielding white solid product (0.58 g, 61% yield). $^1$H NMR (400.1 MHz, CDCl$_3$, 298 K): δ 7.27 (s, 4H, Aryl-H); $^{19}$F NMR (376.5 MHz, CDCl$_3$, 298 K): δ −131.4 (m, 4F), −150.4 (m, 2F), −159.9 (m, 4F).

$L_e$ was prepared according to the procedure analogous to the one used for the synthesis of $L_f$ (vide supra) on a 2 mmol scale from 1,4-dibromo-2,3,5,6-tetrafluorobenzene (Sigma Aldrich, CAS Number: 344-03-6) affording $L_e$ as an off-white solid (0.66 g, 60% yield). $^{19}$F NMR (376.5 MHz, C$_6$D$_6$, 298 K): δ −132.8 (d, 4F, J$_{F-F}$=22 Hz), −132.9 (s, 4F), −150.6 (m, 2F), −161.2 (m, 4F).

4. Syntheses of Peptides 7a", 7b" and 14a":

To a solid sample of peptide 7' (5 μmoles) in a plastic Eppendorf tube dissolved in 20 mM Tris base in 1 mL of DMF was added 500 μmoles of hexafluorobenzene or decafluorobiphenyl for peptide 7a" or peptide 7b" respectively. The tube was vortexed for 1 minute and left at room temperature for 1 hour. The reaction mixture was characterized by LCMS analysis till complete. Resulting reaction mixture was quenched by addition of 20 mL of 95% A: 5% B. Peptide 7a" and 7b" were purified by RP-HPLC. Fractions were characterized by LCMS analysis. Pure fractions containing product were collected and lyophilized.

To a solid sample of peptide 14' (5 μmoles) in a plastic Eppendorf tube dissolved in 20 mM Tris base in 1 mL of DMF was added 500 μmoles of hexafluorobenzene for peptide 14a". The tube was vortexed for 1 minute and left at room temperature for 1 hour. The reaction mixture was characterized by LCMS analysis till complete. Resulting reaction mixture was quenched by addition of 20 mL of 95% A: 5% B. Peptide 14a" were purified by RP-HPLC. Fractions were characterized by LCMS analysis. Pure fractions containing product were collected and lyophilized.

5. General Protocols for Peptide Macrocyclization Scan Reactions with Linker $L_a$.

To a solution of peptide (10 mM, 5 μL) in a plastic Eppendorf tube was added hexafluorobenzene (20 mM in DMF, 20 μL) and TRIS base (50 mM in DMF, 20 μL). The reaction was mixed by pipetting the solution up and down 20 times and left at room temperature for 2 hours. Reaction progress was monitored via LC-MS by diluting 1 μL aliquots with 20 μL of 50% A: 50% B.

Reactions with Linker $L_b$-$L_g$.

To a stock solution of peptide dissolved in DMF (10 mM, 8 µL) in a plastic Eppendorf tube was added liners $L_b$-$L_g$ (20 mM in DMF, 5 µL) and TRIS base (50 mM in DMF, 16 µL) and additional 11 µL of DMF. The reaction was mixed by pipetting the solution up and down 20 times and left at room temperature for 2 hours. Reaction progress was monitored via LC-MS by diluting 1 µL aliquots with 20 µL of 50% A: 50% B.

Reactions with Linker $L_b$ and $L_c$ at Diluted Concentrations.

To a stock solution of peptide dissolved in DMF (10 mM, 1 µL) in a plastic Eppendorf tube was added linkers $L_b$ or $L_c$ (20 mM in DMF, 0.5 µL) and TRIS base (50 mM in DMF, 20 µL) and additional 78.5 µL of DMF. The reaction was mixed by pipetting the solution up and down 20 times and left at room temperature for 2 hours. Reaction progress was monitored via LC-MS by diluting 10 µL aliquots with 100 µL of 50% A: 50% B.

Reactions with Dithiol Linkers.

To a stock solution of bis-perfluoroarylated peptide dissolved in DMF (10 mM, 2 µL) in a plastic Eppendorf tube was added 1,4-benzenedimethanethiol (40 mM in DMF, 1 µL) or 1,4-butanedithiol (40 mM in DMF, 1 µL) and TRIS base (50 mM in DMF, 8 µL) and additional 9 µL of DMF. The reaction was mixed by pipetting the solution up and down 20 times and left at room temperature for 2 hours. Reaction progress was monitored via LC-MS by diluting 1 µL aliquots with 20 µL of 50% A: 50% B.

Example 9

Inhibition of P53/MDM2 Interaction in Glyoblastoma Cells by Stapled Peptides

Figure 45:
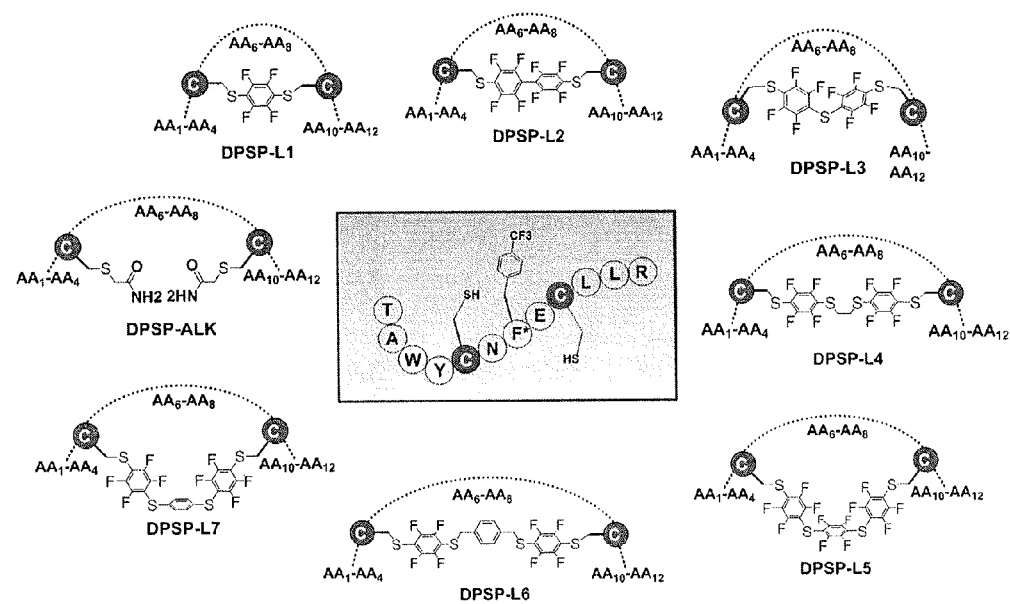
FIG. 45 depicts the structures of various stapled D-p53 peptides (SEQ ID NO: 111).

The stapled peptides shown in FIG. 45 were synthesized.

Human glioblastoma cancer cell lines U87 were cultured in EMEM supplemented with 10% FBS, 100 U/mL penicillin, and 100 µg/mL streptomycin at 37° C. with 5% $CO_2$ under fully humidified conditions. Cells were seeded at 5,000 cells/well in 96-well plates and allowed to grow for 24 h before treatment with peptides in various concentrations. Spectroscopic readings were taken 3 days after treatment at 490 nm, and percent cell viability was calculated on the basis of optical density values of sample wells.

Figure 46:
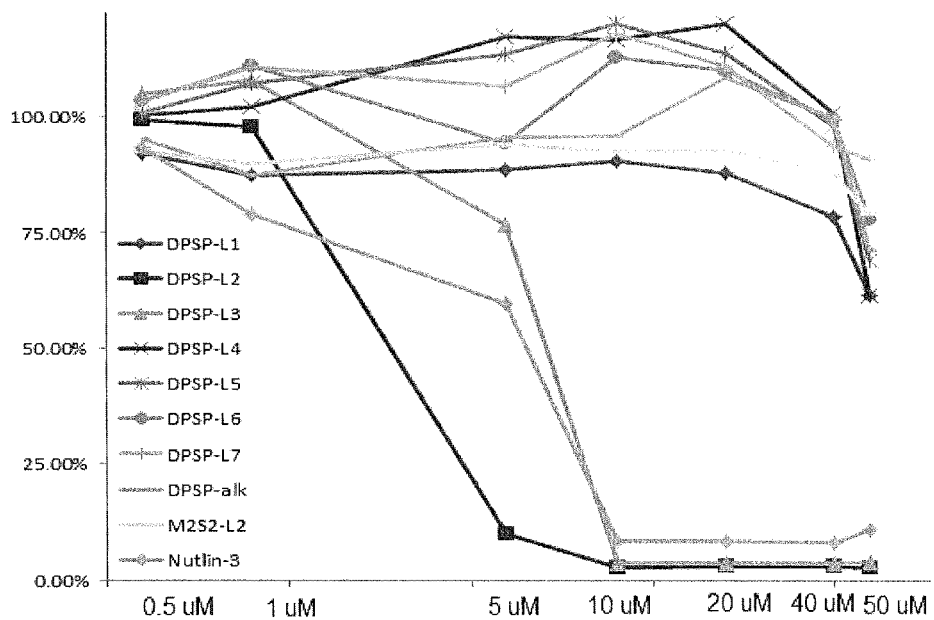
FIG. 46 depicts the results of a MTS assay for stapled D-p53 peptides of the invention, as described in Example 9.

Assay results are depicted in FIG. 46.

Example 10

Selective Cysteine Modification in Polypeptides Enabled by Promiscuous Glutathione S-Transferase Materials Hexafluorobenzene and decafluorobiphenyl were purchased from Oakwood Chemicals (West Columbia, S.C.). Decafluorobiphenyl sulfide was purchased from SynQuest Laboratories (Alachua, Fla.). Glutathione (GSH) was obtained from Calbiochem. Tris(2-carboxyethyl)phosphine hydrochloride (TCEP.HCl) was purchased from Hampton Research (Aliso Viejo, Calif.). 2-(1H-Benzotriazol-1-yl)-1,1,3,3-tetramethyluronium hexafluorophosphate (HBTU), Rink amide linker, biotin, and α-Fmoc protected L-amino acids were purchased from Chem-Impex International (Wood Dale, Ill.). Fluorescein-5-maleimide was purchased from Invitrogen (Grand Island, N.Y.). 4-methylbenzhydrylamine (MBHA) resin was obtained from Anaspec (Fermont, Calif.). N,N-Dimethylformamide (DMF), dichloromethane (DCM), diethyl ether, HPLC-grade acetonitrile, and guanidine hydrochloride were obtained from VWR International (Philadelphia, Pa.). QuickChange Lightening Site-Directed Mutagenesis kit was purchased from Agilent Technologies (La Jolla, Calif.). Complete protease inhibitor tablets were purchased from Roche Diagnostics, Germany. All other reagents were purchased from Sigma-Aldrich and used as received unless otherwise noted.

Glutathione S-Transferase (GST)

GSTs used in this work were purchased from Sigma Aldrich. GST from equine liver (Sigma Aldrich catalog number: G6511) and GST from human placenta (Sigma Aldrich catalog number: G8642) were received as lyophilized powders containing Tris and phosphate buffer salts, reduced glutathione, and EDTA. Water was added to dissolve these GST samples to a final concentration of 10 mg/mL. GST from *Schistosoma Japonicum* (Sigma Aldrich catalog number: G5663) was received as a solution of phosphate buffered saline, pH 7.4, containing 0.02% sodium azide, concentration was ≥3 mg/mL and purity was ≥85% (SDS-PAGE). All GSTs were dialyzed against 20 mM Tris, 150 mM NaCl, pH 7.5 buffer to remove reduced glutathione, and aliquots of GSTs were stored at −80° C. All reactions were performed with GST from equine liver unless otherwise noted.

Solid Phase Peptide Synthesis

All peptides were synthesized at a 0.2 mmol scale on MBHA resin using manual Fmoc-SPPS chemistry using home-built flow-based system. Specifically, all reagents and solvents are delivered to a stainless steel reactor containing resin at a constant flow rate using HPLC pump; temperature of the reactor was maintained at 60° C. during the synthesis using water bath. Procedure for amino-acid residue coupling cycle contained 30 second coupling with 1 mmol Fmoc protected amino acids, 1.2 mmol HBTU, and 500 µL of diisopropyl ethyl amine (DIEA) in 2.5 mL of DMF, flow rate was 6 mL/min; 1 minute wash with DMF, flow rate was 20 mL/min; 20 seconds deprotection with 50% (v/v) piperidine in DMF, flow rate was 20 mL/min; and 1 minute wash with DMF, flow rate was 20 mL/min. The C-terminal amide was introduced using Rink amide linker. Side-chain protections for L-amino acids were as followed: Arg(Pbf), Cys(Trt), Cys(S-tBu), γ-Glu(tBu), Glu(tBu), Ser(tBu) Lys(Boc), Tyr(tBu), and Thr(tBu). The resin was washed thoroughly with DCM and air dried after completion of the stepwise SPPS. The peptide is then simultaneously cleaved from the resin and side-chain deprotected by treatment with 2.5% (v/v) water, 2.5% (v/v) 1,2-ethanedithiol (EDT), and 1% (v/v) triisoproprylsilane in neat trifluoroacetic acid (TFA) for 2 hours at room temperature. Resulting solution containing peptide was evaporated by blowing a stream of nitrogen gas over its surface for 20-30 minutes, then triturated and washed with cold diethyl ether. Obtained gummy-like solid was dissolved in 50% $H_2O$: 50% acetonitrile containing 0.1% TFA and lyophilized. The same solvent compositions were used in most of the experiments in this Example and will be referred to as A: 0.1% TFA in $H_2O$; and B: 0.1% TFA in acetonitrile.

Peptide Purification

The crude peptide was dissolved in 95% A: 5% B with 6 M guanidinium hydrochloride and purified by preparative RP-HPLC (Agilent Zorbax SB $C_{18}$ column: 21.2×250 mm, 7 µm, linear gradient: 5-50% B over 90 min, flow rate: 5 mL/min). HPLC fractions were spotted with MALDI using alpha-cyano-4-hydroxycinnamic acid (CHCA) matrix in 50% A: 50% B and checked for fractions with desired molecular mass. The purity of fractions was confirmed by analytical RP-HPLC (Agilent Zorbax SB $C_3$ column: 4.6×250 mm, 5 µm, gradient: 0-2 minutes 5% B, 2-11 minutes 5-65% B, 11-12 minutes 65% B, flow rate: 0.8 mL/min). HPLC fractions containing only product material (screened by MALDI) were combined and lyophilized. Peptides synthesized using SPPS and purified by HPLC are listed in FIG. 47.

LCMS Analysis

LCMS chromatograms and associated mass spectra were acquired using Agilent 6520 ESI-QTOF mass spectrometer equipped with Zorbax SB $C_3$ column: 4.6×250 mm, 5 µm, gradient: 0-2 minutes 5% B, 2-11 minutes 5-65% B, 11-12 minutes 65% B, flow rate: 0.8 mL/min. Data was processed using Agilent Mass Hunter software package. Deconvoluted mass spectra were obtained using maximum entropy setting.

Determination of Reaction Yields

Figure 59:
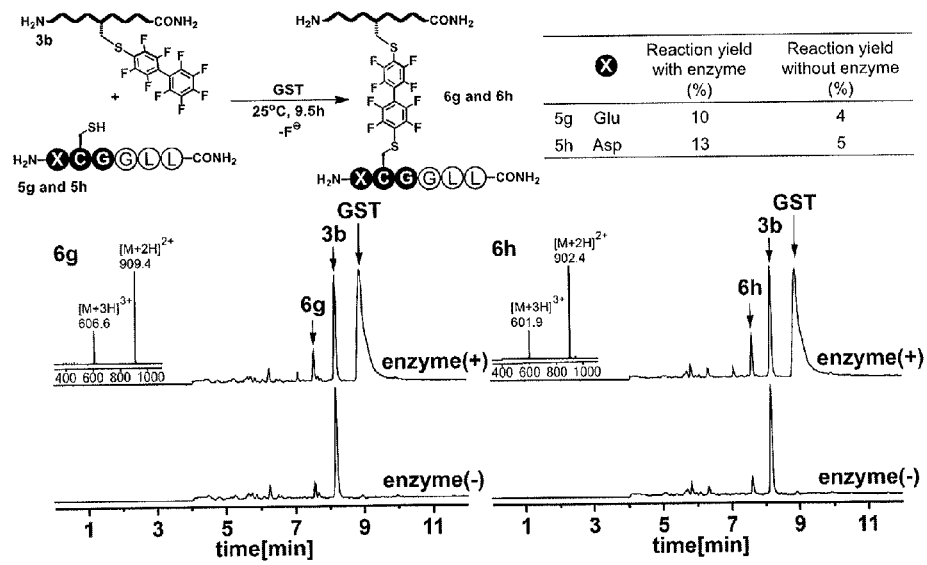
FIG. 59 depicts a GST-catalyzed cysteine arylation of N-terminal Glu-Cys-Gly and Asp-Cys-Gly sequences. Reaction conditions: 1 mM 3b, 10 mM 5g or 5h, 2 mg/mL GST, 20 mM TCEP.HCl, 0.1 M phosphate, pH 9.0, 25° C., 9.5 hours. Total ion current (TIC) LC traces are shown; mass spectra of LC peaks at highest intensity are shown as an inset. Figure discloses SEQ ID NOS 133-134, respectively, in order of appearance.
Figure 60:
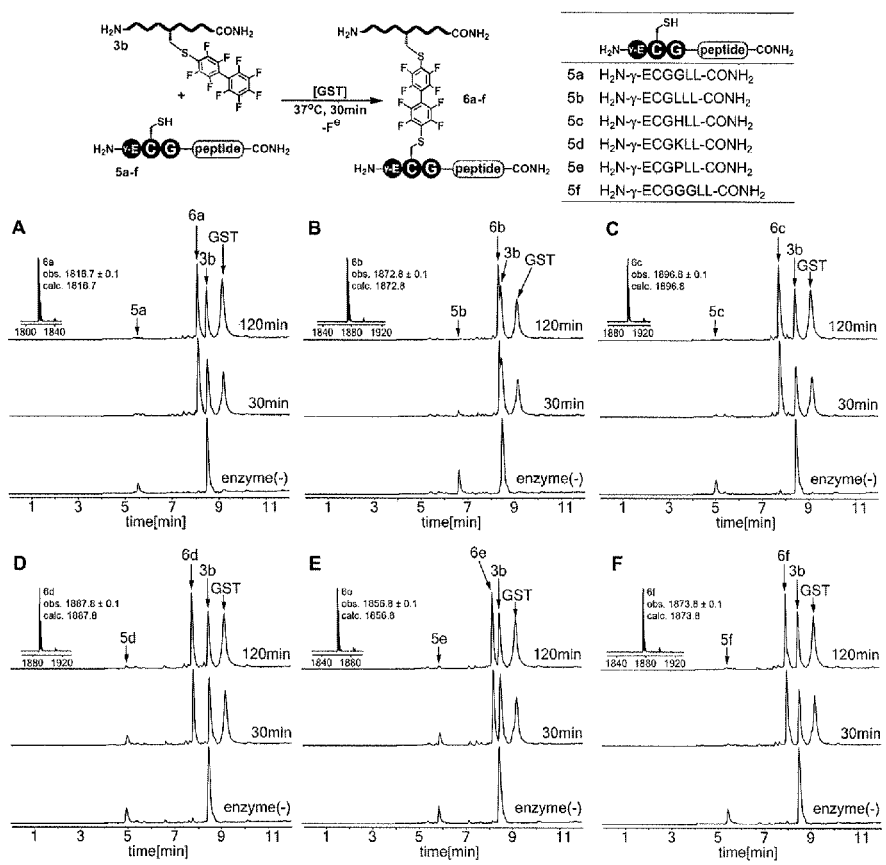
FIG. 60 depicts reactions of peptide 3b with peptides containing N-terminal γ-Glu-Cys-Gly sequence under GST catalysis. Panels (A)-(F) show the LCMS analysis of each crude reaction with 5a-f at 30 minutes (center chrotogram) and 120 minutes (top chromatogram). Bottom chromatogram in each panel represents a control experiment conducted without enzyme at 120 minutes. Total ion current (TIC) LC traces are shown; mass spectra of LC peaks at highest intensity are shown as an inset. Figure discloses SEQ ID NOS 114-119, respectively, in order of appearance.
Figure 61:
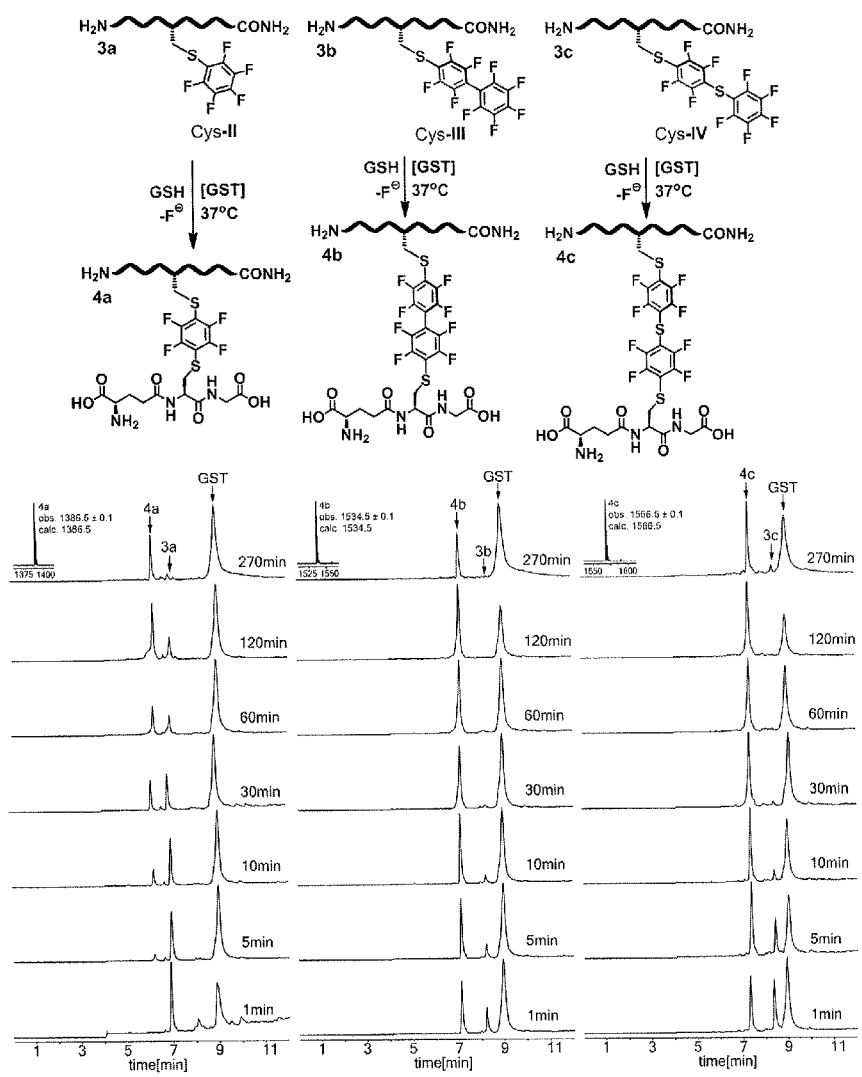
FIG. 61 depicts LC traces of GST-catalyzed conjugation of GSH to peptides 3a-c acquired at multiple timepoints during the reaction. Total ion current (TIC) LC traces are shown; mass spectra of LC peaks at highest intensity are shown as an inset.
Figure 62:
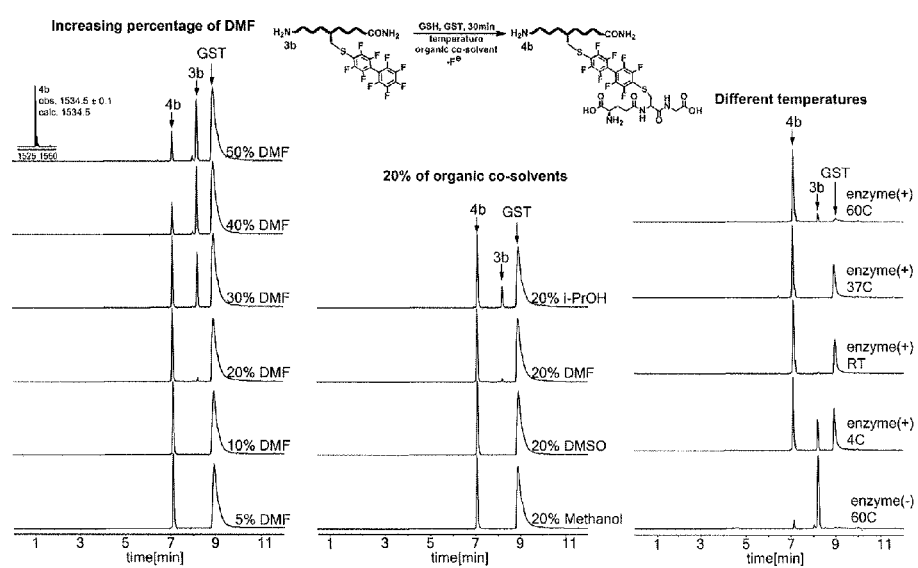
FIG. 62 depicts a GST-catalyzed conjugation of GSH to peptide containing Cys-II residue with mixed solvents at variable conditions and temperatures. Total ion current (TIC) LC traces are shown; mass spectra of LC peaks at highest intensity are shown as an inset.
Figure 63:
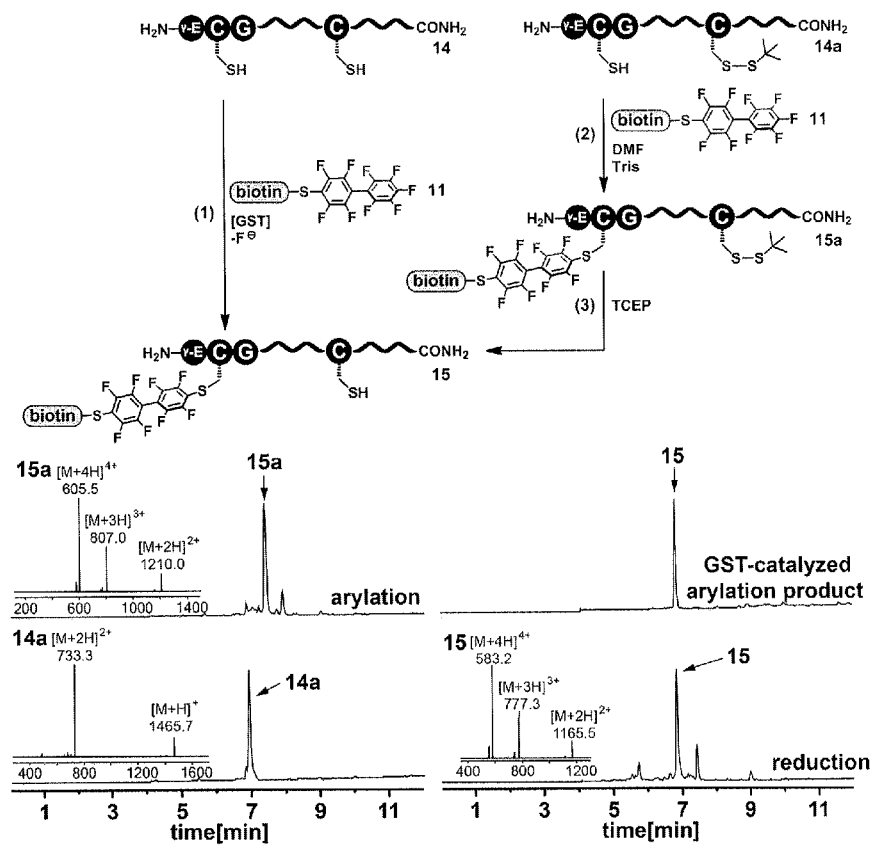
FIG. 63 depicts a synthesis of authentic peptide 15 by protecting-group chemistry. GST-catalyzed arylation product and authentic product had same retention time at 6.85 minutes. Reaction conditions: (1) same as those described in FIG. 57; (2) 1 mM 14a, 1 mM 11, 10 mM Tris base, DMF, room temperature, 30 minutes; (3) Equal volume of 1 M phosphate, 200 mM TCEP.HCl, pH 8.0 was added to crude reaction mixture from (2), and the resulting reaction mixture was left at room temperature for 10 minutes before subjected to LCMS analysis. Total ion current (TIC) LC traces are shown; mass spectra of LC peaks at highest intensity are shown as an inset.

All yields shown were determined by measuring UV absorption at =280 nm using LCMS data. First, using Agilent Mass Hunter software package, the peak areas for all relevant species on the chromatogram were integrated. For all reactions, the relevant peaks from UV absorption spectra at λ=280 nm arise from species containing perfluoroaromatic moieties. In FIG. 2 and FIG. 4, no products were generated in reactions without enzyme, and clean conversions of substrates to GST-catalyzed products were observed. For these reactions, yields were calculated using the following equation: % yield=(1−$S_E$/$S_C$)×100, where $S_E$—peak area of peptide substrates containing perfluoroaromatic moieties in enzymatic reactions and $S_C$—peak area of those peptide substrates in control reaction without enzyme. For reactions in FIG. 59, both the yields of enzymatic reactions and reactions without enzyme are calculated using equation: % yield=(1−$S_E$/$S_C$)×100, where $S_E$—peak area of peptide substrates containing perfluoroacromatic moieties in enzymatic reaction or control reaction without enzyme, and $S_C$—peak area of reaction with only peptide 3b. For reactions in FIG. 60, yields were calculated using the following equation to account for two equivalents of peptide 3b used relative to peptides 5a-f: % yield=(2−$S_E$/$S_C$)×100, where $S_E$—peak area of peptide 3b in enzymatic reaction and $S_C$—peak area of peptide 3b in control reaction without enzyme.

General Protocol for Preparation of Peptides 3a-c

Figure 48:
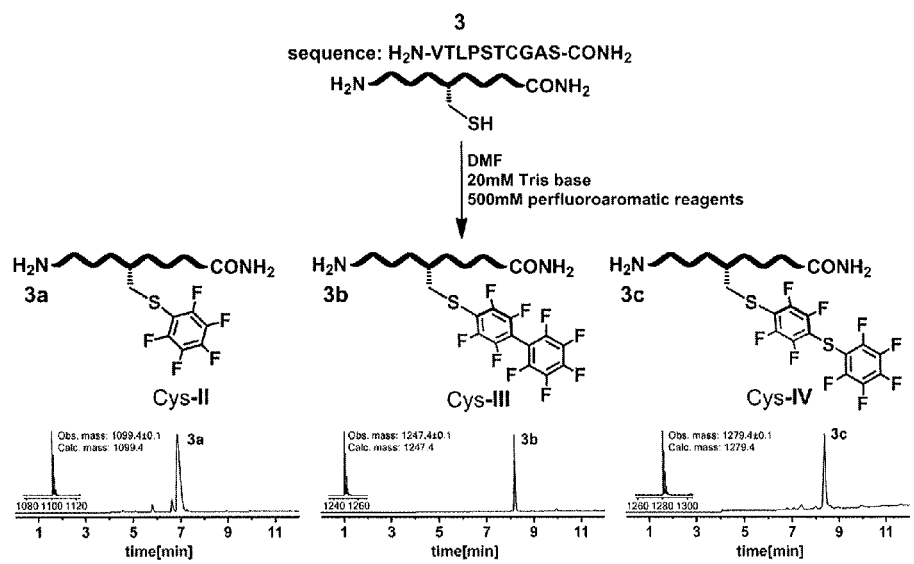
FIG. 48 depicts one preparation of peptides 3a-c. Total ion current (TIC) LC traces are shown; mass spectra of LC peaks at highest intensity are shown as an inset (SEQ ID NO: 113).

To a solid sample of peptide 3 (5 µmoles) dissolved in 20 mM Tris base in 1 mL of DMF in a plastic Eppendorf tube was added 500 µmoles of perfluoroaromatic reagent (hexafluorobenzene for 3a, decafluorobiphenyl for 3b, decafluorobiphenyl sulfide for 3c). The tube was vortexed to ensure complete reagent mixing and left at room temperature for 1 hour. Reaction mixtures were characterized by LCMS analysis. Resulting reaction mixtures were quenched by addition of 20 mL of 95% A: 5% B. Peptides 3a and 3c were purified by solid-phase extraction using Grace $C_{18}$ SPE Maxi-Clean Cartridges (Deerfield, Ill.) according to the manufacturer's protocol (FIG. 48, left and right chromatograms), and peptide 3b was purified by RP-HPLC (FIG. 48, chromatogram in the center).

Figure 49:
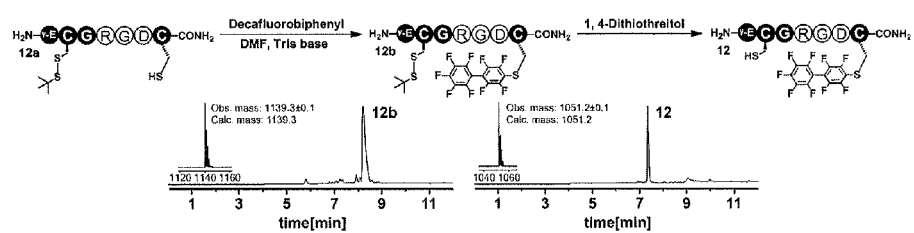
FIG. 49 depicts one preparation of peptide 12. Total ion current (TIC) LC traces are shown; mass spectra of LC peaks at highest intensity are shown as an inset. Figure discloses SEQ ID NOS 126-127 and 78, respectively, in order of appearance.

Preparation of peptides 12a and 12b (1) To a solid sample of peptide 12a (5 µmoles) dissolved in 20 mM Tris base in 1 mL of DMF in a plastic Eppendorf tube was added 500 µmoles of decafluorobiphenyl. The tube was vortexed to ensure complete reagent mixing and left at room temperature for 1 hour. The reaction mixture was characterized by LCMS analysis. Resulting reaction mixture was quenched by addition of 20 mL of 95% A: 5% B. Peptide 12b was purified by solid-phase extraction using Grace $C_{18}$ SPE Maxi-Clean Cartridge according to the manufacturer's protocol. Fractions were characterized by LCMS analysis (FIG. 49, left); pure fractions were collected and lyophilized.

(2) Peptide 12b was dissolved in water at 10 mM concentration. To 100 µL of this solution was added 20 µL of 1 M phosphate (pH 8.0) and 100 µL of 200 mM 1,4-dithiothreitol (DTT). The reaction mixture was incubated in 37° C. water bath for 1 hour and characterized by LCMS analysis. The crude reaction mixture was subjected to RP-HPLC purification; pure fractions were identified by LCMS analysis (FIG. 49, right), collected, and lyophilized.

Preparation of Biotin Probe 11

Figure 50:
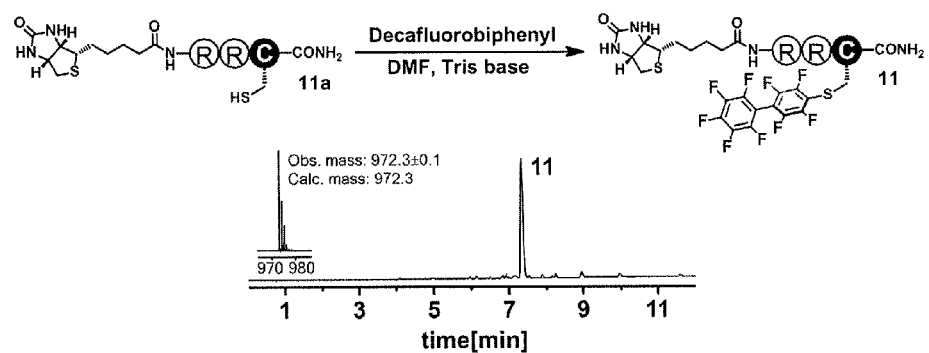
FIG. 50 depicts one preparation of biotin probe 11. Total ion current (TIC) LC trace is shown; mass spectrum of the LC peak at highest intensity is shown as an inset.

Peptide 11a was synthesized by Fmoc-SPPS using biotin as the last amino acid. To a solid sample of peptide 11a (5 µmoles) in a plastic Eppendorf tube dissolved in 20 mM Tris base in 1 mL of DMF was added 500 µmoles of decafluorobiphenyl. The tube was vortexed and left at room temperature for 1 hour. Reaction mixtures were characterized by LCMS analysis. Resulting reaction mixtures were quenched by addition of 20 mL of 95% A: 5% B. Peptide 11 was purified by RP-HPLC. Pure fractions were identified by LCMS analysis (FIG. 50), collected, and lyophilized.

Expression and Purification of A1C-LFN Protein

The A1C-LFN construct was cloned from pET-SUMO-LFN-LPSTGG-$H_6$ ("LPSTGG-$H_6$" disclosed as SEQ ID NO: 31) using QuickChange Lightening Site-Directed Mutagenesis kit according to the manufacturer's protocol. The generated construct encoded for the following protein sequence (the product of SUMO removal is shown in bold):

SUMO-A1C-LFN-$H_6$ ("$H_6$" disclosed as SEQ ID NO: 32)

MSDSEVNQEAKPEVKPEVKPETHIN-
LKVSDGSSEIFFKIKKTTPLRRLMEAF-
AKRQGKEM DSLRFLYDGIRIQADQT-
PEDLDMEDNDHEAHREQIGGCGGHGDVGMHVKE-
KEKNKD ENKRKDEERNKTQEEHLKE-
IMKHIVKIEVKGEEAVKKEAAEKLLE-
KVPSDVLEMY KAIGGKIYIVDGDITKHIS-
LEALSEDKKKIKDIYGKDALLHEHYVYAKEGYEPVLVI
QSSEDYVENTEKALN-
VYYEIGKILSRDILSKINQPYQKFLDV-
LNTIKNASDSDGQDLL FTNQLKEHPTDFS-
VEFLEQNSNEVQEVFAKAFAYYIEPQHRDVLQLYAPE-
AFNYMD KFNEQEINLSLEELKDQRLPSTG-
GHHHHHH                     (SEQ ID NO: 33)

E. coli BL21(DE3) cells transformed with SUMO-A1C-LFN-LPSTGG-$H_6$ ("LPSTGG-$H_6$" disclosed as SEQ ID NO: 31) construct were grown in 2 L of LB medium containing ampicillin (100 µg/mL) at 37 ℃ until $OD_{600}$=0.6. Then, expression was induced by addition of 0.5 mM IPTG overnight at 37 ℃. After harvesting the cells by centrifugation (6,000 rpm, 30 min), the cell pellet was lysed by sonication in 50 mL of 50 mM Tris, 150 mM NaCl, pH 7.5 buffer containing 30 mg lysozyme, 2 mg DNase I, and 1 tablet of protease inhibitor cocktail. The suspension was centrifuged at 17,000 rpm for one hour to remove cell debris. The supernatant was loaded onto a 5 mL HisTrap FF crude Ni-NTA column (GE Healthcare, UK) and washed with 50 mL of 40 mM imidazole in 20 mM Tris, 150 mM NaCl, pH 8.5. The protein was eluted from the column with buffer containing 500 mM imidazole in 20 mM Tris, 150 mM NaCl, pH 8.5. Imidazole was removed from protein using HiPrep 26/10 Desalting column (GE Healthcare, UK) into 20 mM Tris, 150 mM NaCl, pH 7.5. Purified protein was analyzed using an Any kD Mini-PROTEAN TGX Precast Gel (Bio-Rad, CA). In addition, the protein was analyzed by LCMS analysis to confirm its purity and molecular weight analyzed via high-resolution ESI-QTOF MS.

SUMO group on SUMO-A1C-LFN-$H_6$ ("$H_6$" disclosed as SEQ ID NO: 32) was cleaved first by incubating 1 µg SUMO protease per mg protein at room temperature for 90 minutes. The crude reaction mixture was loaded onto a 5 mL HisTrap FF crude Ni-NTA column (GE Healthcare, UK) and washed with 50 mL of 40 mM imidazole in 20 mM Tris, 150 mM NaCl, pH 8.5. The A1C-LFN-$H_6$ ("$H_6$" disclosed as SEQ ID NO: 32) protein was eluted from the column with buffer containing 500 mM imidazole in 20 mM Tris, 150 mM NaCl, pH 8.5. Imidazole was removed from protein using HiPrep 26/10 Desalting column (GE Healthcare, UK) into 20 mM Tris, 150 mM NaCl, pH 8.5. Purified protein was analyzed using an Any kD Mini-PROTEAN TGX Precast Gel (Bio-Rad, CA). In addition, the protein was analyzed by LCMS to confirm the purity and molecular weight analyzed via high-resolution ESI-QTOF MS. The A1C-LFN-$H_6$ ("$H_6$" disclosed as SEQ ID NO: 32) protein was purified as disulfide linked dimer (FIG. 51, observed mass: 63733.3, calculated mass: 63731.6).

Figure 51:
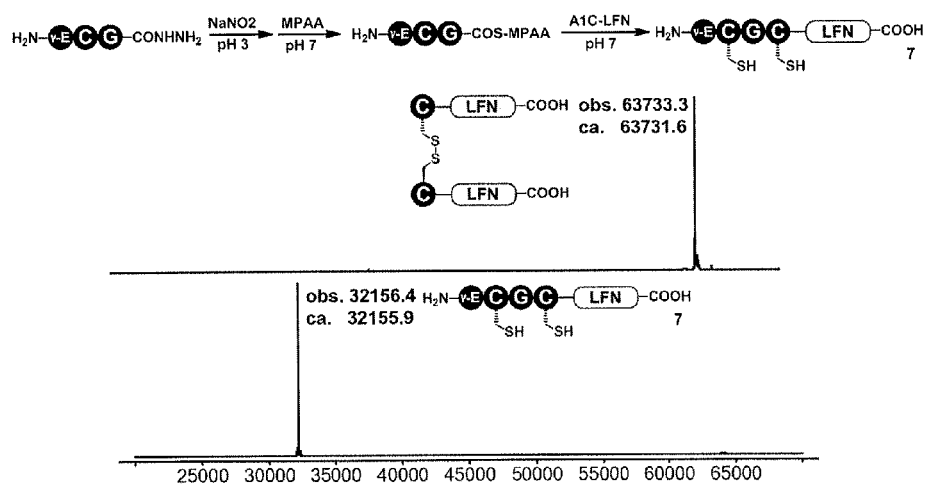
FIG. 51 depicts one preparation of protein 7 with N-terminal γ-Glu-Cys-Gly by peptide hydrazide ligation. Deconvoluted mass spectra obtained from LCMS analysis of these samples are shown. Figure discloses SEQ ID NOS 94-95, respectively, in order of appearance.

Preparation of protein 7 by hydrazide ligation

γ-Glu-Cys-Gly-CONHNH$_2$ (5i) was prepared by Fmoc-SPPS using hydrazide resin. To 4 μmoles of peptide hydrazide dissolved in 0.1 M phosphate, 6 M guanidinium hydrochloride, pH 3.0 was added 100 μL of 100 mM NaNO$_2$ in water at −10° C. and reacted for 20 minutes at the same temperature. Then 500 μL of 200 mM 4-mercaptophenyl acetic acid (MPAA) in 0.1 M phosphate (pH 7.0) was added. The pH of the reaction mixture was adjusted to 7.0 by addition of 5 M sodium hydroxide. The reaction mixture was left at room temperature for 10 minutes and analyzed by LCMS. This crude peptide mixture was then used directly in ligation reaction with protein A1C-LFN. To 50 μL crude thioester mixture was added 10 μL of 40 mg/mL A1C-LFN and 10 μL of 1 M phosphate, 200 mM TCEP.HCl, pH 7.0. The reaction mixture was left at room temperature for 2 hours and characterized by LCMS analysis (FIG. 51). Protein 7 was purified by dialysis against 20 mM Tris, 150 mM NaCl, pH 7.5 buffer.

GST-Catalyzed Reactions

Typical GST-catalyzed reactions were performed on a 10 μL scale. Peptide substrates were dissolved in water to make 10 mM stock solutions. Then substrates were mixed with 2 μL of GST stock solution (10 mg/mL), 1 μL reaction buffer (1 M phosphate, 200 mM TCEP.HCl, pH 8.0), then water was added to a total volume of 10 μL. Unless otherwise noted, reactions were incubated at 37° C. water bath, quenched by addition of 90 μL of 50% A: 50% B, and subjected to LCMS analysis.

Comparing the Activity of Various Sources of GSTs

Figure 52:
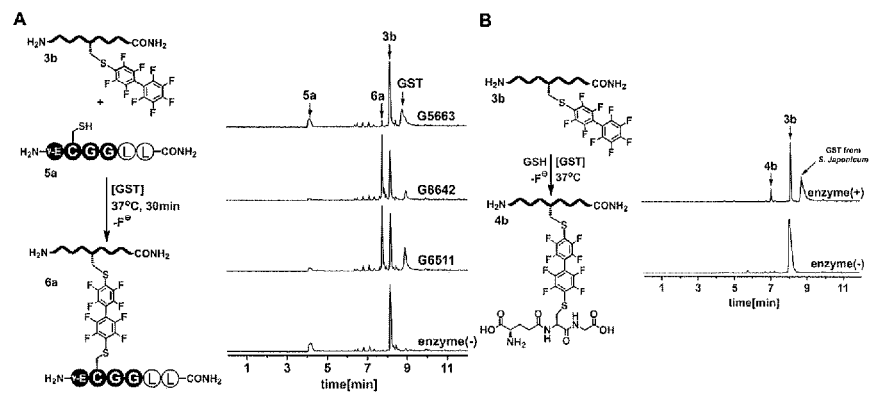
FIG. 52 depicts a comparison of the activities of various GSTs. (A) Reaction conditions: 2 mM 3b, 1 mM 5a, 2 mg/mL GST, 20 mM TCEP.HCl, 0.1 M phosphate, pH 8.0, 37° C. Crude reactions at 30 minutes were subjected to LCMS analysis (figure discloses SEQ ID NOS 114 and 128, respectively, in order of appearance). (B) Reaction conditions: 1 mM 3b, 1 mM GSH, 2 mg/mL GST, 20 mM TCEP.HCl, 0.1 M phosphate, pH 8.0, 37° C. Crude reactions at 30 minutes were subjected to LCMS analysis. Total ion current (TIC) LC traces are shown.
Figure 53:
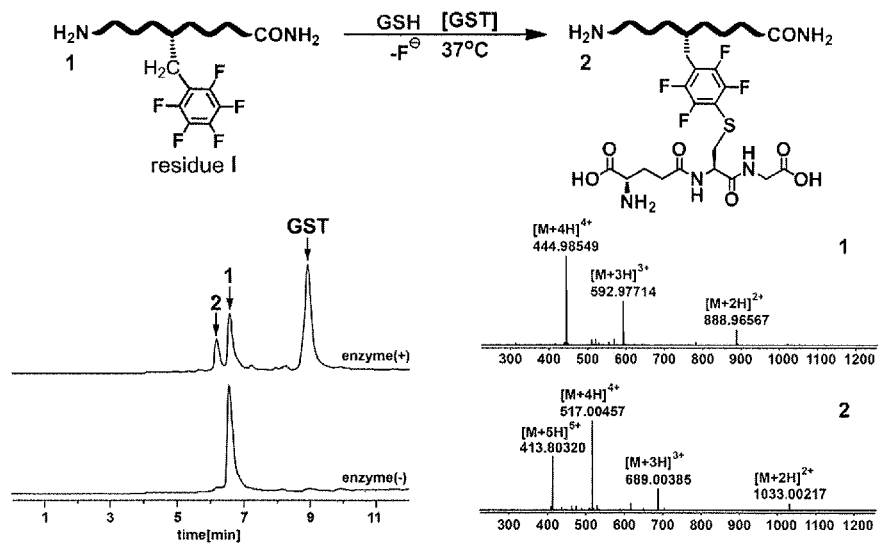
FIG. 53 depicts a GST-catalyzed conjugation of GSH to L-pentafluorophenylalanine residue (residue I). Total ion current (TIC) LC traces are shown; mass spectra of LC peaks at highest intensity are shown as an inset.
Figure 54:
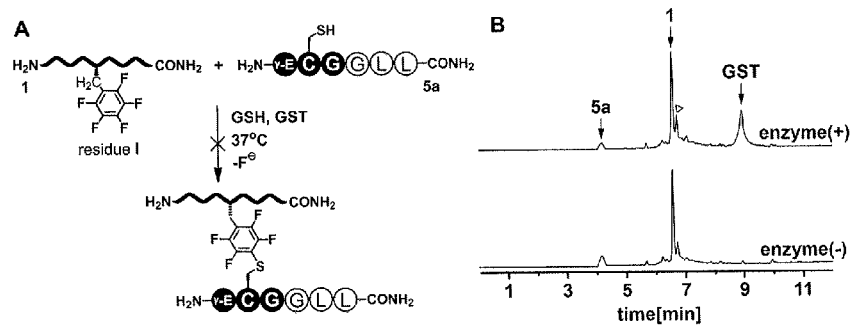
FIG. 54 depicts reactions of peptide 1 containing L-pentafluorophenylalanine residue (residue I) with peptide 5a containing N-terminal γ-Glu-Cys-Gly sequence. No product was observed with the addition of GST. (A) Reaction conditions: 2 mM 1, 1 mM 5a, 2 mg/mL GST, 20 mM TCEP.HCl, 0.1 M phosphate, pH 8.0, 37° C. (figure discloses SEQ ID NOS 114 and 129, respectively, in order of appearance). (B) LCMS analysis of crude reactions at 10 hours. Total ion current (TIC) LC traces are shown. Bottom chromatogram represents a control experiment conducted without an enzyme. V is unreactive impurity contaminant of 1.
Figure 55:
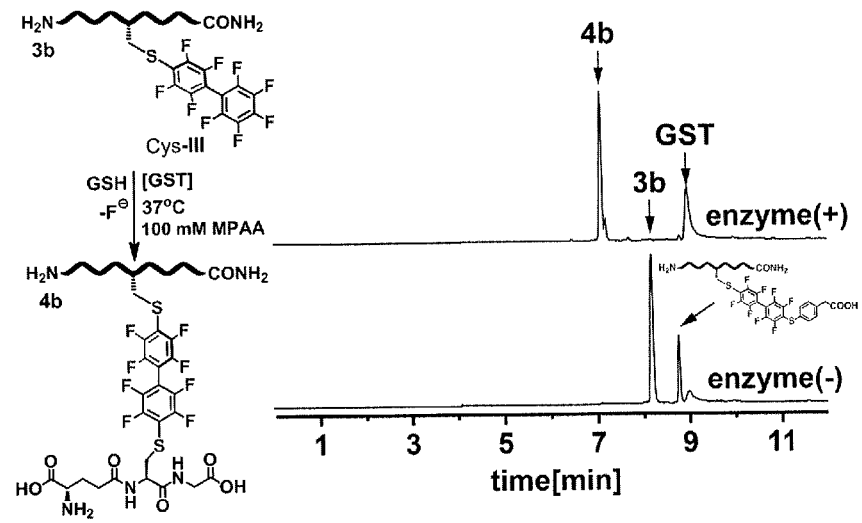
FIG. 55 depicts a GST-catalyzed conjugation of GSH to peptide 3b in the presence of competing 4-mercaptophenylacetic acid (MPAA). Reaction conditions: 1 mM 3b, 1 mM GSH, 100 mM MPAA, 2 mg/mL GST, 20 mM TCEP.HCl, 0.1 M phosphate, pH 8.0, 37° C., 30 min. Total ion current (TIC) LC traces are shown. While in non-enzymatic reaction MPAA could be arylated, in GST-catalyzed reaction, the GSH-arylated product was exclusively generated.
Figure 56:
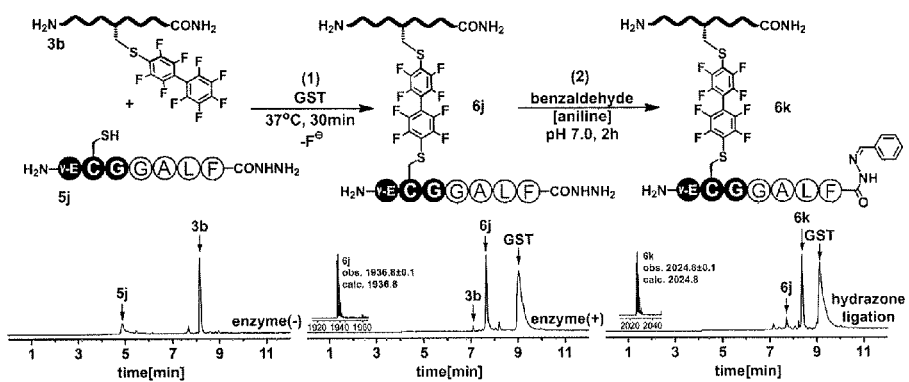
FIG. 56 depicts a GST-catalyzed conjugation between peptide hydrazide 5j and peptide 3b. The peptide hydrazide was further functionalized by aniline-catalyzed hydrazone ligation with benzaldehyde to give peptide 6k. Reaction conditions: (1) 1 mM 3b, 1 mM 5j, 2 mg/mL GST, 20 mM TCEP HCl, 0.1 M phosphate, pH 8.0, 37° C., 30 min. (2) 2 mM benzaldehyde dissolved in 0.1 M phosphate (pH 7.0) and 200 mM aniline dissolved in 0.1 M phosphate (pH 7.0) were added in situ to the crude reaction mixture resulting from (1). The final reaction conditions were: 100 μM 6j, 400 μM benzaldehyde, 100 mM aniline, 0.1 M phosphate, pH 7.0, two hours. Total ion current (TIC) LC traces are shown. Left chromatogram represents a control reaction (1) conducted without enzyme. Figure discloses SEQ ID NOS 122 and 130-131, respectively, in order of appearance.
Figure 57:
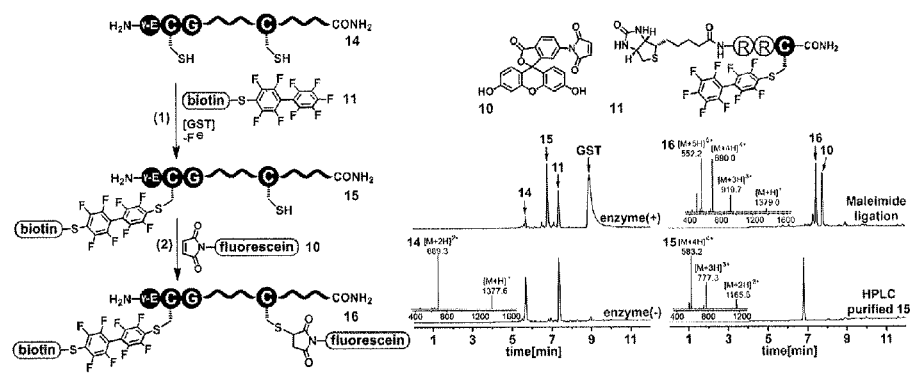
FIG. 57 depicts sequential labeling of biotin and fluorescein probes to peptide 14 containing two cysteines. Peptide sequence: $H_2N$-γ-ECGPTAAKESCLL-$CONH_2$ (SEQ ID NO: 6). Reaction conditions: (1) 0.5 mM 14, 1 mM 11, 2 mg/mL GST, 20 mM TCEP.HCl, 0.1 M phosphate, pH 8.0, 37° C., 40 minutes; (2) 0.5 mM 15, 1 mM 10, 0.1 M phosphate, pH 6.0, 10 minutes. Total ion current (TIC) LC traces are shown; mass spectra of LC peaks at highest intensity are shown as an inset.
Figure 58:
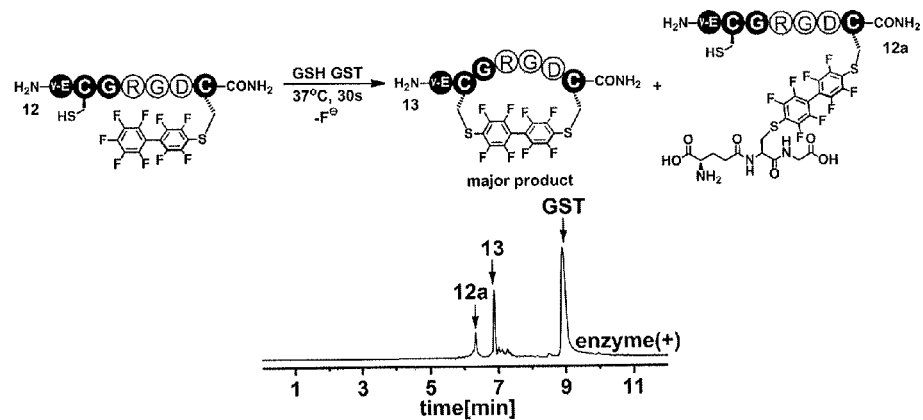
FIG. 58 depicts a GST-catalyzed macrocyclization in the presence of competing GSH. Reaction conditions: 1 mM 12, 1 mM GSH, 2 mg/mL GST, 20 mM TCEP.HCl, 0.1 M phosphate, pH 8.0, 37° C. LCMS trace is shown as total ion current. Figure discloses SEQ ID NOS 78-79 and 132, respectively, in order of appearance.

Different GSTs were used to catalyze the conjugation of peptide 3b with peptide 5a (FIG. 52A). GST from equine liver and GST from human placenta showed similar activity: peptide 5a was converted nearly quantitatively to product 6a within 30 min under the catalysis of these two isozyme mixtures. However, GST from *Schistosoma Japonicum* showed no significant activity. We also found the activity of GST from *Schistosoma Japonicum* for conjugation of GSH to peptide 3b (FIG. 51B) was significantly lower than that of GST from equine liver.

Selectivity of GST-Catalyzed Arylation

Figure 64:
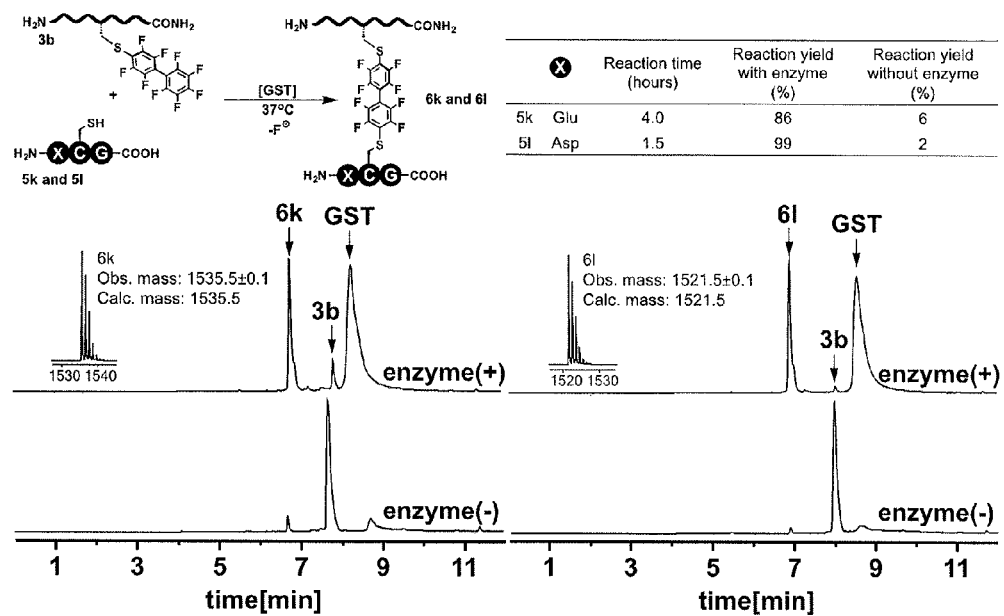
FIG. 64 depicts a GST-catalyzed conjugation of tri-peptide Glu-Cys-Gly and Asp-Cys-Gly to peptide containing Cys-II residue. Reaction conditions: 1 mM 3b, 10 mM 5k or 5l, 2 mg/mL GST, 20 mM TCEP.HCl, 0.1 M phosphate, pH 9.0, 25° C. Total ion current (TIC) LC traces are shown; mass spectra of LC peaks at highest intensity are shown as an inset. Tri-peptide Glu-Cys-Gly and Asp-Cys-Gly were synthesized by standard Fmoc-SPPS using 2-chlorotrityl resin from Anaspec (Fermont, Calif.).
Figure 65:
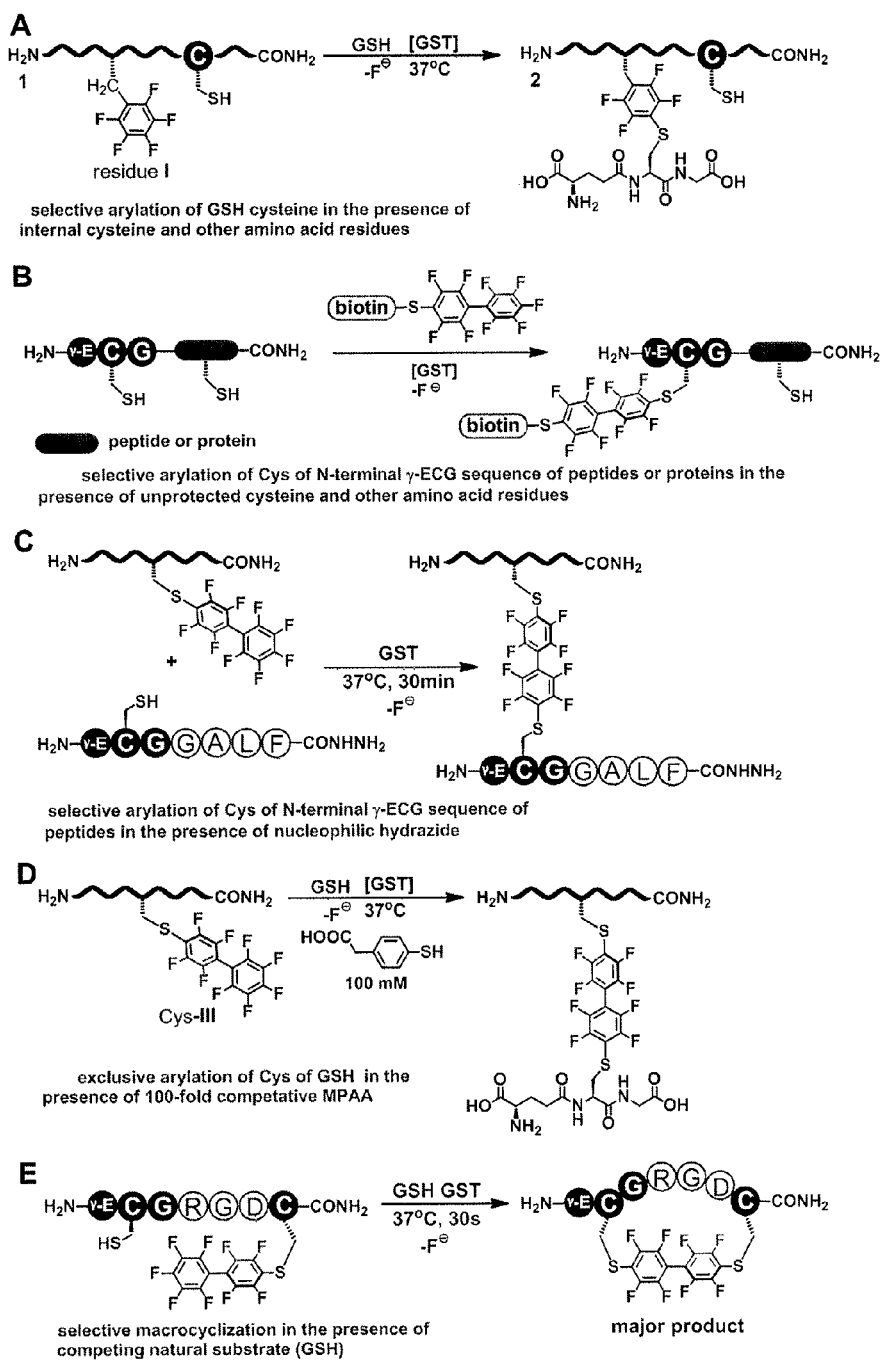
FIG. 65 depicts a summary of experiments demonstrating the chemo- and regioselectivity of GST catalyzed "click" ligation. Figure discloses SEQ ID NOS 122, 130 and 78-79, respectively, in order of appearance.
Figure 66:
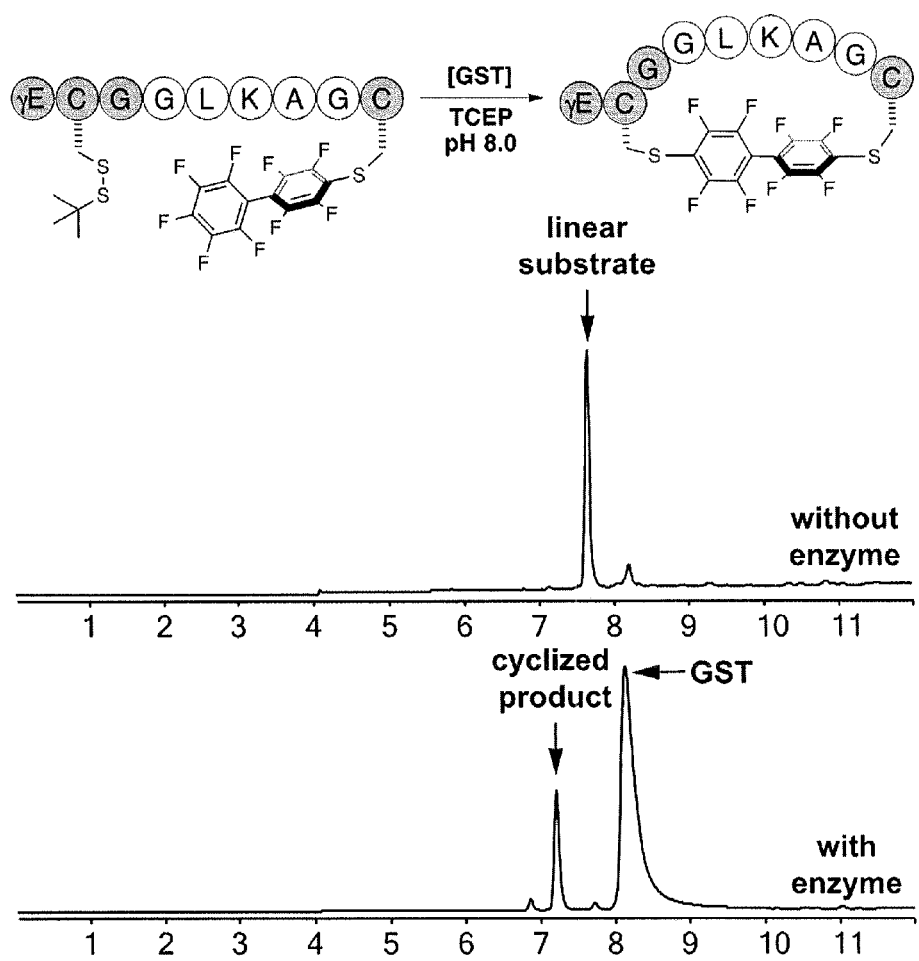
FIG. 66 depicts a GST-catalyzed cyclization reaction. Reaction conditions: 0.1 mM peptide, 0.2 mg/mL GST, 0.1 M phosphate, 20 mM TCEP, pH 8.0, room temperature, 5 min. Figure discloses SEQ ID NOS 135-136, respectively, in order of appearance.
Figure 67:
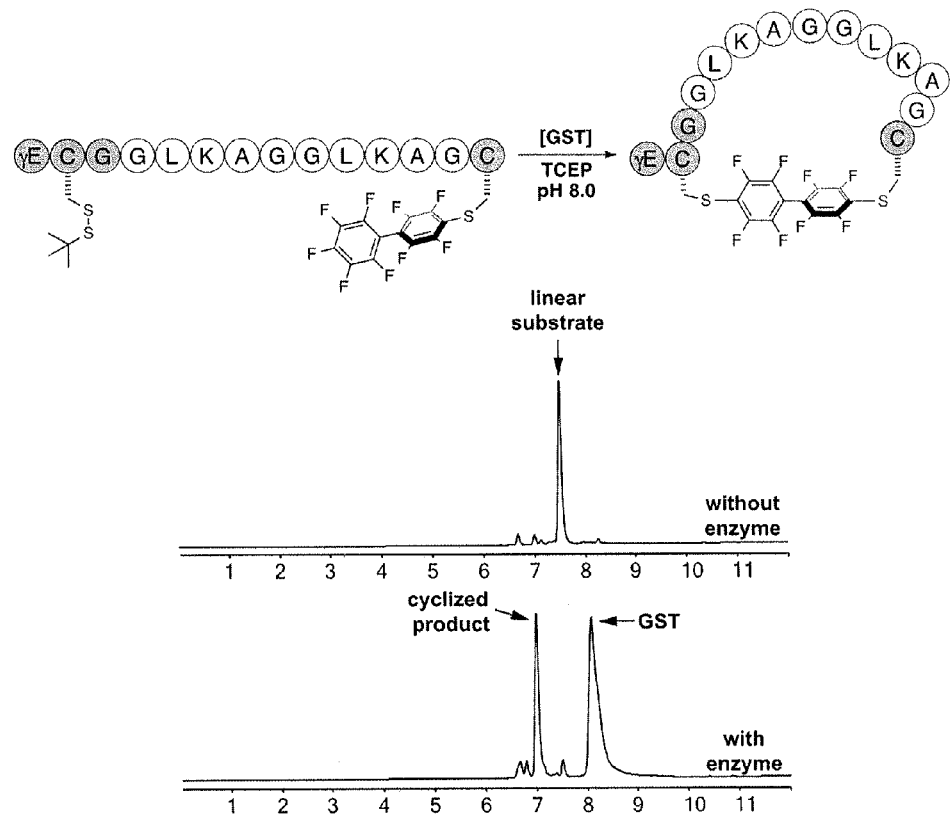
FIG. 67 depicts a GST-catalyzed cyclization reaction. Reaction conditions: 0.1 mM peptide, 0.2 mg/mL GST, 0.1 M phosphate, 20 mM TCEP, pH 8.0, room temperature, 60 min. Figure discloses SEQ ID NOS 137-138, respectively, in order of appearance.
Figure 68:
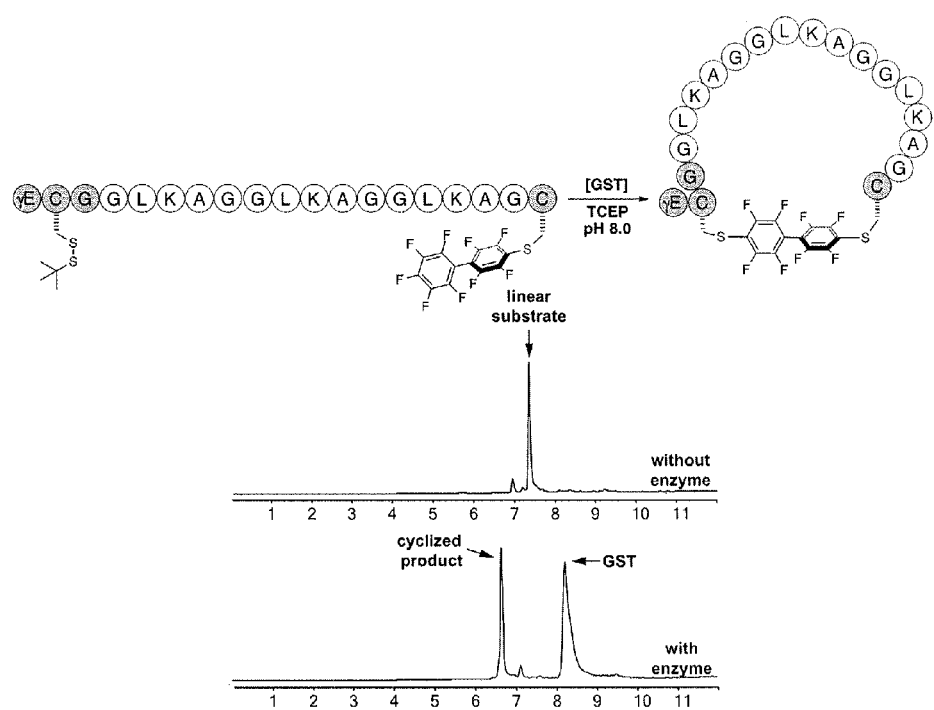
FIG. 68 depicts a GST-catalyzed cyclization reaction. Reaction conditions: 0.1 mM peptide, 0.2 mg/mL GST, 0.1 M phosphate, 20 mM TCEP, pH 8.0, room temperature, 120 min. Figure discloses SEQ ID NOS 139-140, respectively, in order of appearance.

The developed GST-catalyzed reaction is highly selective for arylation of cysteine site at N-terminal γ-Glu-Cys-Gly sequence of peptides or proteins. This unique selectivity enabled us to modify cysteines in the presence of other competing reactive sites or reagents. Summary of the experiments performed to demonstrate this unique selectivity is shown in FIG. 64.

INCORPORATION BY REFERENCE

All of the U.S. patents and U.S. published patent applications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:
1. A compound
(a) comprising substructure I:

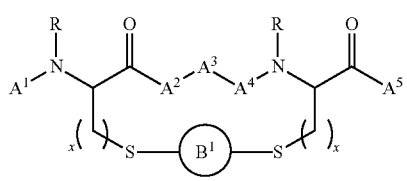

wherein, independently for each occurrence,
$A^1$ is H, an amine protecting group, a natural or unnatural amino acid, a peptide, an oligopeptide, a polypeptide, or a protein;
$A^2$, $A^3$, and $A^4$ are selected from the group consisting of a natural amino acid, an unnatural amino acid, and a plurality of natural amino acids or unnatural amino acids;
x is 0, 1, 2, 3, 4, 5, or 6;
$A^5$ is OH, a carboxylate protecting group, a natural or unnatural amino acid, a peptide, an oligopeptide, a polypeptide, or a protein; and

is a perfluorinated aryl para-substituted diradical; and
R is H or alkyl;

(b) comprising substructure II:

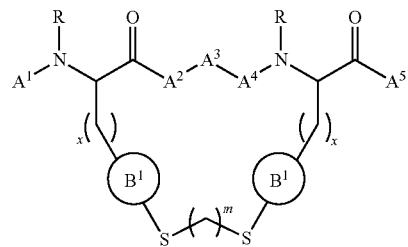

wherein, independently for each occurrence,
$A^1$ is H, an amine protecting group, a natural or unnatural amino acid, a peptide, an oligopeptide, a polypeptide, or a protein;
$A^2$, $A^3$, and $A^4$ are selected from the group consisting of a natural amino acid, an unnatural amino acid, and a plurality of natural amino acids or unnatural amino acids;
$A^5$ is OH, a carboxylate protecting group, a natural or unnatural amino acid, a peptide, an oligopeptide, a polypeptide, or a protein;

is a perfluorinated aryl para-substituted diradical;
x is 0, 1, 2, 3, 4, 5, or 6;
m is 1, 2, 3, 4, 5, or 6; and
R is H or alkyl;

(c) comprising substructure III:

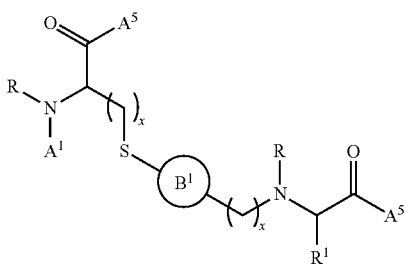

wherein, independently for each occurrence,
A¹ is H, an amine protecting group, a natural or unnatural amino acid, a peptide, an oligopeptide, a polypeptide, or a protein;
A⁵ is OH, a carboxylate protecting group, a natural or unnatural amino acid, a peptide, an oligopeptide, a polypeptide, or a protein;

is a perfluorinated aryl para-substituted diradical;
x is 0, 1, 2, 3, 4, 5, or 6;
R is H or alkyl; and
R¹ is H, alkyl, alkylthioalkyl, aralkyl, heteroaralkyl, hydroxyaralkyl, HO₂C-alkyl, H₂N—C(O)-alkyl, heterocycloalkyl, guanidinylalkyl, aminoalkyl, or hydroxyalkyl;

(d) comprising substructure IV:

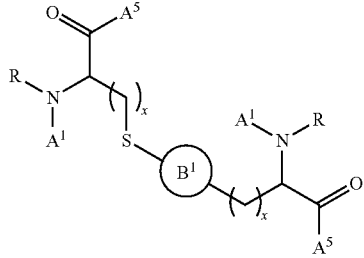

wherein, independently for each occurrence,
A¹ is H, an amine protecting group, a natural or unnatural amino acid, a peptide, an oligopeptide, a polypeptide, or a protein;
A⁵ is OH, a carboxylate protecting group, a natural or unnatural amino acid, a peptide, an oligopeptide, a polypeptide, or a protein;
x is 0, 1, 2, 3, 4, 5, or 6;

is a perfluorinated aryl para-substituted diradical; and
R is H or alkyl;

(e) comprising substructure V:

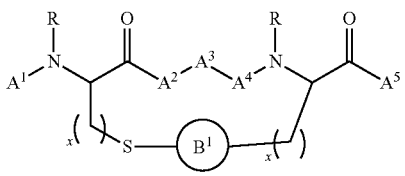

wherein, independently for each occurrence,
A¹ is H, an amine protecting group, a natural or unnatural amino acid, a peptide, an oligopeptide, a polypeptide, or a protein;
A², A³, and A⁴ are selected from the group consisting of a natural amino acid, an unnatural amino acid, and a plurality of natural amino acids or unnatural amino acids;
A⁵ is OH, a carboxylate protecting group, a natural or unnatural amino acid, a peptide, an oligopeptide, a polypeptide, or a protein;
x is 0, 1, 2, 3, 4, 5, or 6;

is a perfluorinated aryl para-substituted diradical; and
R is H or alkyl; or (f) comprising substructure VI:

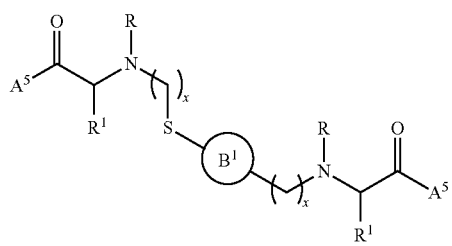

wherein, independently for each occurrence,
A⁵ is OH, a carboxylate protecting group, a natural or unnatural amino acid, a peptide, an oligopeptide, a polypeptide, or a protein;

is a perfluorinated aryl para-substituted diradical;
x is 0, 1, 2, 3, 4, 5, or 6;
R is H or alkyl; and
R¹ is H, alkyl, alkylthioalkyl, aralkyl, heteroaralkyl, hydroxyaralkyl, HO₂C-alkyl, H₂N—C(O)-alkyl, heterocycloalkyl, guanidinylalkyl, aminoalkyl, or hydroxyalkyl.

2. The compound of claim 1, wherein none of A¹, A², A³, A⁴, and A⁵ comprises cysteine.

3. The compound of claim 1, wherein one or more of $A^1$, $A^2$, $A^3$, $A^4$, and $A^5$ comprises arginine, histidine, lysine, aspartic acid, glutamic acid, serine, threonine, asparagine, glutamine, glycine, proline, alanine, valine, isoleucine, leucine, methionine, phenylalanine, tyrosine, or tryptophan.

4. The compound of claim 1, wherein

is 2,3,5,6-tetrafluorophenylene or 2,2',3,3',5,5',6,6'-octafluoro-1,1'-biphenyl-4,4'-ene.

5. The compound of claim 1, wherein R is H.

6. The compound of claim 1, wherein m is 2, 3, or 4.

7. The compound of claim 1, wherein $R^1$ is aminoalkyl or aralkyl.

8. The compound of claim 1, wherein the compound comprising substructure I is selected from the group consisting of (SEQ ID NOS 7-18, respectively, in order of appearance):

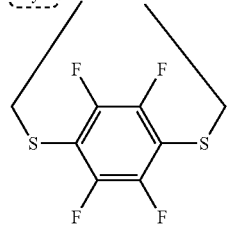

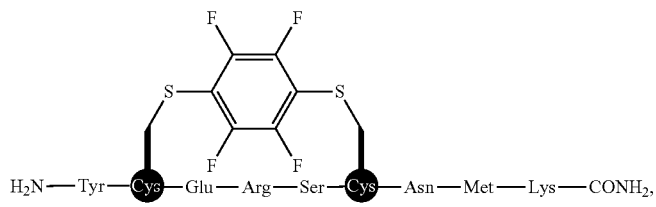

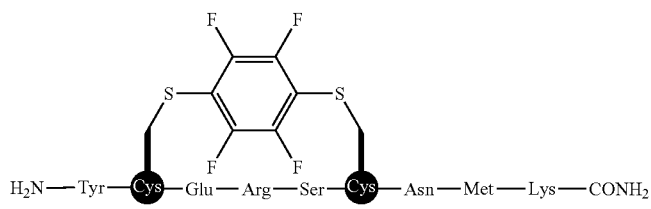

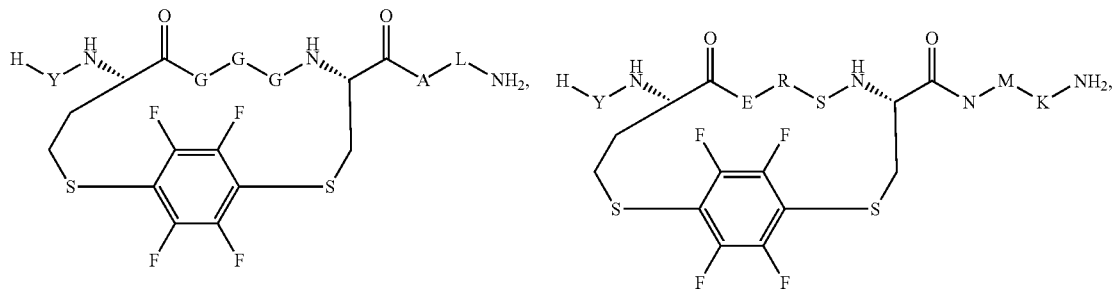

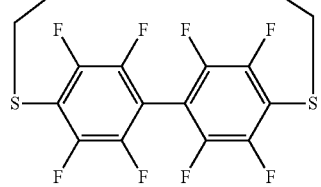

H₂N—Tyr—Cys—Glu—Arg—Ser—Cys—Asn—Met—Lys—CONH₂, (perfluorobiphenyl bis-thioether crosslink between two Cys residues)

H—I—T—P—●—N—L—L—●—Y—Y—G—K—K—K—NH₂, (perfluorobiphenyl bis-thioether crosslink)

[two additional cyclic peptide structures shown with perfluorobiphenyl thioether linkers]

H—Y—[cyclic]—G—G—[cyclic]—A—L—NH₂, and H—Y—[cyclic]—E—R—S—[cyclic]—N—M—K—NH₂.

9. The compound of claim 1, wherein the compound comprising substructure I is selected from the group consisting of (SEQ ID NOS 19-21, respectively, in order of appearance):

H₂N—T—A—W—Y—C—N—F(CF₃)—E—C—L—L—R—CONH₂, (perfluorobiphenyl bis-thioether crosslink between the two C residues)

HN—Ile—Thr—Phe—Cys—Asp—Leu—Leu—Cys—Tyr—Tyr—Gly—Lys—Lys—Lys—CONH₂, and
 |
 X (tetrafluorobenzene bis-thioether crosslink between the two Cys residues)

-continued

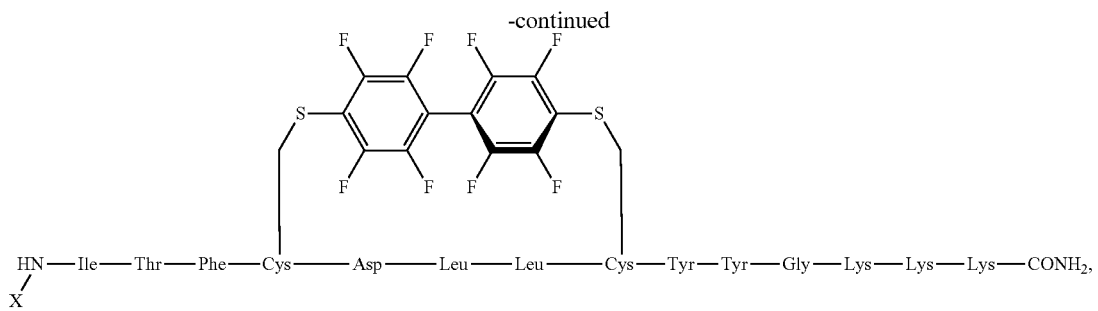

wherein X is H or β-Ala-FITC.

10. The compound of claim 1, wherein the compound comprising substructure II is selected from the group consisting of (SEQ ID NOS 22-23, respectively, in order of appearance):

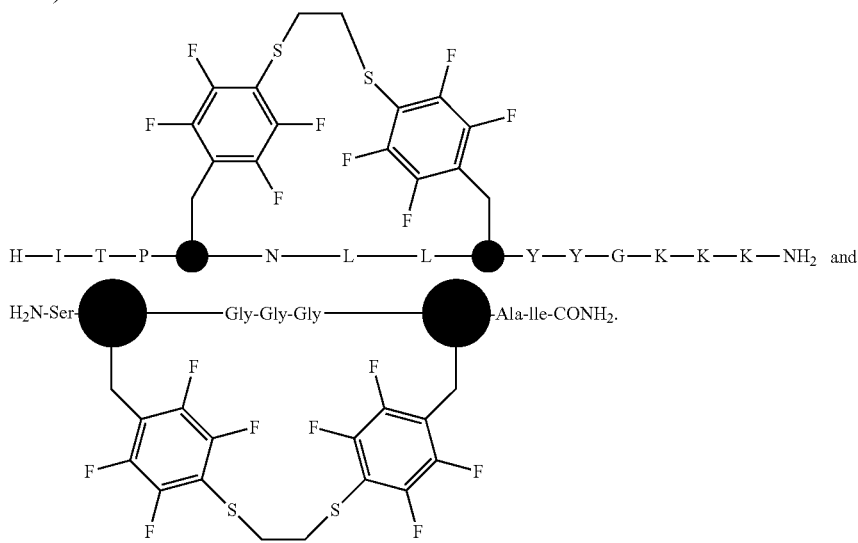

11. The compound of claim 1, wherein the compound comprising substructure VI is (SEQ ID NOS 24-25, respectively, in order of appearance)

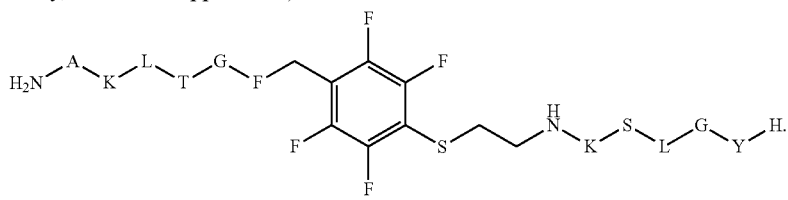

12. A compound comprising substructure XI or XII:

-continued

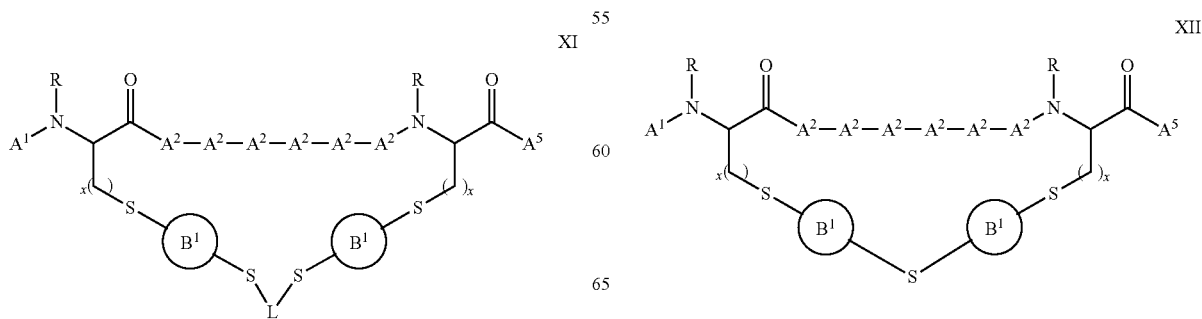

wherein, independently for each occurrence,
A$^1$ is H, an amine protecting group, a natural or unnatural amino acid, a peptide, an oligopeptide, a polypeptide, or a protein;
A$^2$ is selected from the group consisting of a natural amino acid, an unnatural amino acid, and a plurality of natural amino acids or unnatural amino acids;
A$^5$ is OH, a carboxylate protecting group, a natural or unnatural amino acid, a peptide, an oligopeptide, a polypeptide, or a protein;

is a perfluorinated aryl para-substituted diradical;
x is 0, 1, 2, 3, 4, 5, or 6;
R is H or alkyl; and
L is a substituted or unsubstituted alkyl diradical, a substituted or unsubstituted aryl diradical, or a substituted or unsubstituted aralkyl diradical.

13. The compound of claim 12, wherein the compound of substructure XI is (SEQ ID NO: 30):

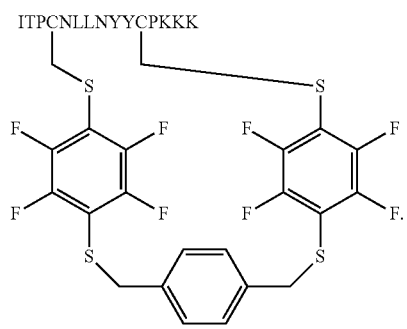

14. A method of making a compound
(a) according to Scheme 1, wherein the compound comprises substructure I:

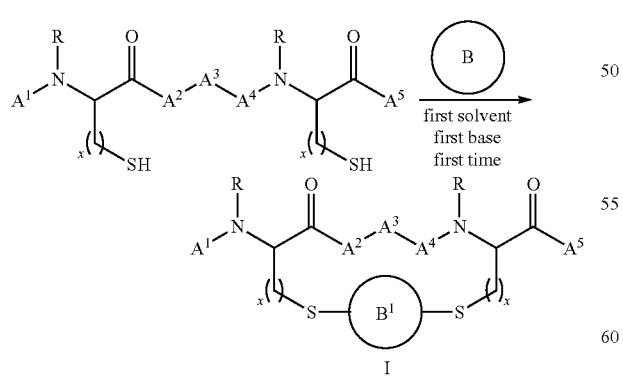

wherein, independently for each occurrence,
A$^1$ is H, an amine protecting group, a natural or unnatural amino acid, a peptide, an oligopeptide, a polypeptide, or a protein;
A$^2$, A$^3$, and A$^4$ are selected from the group consisting of a natural amino acid, an unnatural amino acid, and a plurality of natural amino acids or unnatural amino acids;
A$^5$ is OH, a carboxylate protecting group, a natural or unnatural amino acid, a peptide, an oligopeptide, a polypeptide, or a protein;
R is H or alkyl;
x is 0, 1, 2, 3, 4, 5, or 6;

is a perfluorinated aryl compound; and

is a perfluorinated aryl para-substituted diradical;
(b) according to Scheme 2, wherein the compound comprises substructure II:

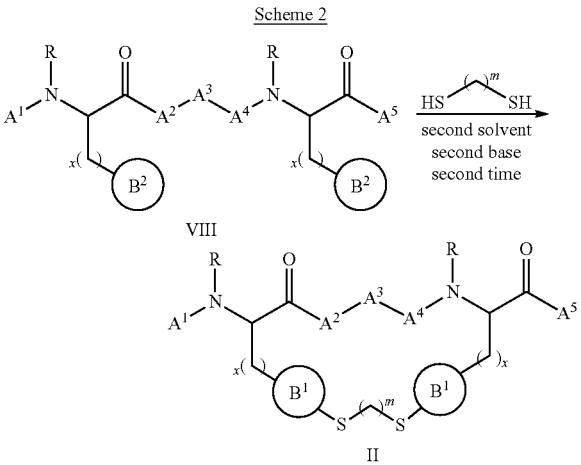

wherein, independently for each occurrence,
A$^1$ is H, an amine protecting group, a natural or unnatural amino acid, a peptide, an oligopeptide, a polypeptide, or a protein;
A$^2$, A$^3$, and A$^4$ are selected from the group consisting of a natural amino acid, an unnatural amino acid, and a plurality of natural amino acids or unnatural amino acids;
A$^5$ is OH, a carboxylate protecting group, a natural or unnatural amino acid, a peptide, an oligopeptide, a polypeptide, or a protein;
R is H or alkyl;
x is 0, 1, 2, 3, 4, 5, or 6;

is a perfluorinated aryl radical;
m is 1, 2, 3, 4, 5, or 6; and

is a perfluorinated aryl para-substituted diradical;

(c) according to Scheme 3, wherein the compound comprises substructure III:

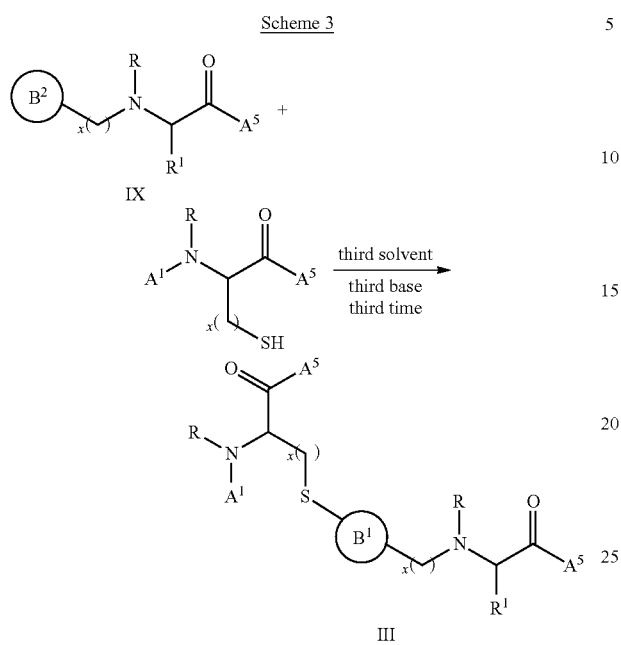

III wherein, independently for each occurrence,
A$^1$ is H, an amine protecting group, a natural or unnatural amino acid, a peptide, an oligopeptide, a polypeptide, or a protein;
A$^5$ is OH, a carboxylate protecting group, a natural or unnatural amino acid, a peptide, an oligopeptide, a polypeptide, or a protein;
R is H or alkyl;
x is 0, 1, 2, 3, 4, 5, or 6;

is a perfluorinated aryl radical;
R$^1$ is H, alkyl, alkylthioalkyl, aralkyl, heteroaralkyl, hydroxyaralkyl, HO$_2$C-alkyl, H$_2$N—C(O)-alkyl, heterocycloalkyl, guanidinylalkyl, aminoalkyl, or hydroxyalkyl; and

is a perfluorinated aryl para-substituted diradical;
(d) according to Scheme 4, wherein the compound comprises substructure IV:

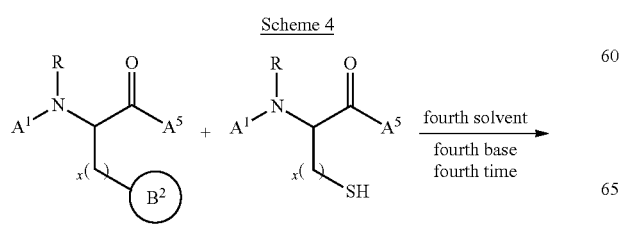

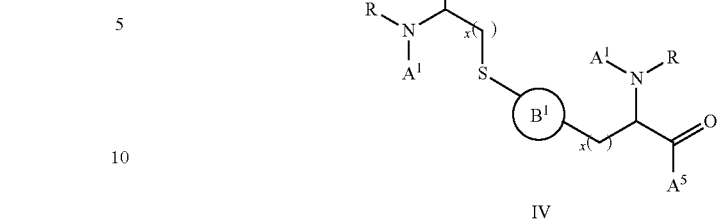

IV wherein, independently for each occurrence,
A$^1$ is H, an amine protecting group, a natural or unnatural amino acid, a peptide, an oligopeptide, a polypeptide, or a protein;
A$^5$ is OH, a carboxylate protecting group, a natural or unnatural amino acid, a peptide, an oligopeptide, a polypeptide, or a protein;
R is H or alkyl;
x is 0, 1, 2, 3, 4, 5, or 6;

is a perfluorinated aryl radical; and

is a perfluorinated aryl para-substituted diradical;
(e) according to Scheme 5, wherein the compound comprises substructure V:

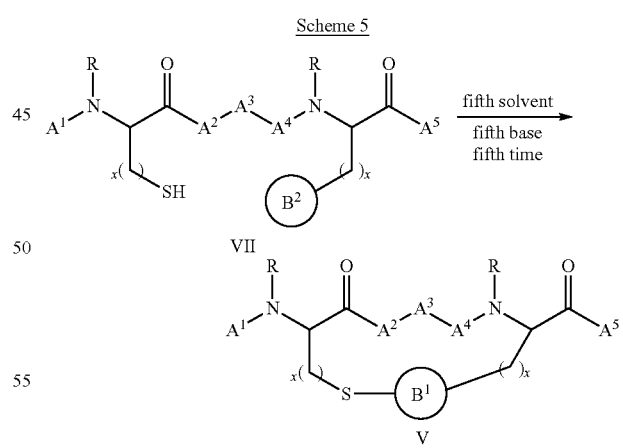

wherein, independently for each occurrence,
A$^1$ is H, an amine protecting group, a natural or unnatural amino acid, a peptide, an oligopeptide, a polypeptide, or a protein;
A$^2$, A$^3$, and A$^4$ are selected from the group consisting of a natural amino acid, an unnatural amino acid, and a plurality of natural amino acids or unnatural amino acids;

$A^5$ is OH, a carboxylate protecting group, a natural or unnatural amino acid, a peptide, an oligopeptide, a polypeptide, or a protein;

R is H or alkyl;

x is 0, 1, 2, 3, 4, 5, or 6;

is a perfluorinated aryl radical; and

is a perfluorinated aryl para-substituted diradical; or (f) according to Scheme 6, wherein the compound comprises substructure VI:

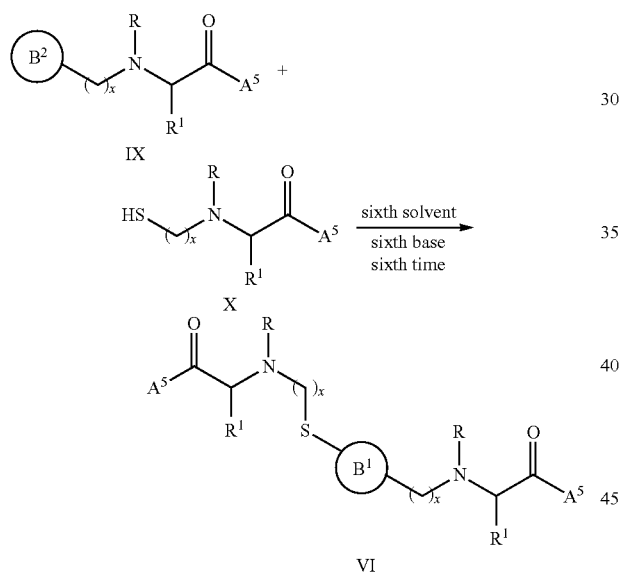

wherein, independently for each occurrence, $A^5$ is OH, a carboxylate protecting group, a natural or unnatural amino acid, a peptide, an oligopeptide, a polypeptide, or a protein;

R is H or alkyl;

x is 0, 1, 2, 3, 4, 5, or 6;

$R^1$ is H, alkyl, alkylthioalkyl, aralkyl, heteroaralkyl, hydroxyaralkyl, HO$_2$C-alkyl, H$_2$N—C(O)-alkyl, heterocycloalkyl, guanidinylalkyl, aminoalkyl, or hydroxyalkyl;

is a perfluorinated aryl radical; and

is a perfluorinated aryl para-substituted diradical.

15. The method of claim 14, wherein $A^5$ does not comprise cysteine.

16. The method of claim 14, wherein none of $A^1$, $A^2$, $A^3$, $A^4$, and $A^5$ comprises cysteine.

17. The method of claim 14, wherein one or more of $A^1$, $A^2$, $A^3$, $A^4$, and $A^5$ comprises arginine, histidine, lysine, aspartic acid, glutamic acid, serine, threonine, asparagine, glutamine, glycine, proline, alanine, valine, isoleucine, leucine, methionine, phenylalanine, tyrosine, or tryptophan.

18. The method of claim 14, wherein

is hexafluorophenyl or decafluorobiphenyl.

19. The method of claim 14, wherein

is 2,3,5,6-tetrafluorophenylene or 2,2',3,3',5,5',6,6'-octafluoro-1,1'-biphenyl-4,4'-ene.

20. The method of claim 14, wherein R is H.

21. The method of claim 14, wherein m is 2, 3, or 4.

22. The method of claim 14, wherein $R^1$ is aminoalkyl or aralkyl.

23. The method of claim 14, wherein

is pentafluorophenyl or 4'-(2,2',3,3',4,5,5',6,6'-nonafluoro-1,1'-biphenyl).

24. A method of making a compound according to Scheme 7:

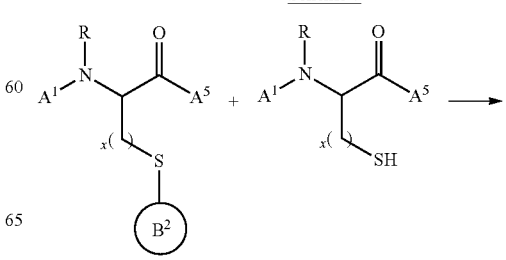

-continued

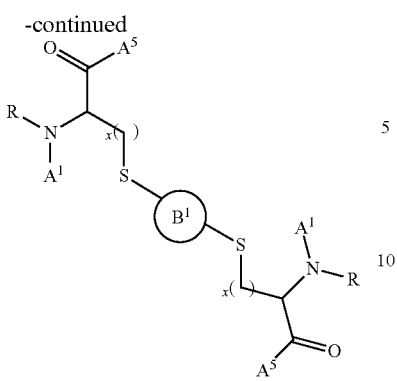

wherein, independently for each occurrence,
- $A^1$ is H, an amine protecting group, a natural or unnatural amino acid, a peptide, an oligopeptide, a polypeptide, or a protein;
- $A^5$ is OH, a carboxylate protecting group, a natural or unnatural amino acid, a peptide, an oligopeptide, a polypeptide, or a protein;
- R is H or alkyl;
- x is 0, 1, 2, 3, 4, 5, or 6;

is a perfluorinated aryl radical; and

is a perfluorinated aryl para-substituted diradical.

25. A method of disrupting or inhibiting the p53/MDM2 interaction or enhancing the activity of p53 in a cell comprising the step of:
   contacting the cell with an effective amount of a compound of claim 1, thereby disrupting or inhibiting the p53/MDM2 interaction or enhancing the activity of p53.

26. A method of treating cancer in a subject in need thereof comprising the step of:
   administering to the subject a compound of claim 1 in an amount effective to (i) disrupt or inhibit the interaction of p53 and MDM2 in a cancer cell, or (ii) enhance the activity of p53 in a cancer cell,
   thereby treating the cancer.

27. A method of disrupting or inhibiting the p53/MDM2 interaction or enhancing the activity of p53 in a cell comprising the step of:
   contacting the cell with an effective amount of a compound of claim 12, thereby disrupting or inhibiting the p53/MDM2 interaction or enhancing the activity of p53.

28. A method of treating cancer in a subject in need thereof comprising the step of:
   administering to the subject a compound of claim 12 in an amount effective to (i) disrupt or inhibit the interaction of p53 and MDM2 in a cancer cell, or (ii) enhance the activity of p53 in a cancer cell,
   thereby treating the cancer disease.

29. The method of claim 26, wherein the cancer is a glioma.

30. The method of claim 26, wherein the cancer is glioblastoma.

31. The method of claim 28, wherein the cancer is a glioma.

32. The method of claim 28, wherein the cancer is glioblastoma.

* * * * *